(12) United States Patent
Jongedijk et al.

(10) Patent No.: US 8,598,081 B2
(45) Date of Patent: Dec. 3, 2013

(54) SPECIFIC DELIVERY OF AGROCHEMICALS

(75) Inventors: Erik Jongedijk, Lokeren (BE); Peter Verheesen, Ghent (BE)

(73) Assignee: AgroSavfe N.V., Gent (BE)

( * ) Notice: Subject to any disclaimer, the term of this patent is extended or adjusted under 35 U.S.C. 154(b) by 198 days.

(21) Appl. No.: 13/081,435

(22) Filed: Apr. 6, 2011

(65) Prior Publication Data

US 2011/0244011 A1 Oct. 6, 2011

Related U.S. Application Data

(60) Provisional application No. 61/341,930, filed on Apr. 6, 2010.

(30) Foreign Application Priority Data

Apr. 6, 2010 (EP) .................................... 10159100

(51) Int. Cl.
*A01N 25/00* (2006.01)
*C07K 16/16* (2006.01)

(52) U.S. Cl.
USPC .................... 504/116.1; 504/358; 530/387.1; 530/391.7

(58) Field of Classification Search
None
See application file for complete search history.

(56) References Cited

U.S. PATENT DOCUMENTS

| | | | |
|---|---|---|---|
| 5,011,885 A | 4/1991 | Chen et al. | |
| 5,738,984 A | 4/1998 | Shoseyov | |
| 6,022,501 A | 2/2000 | Dexter et al. | |
| 6,124,117 A | 9/2000 | Kilburn et al. | |
| 6,180,141 B1 | 1/2001 | Lemercier et al. | |
| 7,494,526 B2 | 2/2009 | Yavitz | |
| 2003/0150022 A1* | 8/2003 | Newell et al. | 800/284 |
| 2005/0107256 A1 | 5/2005 | Barnwell et al. | |
| 2005/0181952 A1* | 8/2005 | Burnet et al. | 504/359 |
| 2007/0280981 A1 | 12/2007 | Birthisel | |
| 2008/0242544 A1 | 10/2008 | Duckham et al. | |

FOREIGN PATENT DOCUMENTS

| | | |
|---|---|---|
| WO | 9800500 A1 | 1/1998 |
| WO | 0144301 A1 | 6/2001 |
| WO | WO 03/031477 | 4/2003 |
| WO | 2004004453 A2 | 1/2004 |
| WO | 2004004453 A3 | 4/2004 |
| WO | WO 2005/102045 A1 | 11/2005 |

OTHER PUBLICATIONS

Jobling et al. Immunomodulation of enzyme function in plants by single-domain antibody fragments. Nature Biotechnology. Jan. 2003, vol. 21, pp. 77-80.*

(Continued)

*Primary Examiner* — Jeffrey E Russel
(74) *Attorney, Agent, or Firm* — TraskBritt

(57) ABSTRACT

Described is the specific delivery of agrochemicals to plants. More specifically, a targeting agent has at least one binding domain that specifically binds to a binding site on an intact living plant. Such

(56) References Cited

OTHER PUBLICATIONS

Deffar et al., Nanobodies—the new concept in antibody engineering, African Journal of Biotechnology, Jun. 17, 2009, pp. 2645-2652, vol. 8, No. 12, Academic Press, US.

Dewey et al., Monoclonal antibodies that differentiate between gum arabic, gum seyal and combretum gum, Food and Agricultural Immunology, 1997, pp. 123-134, vol. 9, No. 2.

European Search Report, EP 10 15 9100 dated Aug. 2, 2010.

Li et al., Immunolocalization of extension and potato tuber lectin in carrot, tomato and potato, Physiologia Plantarum, Jan. 1, 1996, pp. 708-718, vol. 97, No. 4, Munksgaard International Publishers, Copenhagen, DK.

Ligrone et al., Immunocytochemical detection of lignin-related epitopes in cell walls in bryophytes and the charalean alga *Nitella*, Plant Systematics and Evolution, Dec. 4, 2007, pp. 257-272, vol. 270, No. 3-4, Springer-Verlag, VI.

\* cited by examiner

Figure 1A:
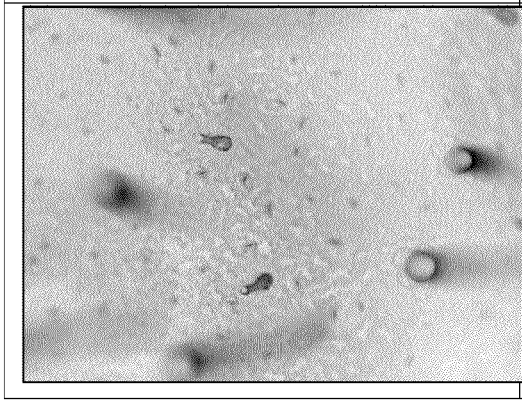
Figure 1B:
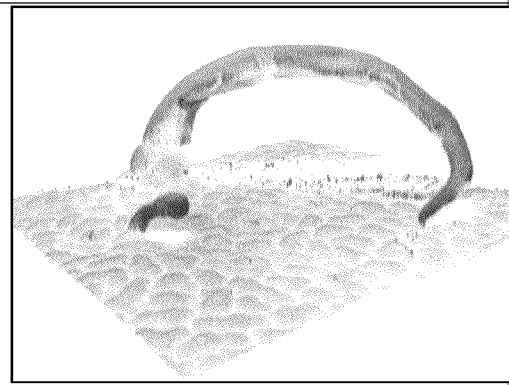
Figure 1C:
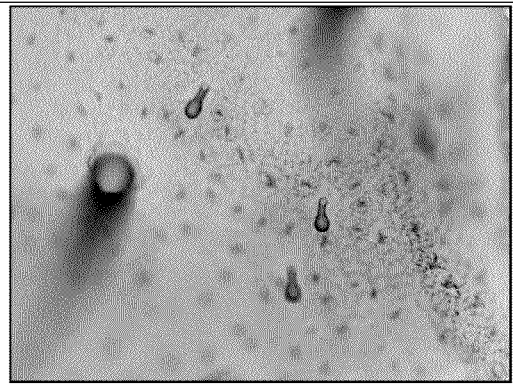
Figure 1D:
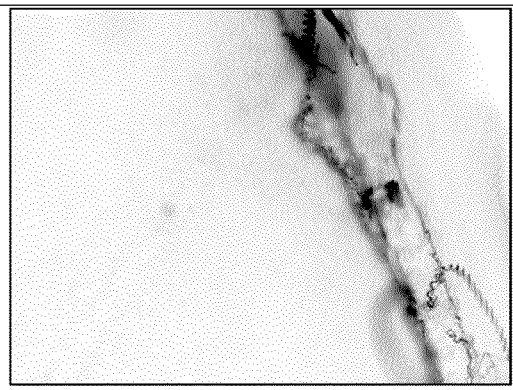
Figure 1E:
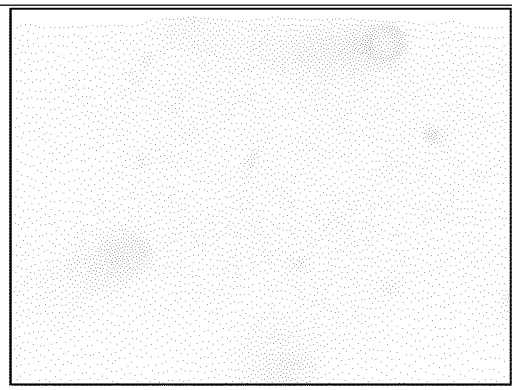
Figure 1:
Figure 1:
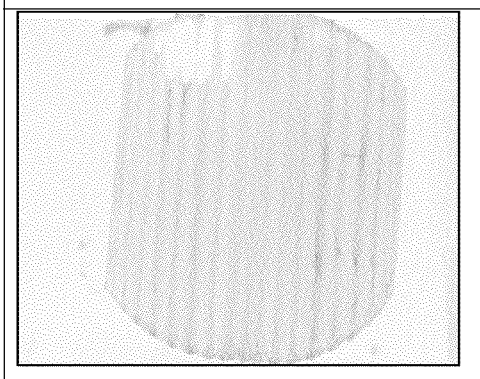

FIG. 1 (continued on next page)

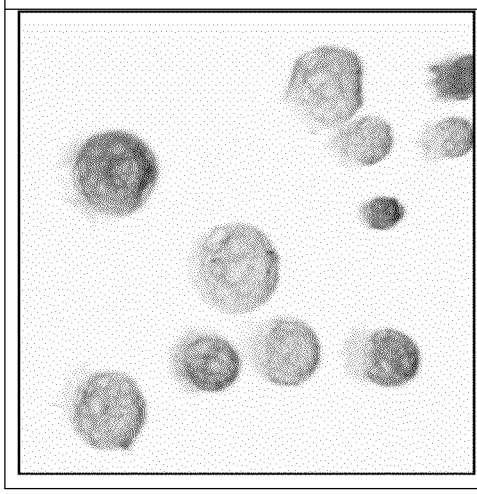
FIG. 3A
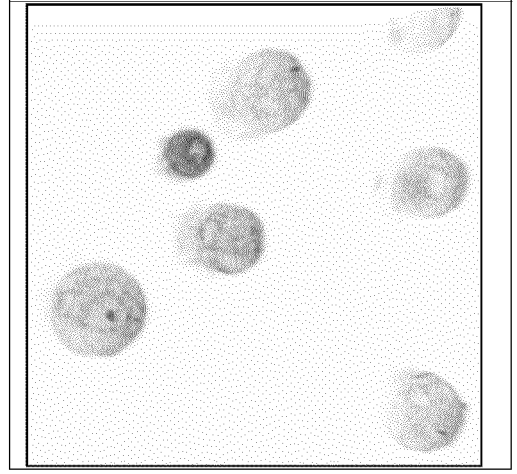
FIG. 3B
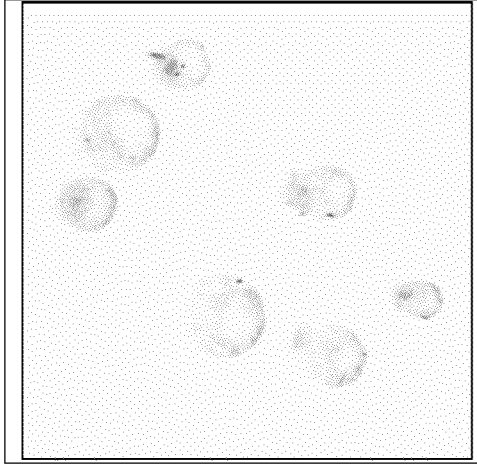
FIG. 3C
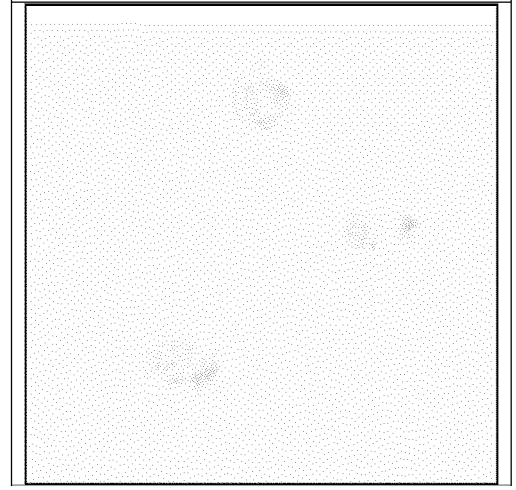
FIG. 3D
FIG. 3

SPECIFIC DELIVERY OF AGROCHEMICALS

CROSS-REFERENCE TO RELATED APPLICATIONS

This application claims the benefit under 35 U.S.C. §119 (e) of U.S. Provisional Patent Application Ser. No. 61/341,930, filed Apr. 6, 2010, and to European Patent Application Serial No. EP 10159100.6, filed Apr. 6, 2010, the disclosure of each of which is hereby incorporated herein in its entirety by this reference.

TECHNICAL FIELD

The disclosure relates to specific delivery of agrochemicals to plants. More specifically, it relates to a composition, essentially consisting of a targeting agent comprising at least one binding domain that specifically binds to a binding site on an intact living plant and an agrochemical or a combination of agrochemicals. The disclosure relates further to a binding domain that specifically binds the binding site on an intact living plant. More specifically, it relates to binding domains comprising an amino acid sequence that comprises four framework regions and three complementarity-determining regions, or any suitable fragment thereof, wherein the binding domains are capable to bind or retain a carrier onto a plant. In one embodiment, it relates to binding domains which specifically bind trichomes, stomata, cuticle, lenticels, thorns, spines, root hairs, or wax layer. It relates further to a method for delivery of agrochemicals to a plant, for improving the deposition of agrochemicals on a plant, and for retaining the agrochemicals on a plant, using targeting agents comprising the binding domains, and to a method for protecting a plant against biotic or abiotic stress or controlling plant growth using the same. Also, it relates to a method for manufacturing a specifically targeting agrochemical carrier.

BACKGROUND

For many years, horticulturist and agronomist have applied chemicals for weed control, plant protection and plant growth regulation by spraying the fields. For compositions that need to be applied on the plant, e.g., on the foliage, only a small part of the composition is bound to and retained on the part of the plant where it can exert its biological activity as large amounts are not adhering to the plant surface and are lost by drip-off or washed away by rain. Apart from giving rise to reduced efficacy of the chemical, losses of chemicals into the soil due to dripping off the plant while spraying or due to wash-out during rainfall may result in groundwater contamination, environmental damage, loss of biodiversity, and human and animal health consequences.

Several researchers have tried to solve this problem by applying slow release particles to the plant that stick to the leaves and release their content over a certain period of time. U.S. Pat. No. 6,180,141 describes composite gel microparticles that can be used to deliver plant-protection active principles. WO 2005102045 describes compositions comprising at least one phytoactive compound and an encapsulating adjuvant, wherein the adjuvant comprises a fungal cell or a fragment thereof. U.S. 20070280981 describes carrier granules, coated with a lipophilic tackifier on the surface, wherein the carrier granule adheres to the surface of plants, grasses and weeds.

Those microparticles, intended for the delivery of agrochemicals, are characterized by the fact that they stick to the plant by rather weak, aspecific interactions, such as a lipophilic interaction. Although this may have advantages compared with the normal spraying, the efficacy of such delivery method is limited, and the particles may be non-optimally distributed over the leaf, or washed away under naturally variable climatological conditions, before the release of the compound is completed. For a specific distribution and efficient retention of the microparticles, a specific, strongly binding molecule is needed that can assure that the carrier sticks to the plant till its content is completely delivered.

Cellulose binding domains (CBDs) have been described as useful agents for attachment of molecular species to cellulose (U.S. Pat. Nos. 5,738,984 and 6,124,117). Indeed, as cotton is made up of 90% cellulose, CBDs have proved useful for delivery of so called "benefit agents" onto cotton fabrics, as is disclosed in WO9800500 where direct fusions between a CBD and an enzyme were used utilizing the affinity of the CBD to bind to cotton fabric. The use of similar multifunctional fusion proteins for delivery of encapsulated benefit agents was claimed in WO03031477, wherein the multifunctional fusion proteins consist of a first binding domain which is a carbohydrate binding domain and a second binding domain, wherein either the first binding domain or the second binding domain can bind to a microparticle. WO03031477 is exemplified using a bifunctional fusion protein consisting of a CBD and an anti-RR6 antibody fragment binding to a microparticle, which complex is deposited onto cotton treads or cut grass. However, the use of such multifunctional fusion proteins for delivery of encapsulated benefit agents suffers from a number of serious drawbacks. First, although cellulose is a major component of plant cell walls and about 33% of all plant matter consists of cellulose, cellulose is, in intact living plants, shielded off from the outside environment by the plant cuticle, formed by cutin and waxes, which is an impermeable barrier with which plant cell walls are covered, making cellulose poorly accessible for binding by CBDs. Secondly, effective delivery of an encapsulated benefit agent to the plant requires simultaneous binding of the first binding domain to the plant and the second binding domain to the microparticle. As the likelihood of both binding events occurring is determined by a delicate equilibrium between the molar concentrations of the binding domains and their target molecules and the molar concentration of the bound complex, it is highly unlikely that sufficient multifunctional fusion proteins are present in solution to enable such simultaneous binding. Moreover, the equilibrium of a binding event is strongly influenced by environmental parameters such as temperature and pH, for which the optimal conditions may be considerably different for each of the binding domains. Therefore, it is highly unlikely that such simultaneous binding of two binding domains of such multifunctional fusion protein would result in a sufficiently strong binding that would retain an encapsulated benefit agent to a plant. Thirdly, although binding of a CBD is to a certain extent specific for cellulose, using a multifunctional fusion protein in which CBD should bind to the plant is to be considered as a generic binding approach, as all plants contain cellulose, and is therefore similar to aspecific sticking with tackifiers or stickers. A targeted approach in which specific binding of a binding domain would allow discrimination between binding to one plant species versus another would be of considerably higher value. WO03031477 also suggests, without further exemplification, that other binders to carbohydrates or polysaccharides can be used to generate fusion proteins to deposit microparticles onto living organisms. However, neither binding domains other than CBDs, nor binding domains binding to intact living plants were disclosed in WO03031477.

Molecules that are well known for their specificity and high affinity to particular targets are antibodies. Antibodies can be generated against a broad variety of targets, and antibodies that were generated to study plant cell wall architecture and dynamics have been described to bind specifically to particular plant constituents, predominantly constituents of the plant cell wall (Penell et al., 1989; Jones et al., 1997; Willats et al., 1998; Willats and Knox, 1999; Willats et al., 2001). However, it is unclear whether any of the plant cell wall constituents to which the antibodies have been generated, would be directly accessible for an antibody from the outside environment. Moreover, antibodies are by their very nature as components of the adaptive immune system construed such that they bind their targets under physiological conditions, including tightly regulated pH, temperature, and blood's normal osmolarity range. Should one consider to use antibodies for targeted delivery of agrochemicals, the antibodies should not only be capable of binding their target on an intact living plant in an agrochemical formulation, for which physicochemical characteristics deviate substantially from physiological conditions, they should also be capable to bind strongly enough to retain a carrier onto a plant. For neither of the plant-binding antibodies earlier described, either of these two crucial characteristics have been demonstrated.

The variable domains of camelid heavy chain antibodies (VHH) are a particularly interesting type of antibody fragments, as they are small, 15 kDa single-chain proteins, which can be selected for displaying high affinity for their targets. Also, by their nature as small single-chain molecules, VHH are easy to produce and have superior stability characteristics over conventional antibodies. However, so far, no plant-binding VHH have been described. Moreover, although VHH that are covalently linked to a solid resin particle have been shown to maintain functionality in the sense that they are able to capture antigen from a solution (WO 0144301), it has not been shown, nor can it be expected, that the affinity of VHH for its target is sufficient to retain a carrier onto a solid plant surface.

There is still an unmet need for a specific delivery method for agrochemicals in which the agrochemical is delivered or deposited on or near its site of action on an intact living plant utilizing a binding domain that can bind specifically and strongly to the intact living plant, and is capable of retaining an agrochemical or a carrier containing the agrochemical onto the plant.

DISCLOSURE

We have isolated binding domains, more specifically binding domains comprising an amino acid sequence (or "peptide") that comprises four framework regions (FR) and three complementarity-determining regions (CDR) (FR and CDR definitions according to Kabat), wherein the binding domains are capable to bind a binding site on an intact living plant and, surprisingly, in doing so, are capable of retaining an agrochemical or a carrier containing an agrochemical to the plant. Preferably, the binding domains remain stable and retain their binding capacity under harsh conditions, such as variable temperature, pH, salt concentration, availability of water or moisture; more preferably, the binding domains remain stable and retain their binding capacity in an agrochemical formulation. Binding domains comprising four FRs and three CDRs, preferably in a sequence FR1-CDR1-FR2-CDR2-FR3-CDR3-FR4, are known to the person skilled in the art and have been described, as a non-limiting example in Wesolowski et al. (2009). Preferably, the binding domains are derived from camelid antibodies, preferably, from heavy chain camelid antibodies, devoid of light chains, such as variable domains of heavy chain camelid antibodies (VHH).

Targeting agents comprising these binding domains, can retain agrochemicals specifically to binding sites on the plant or plant parts and can be used to deliver and retain agrochemicals to the plant, preferably to the intact living plant, wherein the binding domains comprised in such targeting agents specifically bind to binding sites on the plant, where the agrochemicals can exert their activity. Agrochemical compositions comprising at least one targeting agent and an agrochemical, preferably bound on or comprised in a carrier, may be suitable to allow the use of a reduced dose of the agrochemical and/or reduction of the frequency of application of the agrochemical, comprised in such composition whilst maintaining its overall efficacy. Moreover, when comprised in a composition hereof, the agrochemical may exert its activity over a longer period of time, eventually resulting in less agrochemical being lost and contaminating the environment; also, by applying an agrochemical in a composition hereof, it is possible to introduce specificity into the activity of the agrochemical that is otherwise not present.

A first aspect hereof is a binding domain capable to bind at least one binding site on an intact living plant.

An "intact living plant," as used herein, means a plant as it grows, whether it grows in soil, in water or in artificial substrate, and whether it grows in the field, in a greenhouse, in a yard, in a garden, in a pot or in hydroponic culture systems. An intact living plant preferably comprises all plant parts (roots, stem, branches, leaves, needles, thorns, flowers, seeds . . . ) that are normally present on such plant in nature, although some plant parts, such as, e.g., flowers, may be absent during certain periods in the plant's life cycle. An intact living plant excludes plant parts that have been removed from the plant, such as leaves and flowers that have been cut and separated from the plant. However, an intact living plant includes plants that have been damaged by normal natural events such as damage by weather (such as, but not limited to wind, rain, or hail), by animals (whether by animals feeding on the plants or by animals trampling on the plants), by plant pests (such as, but not limited to insects, nematodes and fungi), or damage caused by agricultural practice such as, but not limited to pruning, harvesting of fruit, or harvesting of flowers. Plants include gymnosperms and angiosperms, monocotyledons and dicotyledons, trees, fruit trees, field and vegetable crops and ornamental species. As a non-limiting example, the plants can be cedars, cypresses, firs, junipers, larches, pines, redwoods, spruces, yews, gingko, oilpalm, rubber tree, oak, beech, corn, cotton, soybean, wheat, rice, barley, rye, sorghum, millet, rapeseed, beans, peas, peanuts, sunflower, potato, tomato, sugarcane, sugarbeet, cassaya, tobacco, banana, apple, orange, lemon, olive, pineapple, avocado, vines, lettuce, cabbage, carrot, eggplant, pepper, melon, rose, lilies, chrysanthemum, grass-like weeds, or broadleaved weeds.

A "binding site," as used herein, means a molecular structure or compound, such as a protein, a (poly)peptide, a (poly) saccharide, a glycoprotein, a lipoprotein, a fatty acid, a lipid or a nucleic acid or a particular region in such molecular structure or compound or a particular conformation of such molecular structure or compound, or a combination or complex of such molecular structures or compounds. Preferably, the binding site comprises at least one antigen. "Antigen," as used herein, means a molecule capable of eliciting an immune response in an animal. Preferably, the binding site is comprised in a plant structure such as a trichome, stomata, lenticels, thorns, spines, root hairs, cuticle or wax layer. Even more preferably, the binding site is comprised in a plant structure such as a trichome, stomata or cuticle. The binding site may be unique for one particular plant structure, or it may be more generally comprised in more than one plant structure. Preferably, the binding site is present on a particular part of the plant, such as the leaves, stems, roots, fruits, cones, flowers, bulbs or tubers. Even more preferably, the binding site is present on the surface of such particular part of the plant, meaning that the binding site is present at, for example, the leaf surface, the stem surface, the root surface, the fruit surface, the cone surface, the flower surface, the bulb surface or the tuber surface. The binding site may be unique for one particular plant part, or it may be more generally present on more than one plant part.

A "binding domain," as used herein, means the whole or part of a proteinaceous (protein, protein-like or protein containing) molecule that is capable of binding using specific intermolecular interactions to a target molecule. A binding domain can be a naturally occurring molecule, e.g., fibronectin, it can be derived from a naturally occurring molecule, e.g., from components of the innate or adaptive immune system, or it can be entirely artificially designed. A binding domain can be immunoglobulin-based or it can be based on domains present in proteins, including but not limited to microbial proteins, protease inhibitors, toxins, fibronectin, lipocalins, single-chain antiparallel coiled coil proteins or repeat motif proteins. Non-limiting examples of such binding domains are carbohydrate binding domains (CBD) (Blake et al, 2006), heavy chain antibodies (hcAb), single domain antibodies (sdAb), minibodies (Tramontano et al., 1994), the variable domain of camelid heavy chain antibodies (VHH), the variable domain of the new antigen receptors (VNAR), affibodies (Nygren et al., 2008), alphabodies (WO2010066740), designed ankyrin-repeat domains (DARPins) (Stumpp et al., 2008), anticalins (Skerra et al., 2008), knottins (Kolmar et al., 2008) and engineered CH2 domains (nanoantibodies; Dimitrov, 2009). Preferably, the binding domain consists of a single polypeptide chain and is not post-translationally modified. More preferably, the binding domain is not a CBD. Even more preferably, the binding domain is derived from an innate or adaptive immune system, preferably from a protein of an innate or adaptive immune system. Still more preferably, the binding domain is derived from an immunoglobulin. Most preferably, the binding domain comprises four framework regions and three complementarity-determining regions, or any suitable fragment thereof (which will then usually contain at least some of the amino acid residues that form at least one of the complementarity-determining regions). Preferably, a binding domain is easy to produce at high yield, preferably in a microbial recombinant expression system, and convenient to isolate and/or purify subsequently. Also preferably, a binding domain is stable, both during storage and during utilization, meaning that the integrity of the binding domain is maintained under storage and/or utilization conditions, which may include elevated temperatures, freeze-thaw cycles, changes in pH or in ionic strength, UV-irradiation, presence of harmful chemicals and the like. More preferably, the binding domain is stable in an agrochemical formulation. An "agrochemical formulation" as used herein means a composition for agrochemical use, as further defined, comprising at least one active substance, optionally with one or more additives favoring optimal dispersion, atomization, deposition, leaf wetting, distribution, retention and/or uptake of agrochemicals. As a non-limiting example, such additives are diluents, solvents, adjuvants, surfactants, wetting agents, spreading agents, oils, stickers, thickeners, penetrants, buffering agents, acidifiers, anti-settling agents, anti-freeze agents, photo-protectors, defoaming agents, biocides and/or drift control agents. Most preferably, the binding domain remains stable in an agrochemical formulation when stored at ambient temperature for a period of two years or when stored at 54° C. for a period of two weeks. Preferably, the binding domain is selected from the group consisting of DARPins, knottins, alphabodies and VHH. More preferably, the binding domain is selected from the group consisting of alphabodies and VHH. Most preferably, the binding domain is a VHH.

Binding of the binding domain to the binding site or to an antigen comprised in the binding site occurs with high affinity. The dissociation constant is commonly used to describe the affinity between a binding domain and its target molecule. Preferably, the dissociation constant of the binding between the binding domain and the target molecule comprised in the binding site is lower than $10^{-5}$ M, more preferably, the dissociation constant is lower than $10^{-6}$ M, even more preferably, the dissociation constant is lower than $10^{-7}$ M, most preferably, the dissociation constant is lower than $10^{-8}$ M. Preferably, binding of the binding domain to the binding site is specific, meaning that the binding domain binds to the binding site only if the target molecule is present in the binding site and that the binding domain does not bind, or binds with much lower affinity, to a binding site lacking the target molecule. Specificity of binding of a binding domain can be analyzed by methods such as ELISA, as described in Example 2, in which the binding of the binding domain to its target molecule is compared with the binding of the binding domain to an unrelated molecule and with aspecific sticking of the binding domain to the reaction vessel. Specificity can also be expressed as the difference in affinity of a binding domain for its target molecule versus the affinity for an unrelated molecule. Preferably, the ratio of the affinity of the binding domain for its target molecule versus its affinity for an unrelated molecule is larger than 10, more preferably, the ratio is larger than 20, most preferably, the ratio is larger than 100. Binding of the binding domain can be specific for one particular plant structure, meaning that the binding site, comprised in such plant structure, is not or to a much lesser extent present in other plant structures; or the binding can be more general to more than one plant structure, if the binding site is present in more than one plant structure. Binding of the binding domain can be specific for one particular plant part, meaning that the binding site, present in or on such plant part, possibly comprised in a plant structure on such plant part, is not or to a much lesser extent present in other plant parts; or the binding can be more general to more than one plant part, if the binding site is present in more than one plant part. Binding of the binding domain can be specific for one particular plant species, meaning that the binding site, present in or on such plant species, is not or to a much lesser extent present in other plant species; or the binding can be more general to more than one plant species, if the binding site is present in more than one plant species. Binding of the binding domain can be specific for one particular plant genus, meaning that the binding site, present in or on such plant genus, is not or to a much lesser extent present in other plant genera; or the binding can be more general to more than one plant genus, if the binding site is present in more than one plant genus. Binding of the binding domain can be specific for one particular growth stage of the plant, meaning that the binding site, present in or on such plant at a particular growth stage, is not or to a much lesser extent present in the plant at another growth stage; or the binding can be more general to more than one plant growth stage, if the binding site is present in more than one plant growth stage. All types of binding specificity of the binding domains may have their specific use, as will be explained below.

Preferably, the binding of the binding domain to the binding site is still functional under harsh conditions, such as low or high temperature, low or high pH, low or high ionic strength, UV-irradiation, low availability of water, presence of denaturing chemicals or the like. In one embodiment, the harsh conditions are defined by a pH range from 4 to 9, more preferably, by a pH range from 3 to 10, even more preferably, by a pH range from 2 to 10, most preferably, by a pH range from 1 to 11. In another embodiment, the harsh conditions are defined by a temperature range from 4-50° C., more preferably, a temperature range from 0-55° C., even more preferably, a temperature range from 0-60° C. In another embodiment, the harsh conditions are defined by the presence of an agrochemical formulation as defined above.

Preferably, the binding of the binding domain to the binding site is strong enough to bind, more preferably, to retain, a carrier to the binding site; depending on the size of the carrier and on the affinity of the binding domain, one or more binding domains may bind to one or more binding sites and cooperate such that the resulting avidity of the binding domains for the binding site(s) ensures strong binding of the carrier, preferably retaining the carrier, onto the plant. A "carrier," as used herein, means any solid, semi-solid or liquid carrier in or on(to) which an active substance can be suitably incorporated, included, immobilized, adsorbed, absorbed, bound, encapsulated, embedded, attached, or comprised. Non-limiting examples of such carriers include nanocapsules, microcapsules, nanospheres, microspheres, nanoparticles, microparticles, liposomes, vesicles, beads, a gel, weak ionic resin particles, liposomes, cochleate delivery vehicles, small granules, granulates, nano-tubes, bucky-balls, water droplets that are part of an water-in-oil emulsion, oil droplets that are part of an oil-in-water emulsion, organic materials such as cork, wood or other plant-derived materials (e.g., in the of seed shells, wood chips, pulp, spheres, beads, sheets or any other suitable form), paper or cardboard, inorganic materials such as talc, clay, microcrystalline cellulose, silica, alumina, silicates and zeolites, or even microbial cells (such as yeast cells) or suitable fractions or fragments thereof (as further described herein). "Retain" as used herein means that the binding force resulting from the affinity or avidity of either one single binding domain or a combination of two or more binding domains for its or their binding site is larger than the combined force and torque imposed by the gravity of the carrier, the force and torque, if any, caused by the flow or drip off of a sprayed agrochemical solution and the force and torque, if any, imposed by shear forces caused by one or more external factors. In one embodiment, the external factor is rain, irrigation, snow, hail or wind. One particular advantage of binding a carrier by specific binding over aspecific binding is that specific binding is more resistant to external shear forces applied to the carrier (Cozens-Roberts et al., 1990).

Preferably, a binding domain hereof binds to a binding site, or to an antigen comprised in such binding site, present in or on one or more particular parts of the intact living plant. Preferably, the parts of the intact living plant are selected from the group consisting of leaves, stem, roots, fruits, cones, flowers, bulbs or tubers. More preferably, the parts of the intact living plant are selected from the group consisting of leaves, stem or roots. Preferably, a binding domain hereof binds to a binding site, or to an antigen comprised in such binding site, on the surface of the intact living plant. A "surface," as used herein, can be any surface as it occurs on the intact living plant; or on one or more parts of the intact living plant, however, it excludes histological plant preparations. Preferably, the surface of the intact living plant is the surface of a part of the intact living plant, selected from the group consisting of leaf surface, stem surface, root surface, fruit surface, cone surface, flower surface, bulb surface or tuber surface; even more preferably, the surface of the intact living plant is the surface of a part of the intact living plant, selected from the group consisting of root surface, stem surface and leaf surface.

Preferably, a binding domain hereof binds to a binding site, or to an antigen comprised in such binding site, in or on a particular structure of the intact living plant or in or on a particular structure of a particular part of the intact living plant; more preferably, in or on a particular structure involved or implicated to be involved in transport of nutrients, agrochemicals or other chemicals into the plant and/or involved or implicated to be involved in plant defense. Preferably, the particular structure is selected from the group consisting of trichomes, stomata, lenticels, thorns, spines, root hairs, cuticle and wax layer, even more preferably, the particular structure is selected from the group consisting of trichomes, stomata and cuticle. In one embodiment, the binding domain is binding to a binding site, or to an antigen comprised in such binding site, in or on plant trichomes. Plant trichomes are known to the person skilled in the art, and include, but are not limited to glandular trichomes and leaf hairs. Plant trichomes are active in plant defense (Lai et al, 2000), but especially non-glandular trichomes are also cited as possible targets for infection (Cabo et al., 2006). Trichomes, including glandular trichomes, are also implicated in the transport of polar compounds across plant cuticles into the plant (Schreiber, 2005). This makes trichomes an ideal target for delivery of agrochemicals, either by enhancing the natural defense or by concentrating agrochemicals at the site of attack or by improved delivery of (polar) agrochemicals into the plant. In another embodiment, the binding domain binds to a binding site, or to an antigen comprised in such binding site, in or on stomata. Stomata are essential to allow $CO_2$ to diffuse into the plant and to minimize water loss. Stomata are also used as a major entry site for pathogens, especially microbes (Underwood et al. 2007). "Microbes," as used herein, means bacteria, viruses, fungi and the like. Moreover they are directly implicated in plant defense via specific signaling pathways allowing the plant to close stomata upon microbial infection (Melotto et al., 2006). In yet another embodiment, the binding domain binds to a binding site, or to an antigen comprised in such binding site, in or on root hairs. Root hairs are known to be important for microbial attachment to and colonization of plants (Gage, 2004; Laus et al., 2005) and are, therefore, an important target for the delivery of agrochemicals. In another embodiment, the binding domain binds to a binding site, or an antigen comprised in such binding site, in or on plant cuticle. Plant cuticles are known to be important for microbial attachment to and colonization of plants and to play an important role in delivery and deposition of lipophilic agrochemicals into the plant (Schreiber, 2005) and are therefore an important target for the delivery and deposition of agrochemicals.

In one embodiment, the binding domain hereof is binding gum arabic. In another embodiment, the binding domain is binding lectins, lectin-like domains, extensins, or extensin-like domains; more preferably, the binding domain is binding potato lectin. Preferably, the binding domain comprises four framework regions and three complementarity-determining regions, or any suitable fragment thereof (which will then usually contain at least some of the amino acid residues that form at least one of the complementarity-determining regions); more preferably, the binding domain is derived from a heavy chain camelid antibody, even more preferably, the binding domain comprises a VHH sequence. Heavy chain camelid antibodies, and the VHH-derived sequences are known to the person skilled in the art. Camelid antibodies have been described, amongst others in WO9404678 and in WO2007118670, incorporated herein by reference. Still even more preferably, VHH comprises two disulphide bridges. Most VHH molecules have only one disulphide bridge; the presence of an additional disulphide bridge will give extra stability to the antibody domain, which is an advantageous characteristic for a binding domain that needs to be stable under harsh conditions. Most preferably, VHH preferably consists of a sequence selected from the group consisting of SEQ ID NO:1-SEQ ID NO:42 (3A2, 3B4, 3B7, 3D10, 3D2, 3D8, 3E6, 3F5, 3F7, 3F9, 3G2, 3G4, 3H10, 3H8, 4A1, 5B5, 5B6, 5C4, 5C5, 5D4, 5E5, 5F5, 5G2, 5G5, 5H5, 7A2, 7C2, 7D2, 7E1_1, 7F1, 8B10, 8B12, 9A1, 9B5, 9C4, 9D5, 9E1, 9E4, 9F4, 9H1, 9H2 and 12H4), or any suitable fragment thereof (which will then usually contain at least some of the amino acid residues that form at least one of the complementarity-determining regions) or homologues thereof. Homologues, as used here are sequences wherein each or any framework region and each or any complementarity-determining region shows at least 80% identity, preferably, at least 85% identity, more preferably, 90% identity, even more preferably, 95% identity with the corresponding region in the reference sequence (i.e., FR1_homologue versus FR1_reference, CDR1_homologue versus CDR1_reference, FR2_homologue versus FR2_reference, CDR2_homologue versus CDR2_reference, FR3_homologue versus FR3_reference, CDR3_homologue versus CDR3_reference and FR4_homologue versus FR4_reference) as measured in a BLASTp alignment (Altschul et al., 1997; FR and CDR definitions according to Kabat).

A second aspect hereof is a targeting agent, capable to retain an agrochemical on a plant and/or a plant part.

A "targeting agent," as used herein, is a molecular structure, preferably with a polypeptide backbone, comprising at least one binding domain. A targeting agent in its simplest form consists solely of one single binding domain; however, a targeting agent can comprise more than one binding domain and can be monovalent or multivalent and monospecific or multispecific, as further defined. Apart from one single or multiple binding domains, a targeting agent can further comprise other moieties, which can be either chemically coupled or fused, whether N-terminally or C-terminally or even internally fused, to the binding domain. The other moieties include, without limitation, one or more amino acids, including labeled amino acids (e.g., fluorescently or radio-actively labeled) or detectable amino acids (e.g., detectable by an antibody), one or more monosaccharides, one or more oligosaccharides, one or more polysaccharides, one or more lipids, one or more fatty acids, one or more small molecules or any combination of the foregoing. In one embodiment, the other moieties function as spacers or linkers in the targeting agent.

"Agrochemical," as used herein, means any active substance or principle that may be used in the agrochemical industry (including agriculture, horticulture, floriculture and home and garden uses, but also products intended for non-crop related uses such as public health/pest control operator uses to control undesirable insects and rodents, household uses, such as household fungicides and insecticides and agents, for protecting plants or parts of plants, crops, bulbs, tubers, fruits (e.g., from hainful organisms, diseases or pests); for controlling, preferably promoting or increasing, the growth of plants; and/or for promoting the yield of plants, crops or the parts of plants that are harvested (e.g., its fruits, flowers, seeds, etc.). Examples of such substances will be clear to the skilled person and may, for example, include compounds that are active as insecticides (e.g., contact insecticides or systemic insecticides, including insecticides for household use), herbicides (e.g., contact herbicides or systemic herbicides, including herbicides for household use), fungicides (e.g., contact fungicides or systemic fungicides, including fungicides for household use), nematicides (e.g., contact nematicides or systemic nematicides, including nematicides for household use) and other pesticides or biocides (for example, agents for killing insects or snails); as well as fertilizers; growth regulators such as plant hormones; micronutrients, safeners, pheromones; repellants; insect baits; and/or active principles that are used to modulate (i.e., increase, decrease, inhibit, enhance and/or trigger) gene expression (and/or other biological or biochemical processes) in or by the targeted plant (e.g., the plant to be protected or the plant to be controlled), such as nucleic acids (e.g., single-stranded or double-stranded RNA, as, for example, used in the context of RNAi technology) and other factors, proteins, chemicals, etc., known per se for this purpose, etc. Examples of such agrochemicals will be clear to the skilled person; and, for example, include, without limitation: glyphosate, paraquat, metolachlor, acetochlor, mesotrione, 2,4-D,atrazine, glufosinate, sulfosate, fenoxaprop, pendimethalin, picloram, trifluralin, bromoxynil, clodinafop, fluoroxypyr, nicosulfuron, bensulfuron, imazetapyr, dicamba, imidacloprid, thiamethoxam, fipronil, chlorpyrifos, deltamethrin, lambda-cyhalotrin, endosulfan, methamidophos, carbofuran, clothianidin, cypermethrin, abamectin, diflufenican, spinosad, indoxacarb, bifenthrin, tefluthrin, azoxystrobin, thiamethoxam, tebuconazole, mancozeb, cyazofamid, fluazinam, pyraclostrobin, epoxiconazole, chlorothalonil, copper fungicides, trifloxystrobin, prothioconazole, difenoconazole, carbendazim, propiconazole, thiophanate, sulphur, boscalid and other known agrochemicals or any suitable combination(s) thereof. Other suitable agrochemicals will be clear to the skilled person based on the disclosure herein, and may, for example, be any commercially available agrochemical, and, for example, include each of the compounds listed in Phillips McDougall, AgriService November 2007 V4.0, Products Section—2006 Market, Product Index pp. 10-20. The agrochemical can occur in different forms, including but not limited to, as crystals, as micro-crystals, as nano-crystals, as co-crystals, as a dust, as granules, as a powder, as tablets, as a gel, as a soluble concentrate, as an emulsion, as an emulsifiable concentrate, as a suspension, as a suspension concentrate, as a suspoemulsion, as a dispersion, as a dispersion concentrate, as a microcapsule suspension or as any other form or type of agrochemical formulation clear to those skilled in the art. Agrochemicals not only include active substances or principles that are ready to use, but also precursors in an inactive form, which may be activated by outside factors. As a non limiting example, the precursor can be activated by pH changes, caused by plant wounds upon insect damage, by enzymatic action caused by fungal attack, or by temperature changes or changes in humidity.

"Plant part," as used herein, means any plant part whether part of an intact living plant or whether isolated or separated from an intact living plant, and even dead plant material can be envisaged. Preferably, the plant parts are selected from the group consisting of leaves, stem, roots, fruits, cones, flowers, bulbs and tubers. More preferably, the plant parts are selected from the group consisting of leaves, stem and roots. Even more preferably, the plant is an intact living plant and/or the plant parts are plant parts of an intact living plant.

In order to be capable to retain an agrochemical on a plant or a plant part, either one single or multiple targeting agents are either fused with or attached to the agrochemical, either by a covalent bond, by hydrogen bonds, by dipole-dipole interactions, by weak Van der Waals forces or by any combination of the foregoing. "Attached," as used herein, means coupled to, connected to, anchored in, admixed with or covering.

In one embodiment, the agrochemical is bound on or comprised in a carrier, as defined above, wherein the targeting agent is coupled either to the carrier or to the agrochemical. Preferably, the binding domain is coupled to the carrier. "Coupled," as used herein, can be any coupling allowing the retention of the agrochemical or carrier containing the agrochemical by the targeting agent; it can be a covalent as well as a non-covalent binding. Preferably, the coupling is a covalent binding. It is clear to the person skilled in the art how binding domains and/or targeting agents can be coupled to any type of functional groups present at the outer surface of a carrier. "Functional group," as used herein, means any chemical group to which a protein can be covalently bound, including but not limited to carboxyl-, amine-, hydroxyl-, sulfhydryl-, or alkynyl group. As a non-limiting example, coupling by forming of a carbodiimide bond between carboxyl groups on the outer surface of the carrier and the amine-groups of the binding domain and/or targeting agent can be applied. Binding domains and/or targeting agents can be coupled with our without linking agents to the carrier. In the case of a microbial cell or phage, the targeting agent hereof may be encoded by the microbial cell or phage genome, whereas the agrochemical is contained in or coupled to the microbial cell or phage, either as fusion protein or by chemical linking. A "linking agent," as used herein, may be any linking agent known to the person skilled in the art; preferably, the linking agent is increasing the flexibility of the targeting agent bound on the carrier, thereby facilitating the binding of the binding domain comprised in the targeting agent to the binding site on the plant. Examples of such linking agents can be found in WO0024884 and WO0140310.

The carrier may be a microcarrier. A "microcarrier," as used herein, is a particulate carrier where the particles are less than 500 μm in diameter, preferably, less than 250 μm, even more preferably, less than 100 μm, most preferably, less than 50 μm. Microcarriers for delivery of agrochemicals are known to the person skilled in the art, and include, but are not limited to nanocapsules, microcapsules, nanospheres, microspheres, weak ionic resin particles, polymer particles, composite gel particles, particles made from artificially lignified cellulose, liposomes, vesicles and cochleate delivery vehicles. It is also possible that one or more agrochemicals are either present on or within a microbial cell (e.g., a yeast cell) or a phage (for example, because the one or more agrochemicals can be loaded into (or onto) such cells or are biologicals that have been produced/expressed in the microbial cell) or that the one or more agrochemicals are associated (e.g., bound to or embedded in) with cell fragments (e.g., fragments of cells walls or cell membranes), cell fractions or other cell debris (for example, obtained by fractionating or lysing the microbial cells into (or onto) which the one or more agrochemicals have been loaded, produced or expressed) and that therefore the microbial cells or phages are used as microcarriers. As used herein microcarrier, microparticle, microsphere, microcapsule, nanoparticle, nanocapsule and nanosphere can be used interchangeably. Such microcarriers have been described, amongst others, in U.S. Pat. No. 6,180,141, WO2004004453, WO2005102045 and U.S. Pat. No. 7,494,526, incorporated here by reference. Preferably, the microcarrier is a microparticle composed of a natural polymer. Characteristics of microcarriers can be such that they enable slow release of the agrochemical, delayed release of the agrochemical or immediate release of the agrochemical, all types of microcarriers have their specific use. Microcarriers may naturally comprise cross-linkable residues suitable for covalent attachment or microcarriers may be derivatized to introduce suitable cross-linkable groups to methods well known in the art. Such derivatization may occur prior to manufacturing of the microcarrier, i.e., at the level of the raw materials that will be used in the manufacturing process, it may occur during the manufacturing process of the microcarrier or it may occur subsequent to the manufacturing of the microcarrier. In one specific embodiment, functional groups on the microcarrier may be bound to a linking agent or spacer, which is on its turn bound to a targeting agent as defined above.

In another embodiment, one or more binding domains comprised in the targeting agent, bind to a binding site or to an antigen comprised in such binding site, present in or on one or more particular parts of the plant, preferably the intact living plant. Preferably, the parts of the plant, more preferably of the intact living plant, are selected from the group consisting of leaves, stem, roots, fruits, cones, flowers, bulbs or tubers. More preferably, the parts of the plant, preferably the intact living plant, are selected from the group consisting of leaves, stem or roots. More preferably, one or more binding domains comprised in the targeting agent, bind to a binding site or to an antigen comprised in such binding site, on the surface of the plant, preferably the intact living plant. Preferably, the surface of the plant, preferably the intact living plant, is the surface of a part of the plant, preferably the intact living plant, selected from the group consisting of leaf surface, stem surface, root surface, fruit surface, cone surface, flower surface, bulb surface or tuber surface; even more preferably, the surface of the plant, preferably the intact living plant, is the surface of a part of the plant, preferably the intact living plant, selected from the group consisting of root surface, stem surface and leaf surface.

In another embodiment, one or more binding domains comprised in the targeting agent, bind to binding site, or to an antigen comprised in such binding site, in or on a particular structure of the plant, preferably the intact living plant, or in or on a particular structure of a particular part of the plant, preferably the intact living plant; more preferably, in or on a particular structure involved or implicated to be involved in transport of nutrients, agrochemicals or other chemicals into the plant and/or involved or implicated to be involved in plant defense. Preferably, the particular structure is selected from the group consisting of trichomes, stomata, lenticels, thorns, spines, root hairs, cuticle and wax layer, even more preferably, the particular structure is selected from the group consisting of trichomes, stomata and cuticle. In one embodiment, the one or more binding domains comprised in the targeting agent, bind to binding site, or to an antigen comprised in such binding site, in or on plant trichomes. In another embodiment, the one or more binding domains comprised in the targeting agent, bind to binding site, or to an antigen comprised in such binding site, in or on stomata. In yet another embodiment, the one or more binding domains comprised in the targeting agent, bind to binding site, or to an antigen comprised in such binding site, in or on plant cuticle.

In yet another embodiment, one or more binding domains hereof and comprised in the targeting agent, bind to gum arabic. In another embodiment, one or more of the binding domains comprised in the targeting agent, bind to lectins, lectin-like domains, extensins, or extensin-like domains; more preferably, the binding domain is binding potato lectin.

Preferably, one or more of the binding domains comprised in the targeting agent comprises four framework regions and three complementarity-determining regions, or any suitable fragment thereof (which will then usually contain at least some of the amino acid residues that form at least one of the complementarity-determining regions); more preferably, one or more of the binding domains comprised in the targeting agent is derived from a heavy chain camelid antibody, even more preferably, one or more of the binding domains comprised in the targeting agent comprises a VHH sequence. Still even more preferably, VHH comprises two disulphide bridges. Most preferably, VHH preferably consists of a sequence selected from the group consisting of SEQ ID NO:1-SEQ ID NO:42 (3A2, 3B4, 3B7, 3D10, 3D2, 3D8, 3E6, 3F5, 3F7, 3F9, 3G2, 3G4, 3H10, 3H8, 4A1, 5B5, 5B6, 5C4, 5C5, 5D4, 5E5, 5F5, 5G2, 5G5, 5H5, 7A2, 7C2, 7D2, 7E1_1, 7F1, 8B10, 8B12, 9A1, 9B5, 9C4, 9D5, 9E1, 9E4, 9F4, 9H1, 9H2 and 12H4), or any suitable fragment thereof (which will then usually contain at least some of the amino acid residues that form at least one of the complementarity-determining regions) or homologues thereof.

A third aspect hereof is the use of a targeting agent hereof to deliver and retain an agrochemical or a combination of agrochemicals to a plant or plant part.

Any plant part whether part of an intact living plant or whether isolated or separated from an intact living plant, and even dead plant material can be envisaged as a target to deliver and retain an agrochemical or a combination of agrochemicals using a targeting agent hereof. Preferably, the plant parts are selected from the group consisting of leaves, stem, roots, fruits, cones, flowers, bulbs and tubers. More preferably, the plant parts are selected from the group consisting of leaves, stem and roots. Even more preferably, the plant is an intact living plant and/or the plant parts are plant parts of an intact living plant. Delivery is carried out using any suitable or desired manual or mechanical technique for application of an agrochemical or a combination of agrochemicals, including but not limited to spraying, brushing, dressing, dripping, coating, dipping, spreading, applying as small droplets, a mist or an aerosol. As non-limiting examples, a targeting agent hereof can be used to deliver and retain an agrochemical or a combination of agrochemicals to the foliage of a field grown crop, it can be used to deliver and retain an agrochemical or a combination of agrochemicals to the roots of a crop propagated by hydroculture, it can be used to deliver and retain an agrochemical or a combination of agrochemicals to harvested plant parts (e.g., fruits, flowers or seeds) as a post-harvest treatment, it can be used to deliver and retain an agrochemical or a combination of agrochemicals to living or dead plant material present in the soil upon preparation of arable land, which is particularly useful in combination with no tilling agricultural practices, or it can be used to deliver and retain an agrochemical to a substrate placed in the vicinity of a rhizosphere to achieve distribution and prolonged retention of agrochemicals throughout the rhizosphere. One particularly advantageous aspect hereof is that it allows, by suitably choosing the combination of targeting agent and agrochemical, or combination of agrochemicals to formulate the same active substance for a variety of different uses, for example, on different plant species or parts of plants, for different environmental conditions (type of soil, amount of rainfall and other weather conditions, or even different seasonal conditions) and different end-uses (for example, in the field, in greenhouses, in gardens, in hydroponic culture systems, for possibly environmental dependent quick, delayed or slow release use, for household use and for use by pest control operators). Thus, by the use of the targeting agent to deliver and retain the agrochemical, it is possible, starting from active agrochemical substances or agrochemical foiinulations with proven efficacy, that are environmentally acceptable, to provide a range of different and improved plant protection products or agents or other agrochemical products that are tailored for desired or intended end use. As a non-limiting example, a broad spectrum herbicide can be made plant species specific by delivering it using a targeting agent comprising a plant species specific binding domain; on the other hand, delivering the same herbicide using a targeting agent comprising a binding domain that has a broad spectrum specificity can help to reduce the amounts of herbicide needed to exert its desired action. Also, undesired off-target activity of an agrochemical, e.g., versus beneficial insects, can be avoided by delivering the agrochemical using a targeting agent comprising a binding domain that is highly specific for the targeted crop or for specific parts of the targeted crop.

Preferably, the agrochemical or combination of agrochemicals is selected from the groups consisting of herbicides, insecticides, fungicides, nematicides, biocides, fertilizers, safeners, micro-nutrients and plant growth regulating compounds.

Preferably, the method of delivery and retention of an agrochemical or combination of agrochemicals results in improved deposition of the agrochemical or combination of agrochemicals on the plant or plant part. "Improved deposition," as used herein, means that either the quantity of the agrochemical or combination of agrochemicals that is bound to the plant or plant part is increased and/or that the distribution of the agrochemical or combination of agrochemicals is divided over the plant or plant part either more equally or more concentrated in function of the specificity of the binding domain comprised in the targeting agent, when compared to the same agrochemical or combination of agrochemicals applied without the use of any targeting agent.

In one embodiment, the agrochemical or combination of agrochemicals is bound on or comprised in a carrier, preferably, a microcarrier as defined earlier. This may, for example, be particularly advantageous for an agrochemical or combination of agrochemicals that are volatile or rapidly degradable by environmental factors such as the presence of moisture or UV-irradiation, or that pose a considerable toxicity hazard for the person handling the agrochemical or combination of agrochemicals. In one specific embodiment, functional groups on the carrier may be bound to a linking agent or spacer, which is on its turn bound to a targeting agent as defined above.

A fourth aspect hereof is a composition, comprising at least (i) one targeting agent comprising at least one binding domain hereof and (ii) an agrochemical or combination of agrochemicals.

The targeting agent(s) comprised in the composition may either be a "mono-specific" targeting agent or a "multi-specific" targeting agent. By a "mono-specific" targeting agent is meant a targeting agent that comprises either a single binding domain, or that comprises two or more different binding domains that each are directed against the same antigen present at or in the same binding site or that form the binding site. Thus, a mono-specific targeting agent is capable of binding to a single binding site, either through a single binding domain or through multiple binding domains. By a "multi-specific" targeting agent is meant a targeting agent that comprises two or more binding domains that are each directed against different antigens present at or in a binding site or that form the binding site. Thus, a "bi-specific" targeting agent is capable of binding to two different binding sites or antigens present at or in a binding site or that form the binding site; a "tri-specific" targeting agent is capable of binding to three different antigens present at or in a binding site or that form the binding site; and so on for "multi-specific" targeting agents. Also, in respect of the targeting agents described herein, the term "monovalent" is used to indicate that the targeting agent comprises a single binding domain; the term "bivalent" is used to indicate that the targeting agent comprises a total of two single binding domains; the term "trivalent" is used to indicate that the targeting agent comprises a total of three single binding domains; and so on for "multivalent" targeting agents. Accordingly, in one aspect, the above composition hereof comprises two or more identical or different targeting agents, by which is meant two or more targeting agents that, for identical targeting agents, each bind to identical or different antigens present at or in the same binding site, whereas for different targeting agents, at least one binds to different antigens present at or in the same binding site or in different binding sites.

Preferably, the targeting agent(s) comprised in the composition, comprise at least one binding domain that binds to a binding site or to an antigen comprised in such binding site, present in or on one or more particular parts of a plant, preferably of an intact living plant. Preferably, the parts of the plant, more preferably, of the intact living plant, are selected from the group consisting of leaves, stems, roots, fruits, cones, flowers, bulbs or tubers. More preferably, the parts of the intact living plant are selected from the group consisting of leaves, stems or roots. More preferably, the targeting agent(s) comprised in the composition, comprise at least one binding domain that binds to a binding site or to an antigen comprised in such binding site, on the surface of the intact living plant. Preferably, the surface of the intact living plant is the surface of a part of the intact living plant, selected from the group consisting of leaf surface, stem surface, root surface, fruit surface, cone surface, flower surface, bulb surface or tuber surface; even more preferably, the surface of the intact living plant is the surface of a part of the intact living plant, selected from the group consisting of root surface, stem surface and leaf surface.

Preferably, the targeting agent(s) comprised in the composition, comprise at least one binding domain that binds to a binding site, or to an antigen comprised in such binding site, in or on a particular structure of the plant, preferably the intact living plant or in or on a particular structure of a particular part of the plant, preferably the intact living plant; more preferably, in or on a particular structure involved or implicated to be involved in transport of nutrients, agrochemicals or other chemicals into the plant and/or involved or implicated to be involved in plant defense. Preferably, the particular structure is selected from the group consisting of trichomes, stomata, lenticels, thorns, spines, root hairs, cuticle and wax layer, even more preferably, the particular structure is selected from the group consisting of trichomes, stomata and cuticle. In one embodiment, the targeting agent(s) comprised in the composition, comprise at least one binding domain that binds to a binding site, or to an antigen comprised in such binding site, in or on plant trichomes. In another embodiment, the targeting agent(s) comprised in the composition, comprise at least one binding domain that binds to a binding site, or to an antigen comprised in such binding site, in or on stomata. In yet another embodiment, the targeting agent(s) comprised in the composition, comprise at least one binding domain that binds to a binding site, or to an antigen comprised in such binding site, in or on plant cuticle.

In yet another embodiment, the targeting agent(s) comprised in the composition, comprise at least one binding domain that binds to gum arabic. In preferred embodiment, the targeting agent(s) comprised in the composition, comprise at least one binding domain that binds to lectins, lectin-like domains, extensins, or extensin-like domains; more preferably, the binding domain is binding potato lectin. Preferably, the targeting agent(s) comprised in the composition, comprise at least one binding domain that comprises four framework regions and three complementarity-determining regions, or any suitable fragment thereof (which will then usually contain at least some of the amino acid residues that form at least one of the complementarity-determining regions); more preferably, one or more of the binding domains comprised in the targeting agent is derived from a heavy chain camelid antibody, even more preferably, one or more of the binding domains comprised in the targeting agent comprises a VHH sequence. Still even more preferably, VHH comprises two disulphide bridges. Most preferably, VHH comprises, preferably, consists of a sequence selected from the group consisting of SEQ ID NO:1-SEQ ID NO:42 (3A2, 3B4, 3B7, 3D10, 3D2, 3D8, 3E6, 3F5, 3F7, 3F9, 3G2, 3G4, 3H10, 3H8, 4A1, 5B5, 5B6, 5C4, 5C5, 5D4, 5E5, 5F5, 5G2, 5G5, 5H5, 7A2, 7C2, 7D2, 7E1_1, 7F1, 8B10, 8B12, 9A1, 9B5, 9C4, 9D5, 9E1, 9E4, 9F4, 9H1, 9H2 and 12H4), or any suitable fragment thereof (which will then usually contain at least some of the amino acid residues that form at least one of the complementarity-determining regions) or homologues thereof.

In the composition hereof, the agrochemical or combination of agrochemicals are preferably selected from the group consisting of herbicides, insecticides, fungicides, nematicides, biocides, fertilizers, safeners, micro-nutrients or plant growth regulating compounds.

In the composition hereof, the agrochemical or combination of agrochemicals may be in a liquid, semi-solid or solid form and, for example, be maintained as an aerosol, flowable powder, wettable powder, wettable granule, emulsifiable concentrate, suspension concentrate, microemulsion, capsule suspension, dry microcapsule, tablet or gel or be suspended, dispersed, emulsified or otherwise brought in a suitable liquid medium (such as water or another suitable aqueous, organic or oily medium) for storage or application onto a plant. Optionally, the composition further comprises one or more further components such as, but not limited to diluents, solvents, adjuvants, surfactants, wetting agents, spreading agents, oils, stickers, thickeners, penetrants, buffering agents, acidifiers, anti-settling agents, anti-freeze agents, photo-protectors, defoaming agents, biocides and/or drift control agents or the like, suitable for use in the composition hereof.

In one embodiment, the agrochemical or combination of agrochemicals is bound on or otherwise comprised in a carrier. In the case of a combination of agrochemicals, each individual agrochemical may be bound on or otherwise comprised in an individual carrier, or a suitable combination of agrochemicals may be jointly bound on or otherwise comprised in one carrier. As an alternative to the use of a carrier, the agrochemical or combination of agrochemicals may also be provided in the form of (small) particles which are provided with a suitable coating or (outside) layer to which the targeting agent is coupled or can bind and which may also serve to stabilize or improve the physical integrity or stability of the particles. As another alternative, the agrochemical or combination of agrochemicals may be suitably mixed with an excipient or binder to which the targeting agent is coupled or can bind, and which may again also serve to stabilize or improve the physical integrity or stability of the particles. Such coated or composite particles are preferably in the form of a slurry, wet cake or free-flowable powder, tablet, capsule or liquid concentrate (such as an emulsion, suspension or dispersion).

In one embodiment, the composition hereof is for agrochemical use. "Agrochemical use," as used herein, not only includes the use of agrochemicals as defined above (for example, pesticides, growth regulators, nutrients/fertilizers, repellants, defoliants, etc.) that are suitable and/or intended for use in field grown crops (e.g., agriculture), but also includes the use of agrochemicals as defined above (for example, pesticides, growth regulators, nutrients/fertilizers, repellants, defoliants, etc.) that are meant for use in greenhouse grown crops (e.g., horticulture/floriculture) or hydroponic culture systems and even the use of agrochemicals as defined above that are suitable and/or intended for non-crop uses such as uses in private gardens, household uses (for example, herbicides or insecticides for household use), or uses by pest control operators (for example, weed control, etc.).

Based on the teaching set out in the present specification, and, for example, depending on the agrochemical(s) to be delivered, on the part(s) to the plant to which the agrochemical(s) is to be delivered, and the intended agrochemical action of the composition hereof (and/or the agrochemical(s) included therein), the skilled person will be able to suitably select the specific binding domains/targeting agent that can/should be present in the composition hereof (as well as the other components of the composition, such as the carrier, the agrochemical and the agrochemical form/formulation) in order to achieve the desired/intended agrochemical action. Thus, with advantage, based on the disclosure herein, it is possible for the skilled person to suitably select a suitable combination of binding domain(s)/targeting agent(s), agrochemical(s), carrier, further components of the composition and the agrochemical foinilformulation of the composition in order to achieve the intended/desired agrochemical action. In this respect, it should be noted that, as currently contemplated, and although it is foreseen that some such combinations will be more efficacious and/or more preferred than others, there will likely be multiple such combinations possible that will give the intended/desired agrochemical action to the more or less same degree. This also allows the skilled person to take into account other (secondary) factors when selecting the combination to be used, such as the specific crop(s) to be protected, the prevalent field, soil, weather and/or other environmental conditions, the way that composition is preferably applied, the environment in which it is applied (field, greenhouse, etc.), the desired persistence and/or other factors that may influence the choice of an agrochemical composition for a specific application.

For example, and without limitation, when the composition hereof is intended to bind to one or more specific parts of the plant, the targeting agent (i.e., the one or more binding domains present therein) are preferably directed towards one or more binding sites (as defined herein) that are present (i.e., in a sufficient amount) in/on the part(s) of the plant (it also being possible that such binding site(s) are present in/on the part(s) of the plant in a larger amount(s)/to a greater degree than on other part(s) of the plant, i.e., so as to provide a binding domain/targeting agent/composition hereof that can preferentially bind to the intended/desired part(s) of the plant compared to one or more other parts of the plant); and compositions hereof that comprise such binding domains/targeting agents (i.e., such that the compositions are directed towards binding sites present in the desired part(s) of the plant and, preferably, such that they can bind preferentially to the desired part(s) of the plant) faun some specific but non-limiting aspects hereof. For example, and without limitation:

for a composition hereof that is intended to bind to the leaves of a plant, the binding domains and/or targeting agent may be directed against one or more of the following binding sites on (the leaves of) a plant: cutin, cuticular waxes, arabinogalactan-proteins or lipid transfer proteins;

for a composition hereof that is intended to bind to the roots of a plant, the binding domains and/or targeting agent may be directed against one or more of the following binding sites on (the roots of) a plant: extensins or pectins;

for a composition hereof that is intended to bind to the stem of a plant, the binding domains and/or targeting agent may be directed against one or more of the following binding sites on (the stem of) a plant: lignins, extensins or excretion products; and each such composition hereof forms a specific, but non-limiting aspect hereof.

A fifth aspect hereof is a composition, comprising at least (i) one targeting agent comprising at least one binding domain hereof and (ii) a carrier.

The targeting agent(s) comprised in the composition may either be mono-specific targeting agents or multi-specific targeting agents and may be either monovalent targeting agents or multivalent targeting agents. Accordingly, in one aspect, the above composition hereof comprises two or more identical or different targeting agents, by which is meant two or more targeting agents that, for identical targeting agents, each bind to identical or different antigens present at or in the same binding site, whereas for different targeting agents, at least one binds to different antigens present at or in the same binding site or in different binding sites.

In one specific embodiment, which is preferred but non-limiting, the carrier is such that it allows the composition hereof to be suitably applied to the intended site of action, and/or such that it allows the composition hereof to be formulated such that it can be suitably applied to the intended site of action; using any suitable or desired manual or mechanical technique such as spraying, brushing, dripping, dipping, coating, spreading, applying as small droplets, a mist or an aerosol, etc. Examples of such techniques, of compositions hereof that are suitable for use in such techniques, and of methods for making and formulating such compositions hereof will be clear to the skilled person based on the disclosure herein. Preferably, the carrier is such that one or more active substances can be incorporated, encapsulated or included into the carrier, e.g., as a nanocapsule, microcapsule, nanosphere, micro-sphere, liposome or vesicle. Even more preferably, the carrier is such that upon such incorporation, encapsulation, embedding or inclusion, the complex thus obtained can be suspended, dispersed, emulsified or otherwise brought into a suitable liquid medium (such as water or another suitable aqueous, organic or oily medium) so as to provide a (concentrated) liquid composition hereof that has a stability that allows the composition hereof to be suitably stored or (where necessary after further dilution) applied to the intended site of action. Even more preferably, the carrier is such that the composition hereof can be transported and/or stored prior to final use, optionally (and usually preferably) as a suitable liquid concentrate, dry powder, tablet, capsule, slurry or "wet cake," which can be suitably diluted, dispersed, suspended, emulsified or otherwise suitably reconstituted by the end user prior to final use (and such concentrates form a further aspect hereof). Carriers, preferably microcarriers, suitable for this purpose (and methods for absorbing, encapsulating, embedding, etc., the active principles therein) will be clear to the skilled person based on the disclosure herein and/or may be commercially available. Some non-limiting examples include solid or semi-solid microspheres or granulates in which the active ingredients are embedded or absorbed in a suitable matrix material or microcapsules comprising a shell material that surround a core that contains the active ingredient (i.e., encapsulated within the microcapsule).

Preferably, the carriers are such that they have immediate, delayed, gradual, triggered or slow release characteristics, for example, over several minutes, several hours, several days or several weeks. Also, the carriers may be made of materials (e.g., polymers) that rupture or slowly degrade (for example, due to prolonged exposure to high or low temperature, high or low pH, sunlight, high or low humidity or other environmental factors or conditions) over time (e.g., over minutes, hours, days or weeks) or that rupture or degrade when triggered by particular external factors (such as high or low temperature, high or low pH, high or low humidity or other environmental factors or conditions) and so release the active agent from the microcapsule. The carrier is also, preferably, such that the agrochemicals are released from the carrier when the composition hereof is applied to the intended site of action, i.e., at a rate that is sufficient to provide the desired action of the agrochemicals during the desired period of time (e.g., the time between two applications of the composition hereof).

In one particular embodiment, the carrier, preferably the microcarrier, may be composed of polymer materials, such as, for example, poly-urethane, poly-urea, poly-amide, poly-ethylene, polyethylene-glycol, polyvinyl alcohols, melamine, urea/formaldehyde, acrylic polymers, nylon, vinyl acetate or siloxane polymers or—optionally (and usually preferably) for agrochemical purposes—biodegradable polymers (such as, for example, agar, gelatin, alginates, gums, pectins, poly-alcohols such as cetyl-alcohol, oily substances such as hydrogenated palm oil or soybean oil, starches, waxes, etc. Alternatively, and although this is usually less preferred, non-biodegradable materials may be used such as poly-methylacrylates, poly-ethersulfones, metal oxides, carbon structures, etc.

Preferably, the carrier is selected from the group consisting of nanocapsules, nanospheres, microcapsules, microspheres, polymer particles, particles made from artificially lignified cellulose, composite gel particles, weak ionic resin particles, microbial cells or fragments thereof. More preferably, the carrier is selected from the group consisting of microcapsules, microspheres or polymer particles. Most preferably, the carrier is a microcapsule.

In one embodiment, the targeting agent(s) comprised in the composition, comprise at least one binding domain that comprises four framework regions and three complementarity-determining regions, or any suitable fragment thereof (which will then usually contain at least some of the amino acid residues that form at least one of the complementarity-determining regions); more preferably, one or more of the binding domains comprised in the targeting agent is derived from a heavy chain camelid antibody, even more preferably, one or more of the binding domains comprised in the targeting agent comprises a VHH sequence. Still even more preferably, VHH comprises two disulphide bridges. Most preferably, VHH comprises, preferably, consists of a sequence selected from the group consisting of SEQ ID NO:1-SEQ ID NO:42 (3A2, 3B4, 3B7, 3D10, 3D2, 3D8, 3E6, 3F5, 3F7, 3F9, 3G2, 3G4, 3H10, 3H8, 4A1, 5B5, 5B6, 5C4, 5C5, 5D4, 5E5, 5F5, 5G2, 5G5, 5H5, 7A2, 7C2, 7D2, 7E1_1, 7F1, 8B10, 8B12, 9A1, 9B5, 9C4, 9D5, 9E1, 9E4, 9F4, 9H1, 9H2 and 12H4), or any suitable fragment thereof (which will then usually contain at least some of the amino acid residues that form at least one of the complementarity-determining regions) or homologues thereof.

In another embodiment, the targeting agent and the carrier comprised in the composition hereof are coupled to each other. Preferably, the one single targeting agent or multiple targeting agents are coupled to the carrier by affinity binding or by covalent binding. More preferably, the one single targeting agent or multiple targeting agents, are coupled to the carrier by covalent binding. Preferably, the one single targeting agent or multiple targeting agents are coupled, preferably covalently coupled, to the carrier by the use of a functional group present on the outer surface of the carrier. Preferably, the binding domain comprised in the targeting agent(s) is coupled, preferably covalently coupled, to the carrier. Alternatively, the one single targeting agent or multiple targeting agents are coupled, preferably covalently coupled, to the carrier via a moiety that is not the binding domain comprised in the targeting agent.

In yet another embodiment, the carrier is coupled to and/or comprises at least one agrochemical as defined above. Preferably, the agrochemical is selected from the group consisting of herbicides, insecticides, fungicides, nematicides, biocides, fertilizers, micro-nutrients, safeners or plant growth regulating compounds. In this embodiment, the composition is for agrochemical use.

The carrier with the one or more targeting agents bound, coupled or otherwise attached thereto or associated therewith may be dissolved, emulsified, suspended or dispersed or otherwise included into a suitable liquid medium (such as water or another aqueous, organic or oily medium) so as to provide a (concentrated) solution, suspension, dispersion or emulsion that is suitable for storage.

For example, when the composition hereof is intended for agrochemical use, the composition hereof may be in a liquid, semi-solid or solid form that is suitable for spraying, such as a solution, emulsion, suspension, dispersion, aerosol, flowable powder or any other suitable foiin. In particular, such a composition hereof for agrochemical use may comprise a microcapsule, microsphere, nanocapsule, nanosphere, liposomes or vesicles, etc., in which the one or more agrochemicals are suitably encapsulated, enclosed, embedded, incorporated or otherwise included; and one or more targeting agents that each comprise one or more binding domains for binding to one or more antigens present at or in the binding site or that form the one or more binding sites on a plant or parts of a plant, such as a leaf, stem, flower, fruit, bulb or tuber of a plant).

A sixth aspect hereof is a method for delivery of an agrochemical or a combination of agrochemicals to a plant, the method comprising at least one application of a composition hereof to the plant.

"One application," as used herein, means a single treatment of a plant or plant part. According to this method, either the composition hereof is applied as such to the plant or plant part, or the composition is first dissolved, suspended and/or diluted in a suitable solution before being applied to the plant. The application to the plant is carried out using any suitable or desired manual or mechanical technique for application of an agrochemical or a combination of agrochemicals, including but not limited to spraying, brushing, dressing, dripping, dipping, coating, spreading, applying as small droplets, a mist or an aerosol. Upon such application to a plant or part of a plant, the composition can bind at or to the binding site (or to one or more antigens present at or in the binding site or that form the binding site) via one or more binding domains that form part of the targeting agent(s) comprised in the composition, preferably in a targeted manner. Thereupon, the agrochemicals are released from the carrier (e.g., due to degradation of the carrier or passive transport through the wall of the carrier) in such a way that they can provide the desired agrochemical action(s). A particular advantage of delivering an agrochemical or combination of agrochemicals to a plant using a composition hereof is that it may lead to an improved deposition (as defined earlier) of the agrochemical or combination of agrochemicals on the plant or plant part and/or an increased resistance of the agrochemical or combination of agrochemicals against loss due to external factors such as rain, irrigation, snow, hail or wind.

In one embodiment, delivering an agrochemical or combination of agrochemicals to a plant using a composition hereof results in improved rainfastness of the agrochemical or combination of agrochemicals. "Improved rainfastness," as used herein, means that the percentage loss of agrochemical or combination of agrochemicals, calculated before and after rain, is smaller when the agrochemical or combination of agrochemicals is applied in a composition hereof, compared with the same agrochemical or combination of agrochemicals comprised in a comparable composition, without any targeting agent. A "comparable composition," as used herein, means that the composition is identical to the composition hereof, apart from the absence of the targeting agent used in the composition hereof.

In one embodiment, a suitable dose of the agrochemical or combination of agrochemicals comprised in a composition hereof is applied to the plant or plant part. A "suitable dose," as used herein, means an efficacious amount of active substance of the agrochemical comprised in the composition.

Preferably, the method comprises the application of a meaningfully reduced dose of an agrochemical or combination of agrochemicals to the plant, to obtain similar beneficial effects for the agrochemical or combination of the agrochemicals, as compared with the application of the same agrochemical or combination of agrochemicals comprised in a comparable composition, as defined above, without any targeting agent. The meaningful reduction is obtained by directing the agrochemical to the plant using targeting agents hereof. Alternatively, the method comprises an application of a suitable dose, wherein the application frequency is meaningfully reduced, to obtain similar beneficial effects for the agrochemical, compared with the frequency of application of the same dose of an encapsulated composition of the agrochemical lacking the presence of a targeting agent hereof. Even more preferably, the method comprises an application wherein the suitable dose as well as the application frequency are both significantly reduced to obtain similar beneficial effects for the agrochemical, compared with the suitable dose and application frequency of a an encapsulated composition of the agrochemical lacking the presence of a targeting agent hereof.

A seventh aspect hereof is a method for protecting a plant against external (biotic or abiotic) stress and/or to modulate the viability, growth or yield of a plant or plant parts and/or to modulate gene expression in a plant or plant part resulting in alteration of (levels of) plant constituents (such as proteins, oils, carbohydrates, metabolites, etc.), the method comprising at least one application of a composition hereof. If needed, the composition is dissolved, suspended and/or diluted in a suitable solution. "Protecting a plant," as used here, is the protection of the plant against any stress; the stress may be biotic stress, such as, but not limited to, stress caused by weeds, insects, rodents, nematodes, mites, fungi, viruses or bacteria, or it may be abiotic stress, such as but not limited to drought stress, salt stress, temperature stress or oxidative stress.

Preferably, the method comprises the application of a meaningfully reduced dose of an agrochemical or combination of agrochemicals to the plant, to obtain similar beneficial effects for the agrochemical or combination of the agochemicals, as compared with the application of the same agrochemical or combination of agrochemicals comprised in a comparable composition, as defined earlier, without any targeting agent. The meaningful reduction is obtained by directing the agrochemical to the plant using targeting agents hereof. Alternatively, the method comprises an application of a suitable dose, wherein the application frequency is meaningfully reduced, to obtain similar beneficial effects for the agrochemical, compared with the frequency of application of the same dose of an encapsulated composition of the agrochemical lacking the presence of a targeting agent hereof. Even more preferably, the method comprises an application wherein the suitable dose as well as the application frequency are both significantly reduced to obtain similar beneficial effects for the agrochemical, compared with the suitable dose and application frequency of an encapsulated agrochemical lacking the presence of a targeting agent hereof.

An eighth aspect hereof is a method for manufacturing a specifically targeting agrochemical carrier, the method comprising (a) packing an agrochemical in or on(to) a carrier and (b) attaching at least one targeting agent hereof to the carrier.

"Packing," as used herein, means incorporating, including, immobilizing, adsorbing, absorbing, binding, encapsulating, embedding, attaching, admixing, anchoring or comprising. Methods for packing an agrochemical, as defined above, in or on(to) a carrier are known to the person skilled in the art and include, without limitation, drip-casting, extrusion granulation, fluid bed granulation, co-extrusion, spray drying, spray chilling, atomization, addition or condensation polymerization, interfacial polymerization, in situ polymerization, coacervation, spray encapsulation, cooling melted dispersions, solvent evaporation, phase separation, solvent extraction, sol-gel polymerization, high or low shear mixing, fluid bed coating, pan coating, melting, passive or active absorption or adsorption. In one preferred, but not limiting, embodiment, an agrochemical is packed into a microcarrier using suitable microencapsulation techniques, such as interfacial polymerization, in situ polymerization, coacervation, spray encapsulation, cooling melted dispersions, solvent evaporation, phase separation, solvent extraction or sol-gel polymerization. Preferred, but non-limiting examples of suitable materials for producing such microcarriers are materials such as alginates, agar, gelatin, pectins, gums, hydrogenated oils, starches, waxes, polyalcohols, poly-urea, poly-urethane, poly-amide, melamine, urea/formaldehyde, nylon and other (optionally and usually preferred biodegradable or inert) polymers. More preferably, at least one functional group is present at the outer surface of the microcarrier.

At least one targeting agent hereof is attached to the carrier, either by a covalent bond, by hydrogen bonds, by dipole-dipole interactions, by weak Van der Waals forces or by a combination of any of the foregoing. Attachment of the targeting agent to the carrier may be performed while packing the agrochemical in or on(to) the carrier, it may be performed subsequent to packing of the agrochemical in or on(to) the carrier or it may be performed only at the time the agrochemical containing carrier is dissolved in a suitable solution for application. Suitable processes for attaching the targeting agent to a carrier will be clear to the person skilled in the art. In one embodiment, the targeting agent and the carrier are coupled to each other. Preferably, the targeting agent(s) are coupled to the carrier by affinity binding or by covalent binding. More preferably, the targeting agent(s) are coupled to the carrier by covalent binding. Preferably, the targeting agent(s) are coupled, preferably covalently coupled, to the carrier by the use of a functional group present on the outer surface of the carrier. Preferably, the binding domain comprised in the targeting agent(s) is coupled, preferably covalently coupled, to the carrier. Alternatively, the targeting agent(s) are coupled, preferably covalently coupled, to the carrier via a moiety that is not the binding domain comprised in the targeting agent. In one embodiment, the process for attaching the targeting agent(s) to a carrier comprises (a) reacting a linking agent with a carrier, and (b) reacting at least one targeting agent with the linking agent.

A ninth aspect hereof is a process for attaching a targeting agent hereof to a carrier, comprising (a) reacting a linking agent with a carrier, and (b) reacting the targeting agent with the linking agent. "Reacting," as used herein, means that the linking agent is placed in conditions allowing the binding of the linking agent to the carrier and/or the targeting agent.

A tenth aspect hereof is a specifically targeting agrochemical carrier, obtained by the above described method. "Specifically targeting," as used herein, means that the carrier can bind specifically to a binding site on a plant or on a plant part, through at least one targeting agent hereof, which is attached, preferably coupled, most preferably covalently bound, to the carrier.

A last aspect hereof is the use of any binding domain hereof to isolate amino acid sequences that are responsible for specific binding to the binding site or to an antigen comprised in the binding site and to construct artificial binding domains based on the amino acid sequences. Indeed, in the binding domains hereof, the framework regions and the complementarity-determining regions are known, and the study of derivatives of the binding domain, binding to the same binding site or antigen comprised in the binding site, will allow deducing the essential amino acids involved in binding the binding site or antigen comprised in the binding site. This knowledge can be used to construct a minimal binding domain and to create derivatives thereof.

BRIEF DESCRIPTION OF THE DRAWINGS

FIG. 1: Binding domains (VHH) binding to leaf surface.

FIG. 1A: VHH3E6 5 μg/ml in PBS binding to native potato leaf surface. Detection with anti-histidine antibodies directly conjugated with Alexa-488 fluorescent dye. VHH 3E6 is binding leaf surface, stomata, glandular trichomes, and leaf hairs.

FIG. 1B: VHH3E6 5 μg/ml in PBS binding to native potato leaf surface. Detection with anti-histidine antibodies directly conjugated with Alexa-488 fluorescent dye; Imaging with a Leica SP5 confocal microscope system. VHH 3E6 is binding leaf surface, stomata, glandular trichomes, and leaf hairs.

FIG. 1C: VHH5D4 5 μg/ml in PBS binding to native potato leaf surface. Detection with anti-histidine antibodies directly conjugated with Alexa-488 fluorescent dye. VHH 5D4 is binding leaf surface, stomata, glandular trichomes, and leaf hairs.

FIG. 1D: CBM3a 5 μg/ml in PBS binding to wounded plant tissue on the edge of a potato leaf disc. Detection with anti-histidine antibodies directly conjugated with Alexa-488 fluorescent dye. CBM3a is not binding leaf surface, stomata, glandular trichomes, or leaf hairs, but only binding to wounded plant tissue on the edge of a potato leaf disc that is exposed from preparing the sample by punching the leaf.

FIG. 1E: Without primary antibody (plain PBS) on native potato leaf surface. Incubation with anti-histidine antibodies directly conjugated with Alexa-488 fluorescent dye.

FIG. 1F: VHH3E6 5 μg/ml in PBS binding to native black nightshade leaf surface. Detection with anti-histidine antibodies directly conjugated with Alexa-488 fluorescent dye. VHH 3E6 is binding leaf surface, glandular trichomes, and leaf hairs.

FIG. 1G: VHH3E6 5 μg/ml in PBS binding to native grass leaf surface. Detection with anti-histidine antibodies directly conjugated with Alexa-488 fluorescent dye. VHH 3E6 is binding to leaf surface and wounded plant tissue on the edge of a potato leaf disc that is exposed from preparing the sample by punching the leaf.

FIG. 2: Binding of binding domains (VHH) to intact living plant

FIG. 2A: VHH3E6 5 μg/ml in PBS binding to an intact living plant. Leaves attached to a potato pot plant were submerged in a solution of VHH 3E6. Leaves were sampled. Detection with anti-histidine antibodies directly conjugated with Alexa-488 fluorescent dye. VHH 3E6 is binding leaf surface, stomata, glandular trichomes, and leaf hairs.

FIG. 2B: VHH3E6 5 μg/ml in PBS binding to an intact living plant. Leaves attached to a potato pot plant were submerged in a solution of VHH 3E6. Leaves were sampled. Detection with anti-histidine antibodies directly conjugated with Alexa-488 fluorescent dye. Excerpt from whole leaf labeling. VHH 3E6 is binding leaf surface, stomata, glandular trichomes, and leaf hairs.

FIG. 3: Coupling of binding domains to microcapsules

FIG. 3A: Microcapsules with coupled VHH3E6 through one-step EDC coupling chemistry. Coupled microcapsules were labeled with anti-histidine antibodies directly conjugated with Alexa-488 fluorescent dye. Imaging with a Leica SP5 confocal microscope system. VHH 3E6 is coupled to the microcapsule surface through one-step coupling chemistry.

FIG. 3B: Microcapsules with coupled VHH3E6 through two-step EDC/NHS coupling chemistry. Coupled microcapsules were labeled with anti-histidine antibodies directly conjugated with Alexa-488 fluorescent dye. Imaging with a Leica SP5 confocal microscope system. VHH 3E6 is coupled to the microcapsule surface through two-step EDC/NHS coupling chemistry.

FIG. 3C: Microcapsules incubated with VHH3E6 without covalent coupling. Passively adsorbed VHH were labeled with anti-histidine antibodies directly conjugated with Alexa-488 fluorescent dye. Imaging with a Leica SP5 confocal microscope system. A minor fraction of VHH 3E6 is passively adsorbed to the microcapsule surface.

FIG. 3D: Control condition with microcapsules not incubated with VHH but only with anti-histidine antibodies directly conjugated with Alexa-488 fluorescent dye. Imaging with a Leica SP5 confocal microscope system. A minor fraction of VHH 3E6 is passively adsorbed to the microcapsule surface.

FIG. 4: Binding and retention of microcapsules to leaf surface. Leaf disc binding assay on native potato leaf discs with microcapsules containing a fluorescent tracer molecule. Binding and retention of microcapsules coupled with specific plant-binding VHH, coupled with unrelated control VHH, or blank microcapsules is compared. Nine-fold more microcapsules coupled with specific VHH are binding and retained on potato leaf discs compared to blank microcapsules.

FIG. 5: Reduction of dosis using microcapsules coupled with targeting agents. Leaf disc binding assay on native potato leaf discs with microcapsules containing a fluorescent tracer molecule. Binding and retention of microcapsules in different concentrations and coupled with specific plant-binding VHH, coupled with unrelated control VHH, or blank microcapsules is compared. Up to eight-fold more microcapsules coupled with specific VHH are binding and retained on potato leaf discs compared to blank microcapsules.

DETAILED DESCRIPTION OF THE DISCLOSURE

Examples

Example 1

Generation and Selection of VHH

Immunization of Llamas with Gum Arabic, Potato Leaf Homogenate, or Wheat Leaf Homogenate A solution of gum arabic was prepared by weighing 5 g of gum arabic from acacia tree (Sigma) and dissolving in 50 ml water. Bradford protein assay was used to determine the total protein concentration. Aliquots were made, stored at −80° C., and used for immunization.

Homogenized leaves from potato plants (*Solanum tuberosum* variety Desiree) or wheat plants (*Triticum aestivum* variety Boldus) were prepared by freezing leaves in liquid nitrogen and homogenizing the leaves with mortar and pestle until a fine powder was obtained. Bradford protein assay was used to determine the total protein concentration. Aliquots were made, stored at −80° C., and suspensions were used for immunization.

Llamas were immunized at weekly intervals with six intramuscular injections of gum arabic, homogenized potato leaves, or homogenized wheat leaves, according to standard procedures. Two Llamas, "404334" and "Lahaïana," were immunized with gum arabic. Three llamas, "407928," "Chilean Autumn," and "Niagara," were immunized with homogenized potato leaves and another two llamas, "33733" and "Organza," were immunized with homogenized wheat leaves. Llamas "404334," "407928," and "33733" were immunized using Adjuvant LQ (Gerbu), and llamas "Lahaïana," "Chilean Autumn," "Niagara" and "Organza" were immunized using Freund's Incomplete Adjuvant (FIA). Doses for immunization of llama "404334" were 350 µg for each day 0, 7, 14, 21, 28, 35, and peripheral blood lymphocytes (PBL) were collected at day 40. Doses for immunizations of llamas "407928" and "33733" were 1 mg for each day 0, 7, 14, 21, 28, 36, and PBL were collected at day 40. At time of PBL collection at day 40, sera of llamas "404334," "407928," and "33733" were collected. Doses for immunizations of llamas "Lahaïana," "Chilean Autumn," "Niagara," and "Organza" were 100 µg for day 0, and 50 µg for days 7, 14, 21, 28, and 35. At day 0, day 25, and at time of PBL collection at day 38, sera of llamas "Lahaïana," "Chilean Autumn," "Niagara," and "Organza" were collected.

Library Construction—

From each immunized llama a separate VHH library was made. RNA was isolated from peripheral blood lymphocytes, followed by cDNA synthesis using random hexamer primers and Superscript III according to the manufacturer's instructions (Invitrogen). A first PCR was performed to amplify VHH and VH using a forward primer mix [1:1 ratio of call001 (5'-gtcctggctgctcttctacaagg-3' (SEQ ID NO:43)) and call001b (5'-cctggctgctcttctacaaggtg-3' (SEQ ID NO:44))] and reverse primer call002 (5'-ggtacgtgctgttgaactgttcc-3' (SEQ ID NO:45)). After isolation of the VHH fragments a second PCR was performed using forward primer A6E (5'-gatgtgcagctgcaggagtctggrggagg-3' (SEQ ID NO:46)) and reverse primer 38 (5'-ggactagtgcggccgctggagacggt-gacctgggt-3' (SEQ ID NO:47)). The PCR fragments were digested using PstI and Eco91I restriction enzymes (Fermentas), and ligated upstream of the pIII gene in vector pMES4 (GenBank: GQ907248.1). The ligation products were ethanol precipitated according to standard protocols, resuspended in water, and electroporated into TG1 cells. Library sizes ranged from 1E+08 to 6E+08 independent clones. Single colony PCR on randomly picked clones from the libraries was performed to assess insert percentages of the libraries. All libraries had >90% insert percentages except for the library from immunized llama "Organza" which had an insert percentage of 80%. Libraries were numbered 25, 27, 28, 29, 30, 31, 32 for llamas "404334," "407928," "33733," "Chilean Autumn," "Lahaïana," "Niagara," and "Organza," respectively. Phage from each of the libraries were produced using VCSM13 helper phage according to standard procedures.

Phage Selections Against Gum Arabic, Plant Epidermal Extracts, or Whole Leaves.

A solution of gum arabic was prepared by weighing 5 g of gum arabic and dissolving in 50 ml water. Aliquots were made and stored at −20° C. until use.

Extracts of potato plant cuticle and adhering epidermis were prepared from thin strips from stems of potato plants. Extracts of wheat plant cuticle and adhering epidermis were prepared from thin strips from wheat sheath leaves. Extracts enriched in cell-wall glycans and non-cellulosic polysaccharides were sequentially extracted using CDTA and NaOH (Moller et al., 2007), respectively. Strips were frozen in liquid nitrogen and ground with mortar and pestle until fine powders were obtained. Cell-wall glycans-enriched extracts were prepared by resuspending the fine powders in 50 mM CDTA pH6.5 using 10 ml per gram of ground material and head-over-head rotation at 4° C. for 30 minutes. Extract and insoluble material were separated using a syringe adapted with a filter. The extracts were further cleared by centrifugation in a micro centrifuge at 20,000 g for 5 minutes. Non-cellulosic polysaccharide-enriched extracts were prepared from the insoluble material after CDTA extraction in 4 M NaOH and 1% $NaBH_4$ using 10 ml per gram of insoluble material and head-over-head rotation at 4° C. for 30 minutes. Extract and insoluble material were separated using a syringe adapted with a filter. The extracts were further cleared by centrifugation in a micro centrifuge at 20,000 g for 5 minutes.

First round selections against gum arabic were performed in wells of a 96-well plate (Maxisorp, Nunc) coated with 1 mg/ml or 10 µg/ml gum arabic in 0.1 M carbonate buffer pH 8.3. Coatings were performed at 4° C. overnight. Wells were washed three times with PBS/0.05%-TWEEN®-20 and blocked with 5% skimmed milk in PBS (5% MPBS). Phage were suspended in 2.5% MPBS and approximately 2E+11 cfu were used for each well. After binding to the wells at room temperature for 2 hours, unbound phage were removed by extensive washing with PBS/0.05%-TWEEN®-20 and PBS. Bound phage were eluted at room temperature with 0.1 mg/ml trypsin (Sigma) in PBS for 30 minutes. Eluted phage were transferred to a polypropylene 96-well plate (Nunc) containing excess AEBSF trypsin inhibitor (Sigma). The titers of phage from target-coated wells were compared to titers of phage from blank wells to assess enrichments. Phage were amplified using fresh TG1 cells according to standard procedures.

The second selection round was performed similarly to the first selection round except that for libraries 25 and 30 wells were coated with 10 µg/ml and 0.1 µg/ml gum arabic instead of 1 mg/ml and 10 µg/ml. No significant enrichments were obtained for libraries 27, 28, 29, 31, and 32 in selection round 1. In selection round 2, enrichments were >1000-fold for libraries 28, 31, and 32, and 25-fold and 250-fold for libraries 27 and 29, respectively. Enrichments for libraries 25 and 30 were 50-fold and >1000-fold in selection round 1, respectively. In selection round 2, enrichments were 1000-fold for both libraries. Selections against potato epidermal CDTA extract were performed similarly to the selections against gum arabic but wells were coated with ten-fold and 1000-fold diluted potato epidermal CDTA extract for both the first and second selection rounds. Enrichments in selection round 1 were 10, 1E+03, 20, 20, >1E+04, 15, and five-fold for libraries 25, 27, 28, 29, 30, 31, 32, respectively and >100-fold for all libraries in selection round 2. Selections against wheat epidermal CDTA extract were performed similarly to the selections against potato epidermal CDTA extract but wells were coated with 20-fold and 2000-fold diluted wheat epidermal CDTA extract for both the first and second selection rounds. Enrichments in selection round 1 were >10, >100, >10, 1, >1E+03, 10, and five-fold for libraries 25, 27, 28, 29, 30, 31, 32, respectively. Enrichments in selection round 2 were >ten-fold for library 29 and >100-fold for libraries 25, 27, 28, 30, 31, and 32. Selections against potato leaves were performed in two consecutive selection rounds using leaf particles in round 1 and whole leaves in round 2. Libraries 27, 28, 29, 30, 31, and 32 were used for selections against leaves. The leaf particles for first round selections were prepared by blending potato leaves in PBS using an Ultra-Turrax T25 homogenizer. The leaf particles were collected from the suspension by centrifugation. The supernatant, called herein "homogenized leaf soluble fraction," is assumingly enriched in intracellular components and was used in solution during phage selection to compete out binders to intracellular epitopes. Library phage were pre-incubated with the homogenized leaf soluble fraction in 2% MPBS using head-over-head rotation at room temperature for 30 minutes. The mixtures were added to leaf particles and incubated with head-over-head rotation at room temperature for 2 hours. Leaf particles with bound phage were collected by centrifugation and supernatants were discarded. Leaf particles with bound phage were washed extensively by consecutive washes with PBS. Washes were performed by resuspending leaf particles in PBS, spinning down leaf particles, and discarding supernatants. Elution of phage and infection of TG1 were performed as before. For the second selection round whole intact leaves were used. Leaves were incubated floating upside-down on phage solutions in 2% MPBS and phage were allowed to bind at room temperature for 2 hours. The leaves were washed extensively by transferring leaves to fresh tubes with PBS. Elution of bound phage was performed with 100 mM TEA in water, and solutions with eluted phage were neutralized using half of the eluted phage volume of 1 M Tris pH 7.5. Infection of TG1 was performed as before.

Picking Single Colonies from Selection Outputs—

Individual clones were picked from first and second round selections against gum arabic with libraries 25 and 30. From selections against gum arabic with libraries 27, 28, 29, 31, and 32, clones were picked after second round selections but not first round selections. A total of 208 clones was picked from gum arabic selections. From selections against potato epidermal CDTA extract a total of 321 clones was picked after both first and second round selections from all libraries. From selections against wheat epidermal CDTA extract a total of 162 clones was picked after second round selections from all libraries. From potato leaf selections a total of 184 clones was picked after second round selections from libraries 27, 28, 29, 30, 31, and 32. Fresh TG1 cells were infected with serially diluted eluted phage and plated on LB agar; 2% glucose; 100 µg/ml ampicillin. Single colonies were picked in 96-well plates containing 100 µl per well 2×TY; 10% glycerol; 2% glucose; 100 µg/ml ampicillin. Plates were incubated at 37° C. and stored at −80° C. as master plates.

Example 2

Characterization of the VHH

Single-Point Binding ELISA—

A single-point binding ELISA was used to identify clones that bind to gum arabic or plant extracts. VHH-containing extracts for ELISA were prepared as follows. 96-well plates with 100 µl per well 2×TY, 2% glucose 100 µg/ml ampicillin were inoculated from the master plates and grown at 37° C. overnight. 25 µl per well of overnight culture was used to inoculate fresh 96-well deep-well plates containing 1 ml per well 2×TY; 0.1% glucose; 100 µg/ml ampicillin. After growing at 37° C. in a shaking incubator for 3 hours, IPTG was added to 1 mM final concentration and recombinant VHH was produced during an additional incubation for 4 hours. Cells were spun down by centrifugation at 3,000 g for 20 minutes and stored at −20° C. overnight. Cell pellets were thawed, briefly vortexed, and 125 µl per well of room temperature PBS was added. Cells were resuspended on an ELISA shaker platform at room temperature for 15 minutes. Plates were centrifuged at 3,000 g for 20 minutes and 100 µl per well of VHH-containing extract was transferred to polypropylene 96-well plates (Nunc) and stored at −20° C. until further use.

Binding of clones from gum arabic selections was analyzed in ELISA plates coated with 100 µl/well gum arabic at 1 mg/ml in carbonate buffer pH 8.3. Binding of clones from potato epidermal CDTA extract selections was analyzed on both potato epidermal CDTA extract and wheat epidermal CDTA extract using ELISA plates coated with 100 µl per well of 30-fold diluted potato and 30-fold wheat epidermal CDTA extracts in 0.1 M carbonate pH 8.3. Binding of clones from wheat epidemial CDTA extract selections was analyzed using ELISA plates coated with 100 µl per well of 20-fold diluted wheat epidermal CDTA extract in 0.1 M carbonate pH 8.3. After coating at 4° C. overnight and continued coating at room temperature for 1 hour on the next day, plates were washed three times with PBS/0.05%-TWEEN®-20 and blocked with 5% skimmed milk in PBS for 1.5 hours. Plates were emptied and filled with 90 µl per well 1% MPBS. 10 µl of VHH-containing extract from each clone was added to (an) antigen-coated well(s) and a blank well. VHH were allowed to bind at room temperature for 1 hour and unbound VHH were removed by washing three times with PBS/0.05%-TWEEN®-20. Bound VHH were detected with sequential incubations with monoclonal mouse anti-histidine antibodies (Abd Serotec) in 1% MPBS/0.05%-TWEEN®-20 and rabbit anti-mouse IgG whole molecule antibodies conjugated with alkaline phosphatase (RaM/AP) (Sigma) in 1% MPBS/0.05%-TWEEN®-20. Unbound antibodies were removed by washing three times with PBS/0.05%-TWEEN®-20. The plates were washed an additional two times with PBS and 100 µl pNPP disodium hexahydrate substrate (Sigma) was added to each well.

The absorbance at 405 nm was measured and the ratio of VHH bound to (a) target-coated well(s) and a non-target-coated well was calculated for each clone. 23% of clones had a ratio greater than 2 and these clones were firstly picked for more detailed characterization. A second group of clones with a ratio between 1.15 and 2, and comprising 10% of all clones, was revisited later. Clones with a ratio less than 1.15 were not analyzed further.

For clones from whole leaf selections an adapted ELISA was developed. Upside-down floating leaf discs were used instead of coating wells with antigen. Incubations were similar to the extracts ELISA. After incubation with the substrate the leaf discs were removed from the wells using a forceps and the absorbance at 405 nm was measured. Signals obtained for each clone were compared to signals obtained from wells with leaf discs without primary antibody incubation and the ratios were calculated. A leaf surface-binding antibody that was found and characterized from epidermal extract selections was used as positive control antibody. VHH with a ratio greater than 1.5 were analyzed further by sequencing.

Single Colony PCR and Sequencing—

Single colony PCR and sequencing was performed on ELISA positive clones as follows. Cultures from master plate wells with ELISA positive clones were diluted ten-fold in sterile water. 5 µl from these diluted clones were used as template for PCR using forward primer MP57 (5'-ttatgcttc-cggctcgtatg-3' (SEQ ID NO:48)) and reverse primer GIII (5'-ccacagacagccctcatag-3' (SEQ ID NO:49)). PCR products were sequenced by Sanger-sequencing using primer MP57 (VIB Genetic Service Facility, University of Antwerp, Belgium).

Antibody Production and Purification—

VHH antibody fragments were produced in *E. coli* suppressor strain TG1 or non-suppressor strain WK6 (Fritz et al., *Nucleic Acids Research*, Volume 16 Number 14 1988) according to standard procedures. Briefly, colony streaks were made and overnight cultures from single colonies inoculated in 2×TY; 2% glucose; 100 µg/ml ampicillin. The overnight cultures were used to inoculate fresh cultures 1:100 in 2×TY; 0.1% glucose; 100 µg/ml ampicillin. After growing at 37° C. in a shaking incubator for 3 hours, IPTG was added to a 1 mM final concentration and recombinant VHH antibody fragments were produced during an additional incubation for 4 hours. Cells were spun down and resuspended in $1/50^{th}$ of the original culture volume of periplasmic extraction buffer (50 mM phosphate pH 7; 1 M NaCl; 1 mM EDTA) and incubated with head-over-head rotation at 4° C. overnight. Spheroplasts were spun down by centrifugation at 3,000 g and 4° C. for 20 minutes. Supernatants were transferred to fresh tubes and centrifuged again at 3,000 g and 4° C. for 20 minutes. Hexa-histidine-tagged VHH antibody fragments were purified from the periplasmic extract using $1/15^{th}$ of the extract volume of TALON metal affinity resin (Clontech), according to the manufacturer's instructions. Purified VHH antibody fragments were concentrated and dialyzed to PBS using Vivaspin 5 kDa MWCO devices (Sartorius Stedim), according to the manufacturer's instructions.

VHH Binding to Gum Arabic in ELISA—

Titration of VHH antibody fragments was performed on ELISA plates (Maxisorp, Nunc) coated with 100 µl per well 100 µg/ml gum arabic in 50 mM carbonate pH 9.6. Plates were coated at 4° C. overnight and coating was continued at room temperature for 1 hour on the next day. Plates were washed three times with PBS/0.05%-TWEEN®-20 and blocked with 5% skimmed milk in PBS for 1 hour. Four-fold serial dilutions of purified VHH antibody fragments were prepared in 1% MPBS/0.05%-TWEEN®-20 in polypropylene 96-well plates. Antibody concentrations ranged from 3 µg/ml to 12 ng/ml. Antibody dilutions were transferred to the gum arabic-coated plates and VHH antibody fragments were allowed to bind for 1 hour at room temperature. Bound VHH were detected with sequential incubations with monoclonal mouse anti-histidine antibodies (Abd Serotec) and rabbit anti-mouse IgG whole molecule antibodies conjugated with alkaline phosphatase (RaM/AP) (Sigma) in 1% MPBS/0.05%-TWEEN®-20. Unbound antibodies were removed by washing three times with PBS/0.05%-TWEEN®-20 after each antibody incubation. The plates were washed an additional two times with PBS and 100 µl pNPP disodium hexahydrate substrate (Sigma) was added to each well. The absorbance at 405 nm was measured and plotted as function of antibody concentration (see Table 1).

TABLE 1

| | | [VHH] (µg/ml) | | | | | |
|---|---|---|---|---|---|---|---|
| | | 3 | 3 | 0.75 | 0.1875 | 0.04688 | 0.0117188 |
| | | [VHH] (nM) | | | | | |
| | | 200 | 200 | 50 | 12.5 | 3.125 | 0.78125 |
| | | Gum arabic (100 µg/ml) | | | | | |
| | | − | + | + | + | + | + |
| | | 1 | 2 | 3 | 4 | 5 | 6 |
| VHH3E6 | A | 0.090 | 2.154 | 1.904 | 1.518 | 0.905 | 0.392 |
| VHH5C4 | B | 0.082 | 2.010 | 1.710 | 1.036 | 0.386 | 0.166 |
| VHH5D4 | C | 0.075 | 1.280 | 0.840 | 0.378 | 0.134 | 0.087 |
| VHH5G5 | D | 0.077 | 1.966 | 1.611 | 0.906 | 0.317 | 0.125 |
| VHH5E5 | E | 0.073 | 1.194 | 0.569 | 0.185 | 0.088 | 0.074 |
| VHH7D2 | F | 0.074 | 1.427 | 0.906 | 0.347 | 0.136 | 0.083 |
| VHH7C2 | G | 0.077 | 0.461 | 0.194 | 0.090 | 0.092 | 0.088 |
| VHH5F5 | H | 0.090 | 0.959 | 0.476 | 0.191 | 0.100 | 0.093 |
| VHH7A2 | F | 0.075 | 1.391 | 0.677 | 0.216 | 0.101 | 0.088 |

VHH Binding to Potato Lectin in ELISA

ELISA plates (Maxisorp, Nunc) coated with 100 µl per well 100 µg/ml potato lectin (Sigma) in PBS were coated at 4° C. overnight and coating was continued at room temperature for 1 hour on the next day. Plates were washed three times with PBS/0.05%-TWEEN®-20 and blocked with 5% skimmed milk in PBS for 1 hour. VHH (3 µg/ml) were transferred to the potato lectin-coated plates and VHH antibody fragments were allowed to bind for 1 hour at room temperature. Bound VHH were detected with sequential incubations with monoclonal mouse anti-histidine antibodies (Abd Serotec) and rabbit anti-mouse IgG whole molecule antibodies conjugated with alkaline phosphatase (RaM/AP) (Sigma) in 1% MPBS/0.05%-TWEEN®-20. Unbound antibodies were removed by washing three times with PBS/0.05%-TWEEN®-20 after each antibody incubation. The plates were washed an additional two times with PBS and 100 µl pNPP disodium hexahydrate substrate (Sigma) was added to each well and the absorbance at 405 nm was measured (see Table 2).

TABLE 2

| | VHH 3E6 | VHH 5D4 | VHH 5C4 | VHH 5G5 | VHH 7D2 | <Blank |
|---|---|---|---|---|---|---|
| Gum arabic | 0.882 | 0.530 | 0.873 | 0.751 | 0.274 | 0.069 |
| Potato lectin | 4.000 | 4.000 | 4.000 | 4.000 | 4.000 | 0.081 |
| Blank | 0.067 | 0.072 | 0.071 | 0.073 | 0.072 | 0.072 |

Example 3

Binding of Binding Domains to Plant Surface

VHH Binding to Leaf discs—

VHH binding to non-fixed leaf discs of potato (variety Desiree), black nightshade, grass, wheat or azalea was investigated. For comparison, binding of CBM3a to non-fixed leaf discs of potato (variety Desiree) was analyzed in parallel. Leaf discs were prepared by punching a fresh potato leaf with a 5 mm belt hole puncher tool. Leaf discs were put immediately in wells of a 96-well plate containing 200 µl per well 5% MPBS or PBS, and incubated for 30 minutes. Leaf discs were transferred to solutions containing 5 µg/ml VHH antibody fragment, respectively, 5 µg/ml CBM3a in 2% MPBS or PBS and incubated for 60-90 minutes. Unbound VHH or CBM3a proteins were removed by washing three times with 2% MPBS or PBS. Bound VHH or CBM3a proteins were detected with incubation with monoclonal mouse anti-histidine antibodies directly conjugated with Alexa-488 fluorescent dye (Abd Serotec) in 1% MPBS for 1 hour. Unbound antibodies were removed by washing three times with PBS. Leaf discs were put on glass slides, covered with cover slips, and analyzed by microscopy or on a macrozoom microscope system (Nikon) or a SP5 confocal microscope system (Leica). By means of a non-limiting example, VHH antibody fragments (e.g., 3E6, 5D4) were found to be clearly binding to trichomes, stomata and cuticle at the leaf surface of potato leaves (FIGS. 1A-C). In sharp contrast, for CBM3a no binding at the surface of potato leaves was detected and only faint binding to the wound tissue at the cut edge of the potato leaf disc was observed (FIG. 1D). Some VHH hereof (e.g., 3E6) were also shown to bind specifically to the surface of black nightshade leaves or grass leaves or as shown in FIGS. 1F and 1G, respectively. No significant binding was observed to the leaf surface of wheat or azalea.

VHH Binding to Intact Living Plants—

Figure 2:
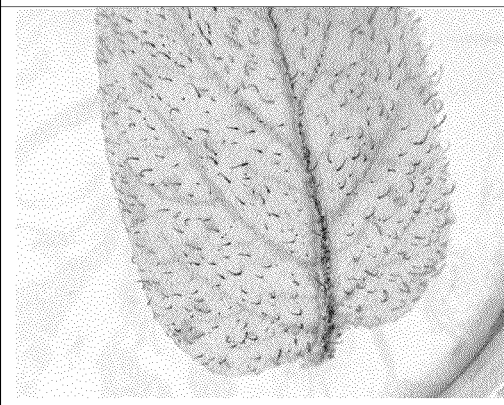
Figure 2:
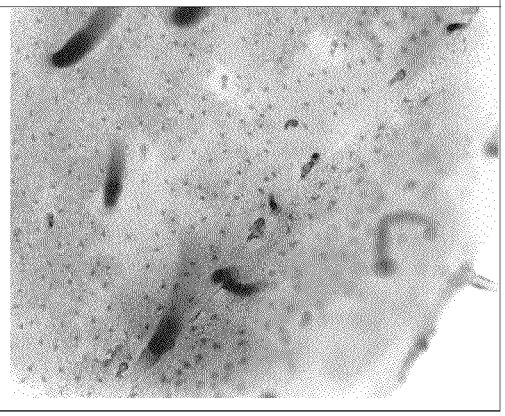

Binding of VHH to intact living plants was investigated on potato pot plants (variety Desiree). Compound leaves of intact living plants were submersed in solutions of hexahistidine-tagged VHH in PBS, or PBS alone for control conditions, leaving the compound leaves attached to the plants. VHH were allowed to bind for 1 hour. Next, the compound leaves still attached to the plants were washed five times in PBS in Erlenmeyer flasks. Different leaves and petiole sections were sampled. Bound VHH were detected by incubation with monoclonal mouse anti-histidine antibodies directly conjugated with Alexa-488 fluorescent dye (Abd Serotec) in PBS for 1 hour. Unbound anti-histidine antibodies were removed by washing five times with PBS. Whole leaves, leaf discs, or petiole sections were analyzed for bound VHH with microscopy. VHH proved to bind leaf structures such as trichomes and stomata, leaf surface, and petiole sections as shown in FIG. 2. No binding was observed with unrelated control VHH, proving that the VHH hereof are capable of specifically binding to intact living plants.

VHH Binding in Water—

Binding of VHH to leaf surfaces in water was investigated on leaf discs cut from leaves from potato plants (variety Desiree). Leaf discs were washed three times in ultrapure water. Hexahistidine-tagged VHH were diluted in ultrapure water, added to leaf discs, and allowed to bind for 1 hour. Although the stock solutions of VHH were in PBS, the dilutions used here (200-fold for 5 µg/ml, or 2000-fold for 500 ng/ml) result in significant dilution of PBS from the stocks and can be considered sufficiently dilute to represent binding in water. After allowing VHH to bind for 1 hour, leaf discs were washed five times with ultrapure water. Bound VHH were detected by incubation with monoclonal mouse anti-histidine antibodies directly conjugated with Alexa-488 fluorescent dye (Abd Serotec) in PBS for 1 hour. Unbound anti-histidine antibodies were removed by washing five times with PBS. Leaf discs were analyzed for bound VHH with microscopy. Binding of VHH in PBS was analyzed as described before as a control condition. Detection of bound VHH with anti-histidine antibodies conjugated with Alexa-488 fluorescent dye, washing away non bound anti-histidine antibodies, and analyzing bound VHH with microscopy was performed as for the VHH binding experiment in water. VHH proved to bind in water to leaf structures such as trichomes and stomata, and leaf surface. No binding was observed with unrelated control VHH. The observed binding in water was similar as seen for the parallel experiment performed in PBS. The VHH hereof are capable of binding leaf structures and leaf surface in water.

VHH Binding Kinetics

In order to further test applicability of VHH as binders for greenhouse or field applications where binding supposedly needs to be achieved quickly after application, a leaf dip VHH binding experiment was employed to test minimum incubation times of VHH to achieve detectable binding. ø 8 mm potato leaf discs (variety Desiree) were cut using a puncher tool and washed three times in PBS. 5 μg/ml pre-dilutions of hexahistidine-tagged VHH were prepared in PBS and incubated for different times with the leaf discs. The times for incubation were 10 seconds, 30 seconds, 1 minute, 5 minutes, 20 minutes, or 1 hour. Unbound VHH were removed by washing five times with PBS. Bound VHH were detected by incubation with monoclonal mouse anti-histidine antibodies directly conjugated with Alexa-488 fluorescent dye (Abd Serotec) in PBS for 1 hour. Unbound anti-histidine antibodies were removed by washing five times with PBS. Leaf discs were analyzed for bound VHH with microscopy. Specific binding was observed for each sample with specific VHH from incubation time 10 seconds to VHH incubation time 1 hour. No binding was observed with unrelated control VHH. The VHH hereof show detectable binding to leaf structures, such as trichomes and stomata and leaf surface within 10 seconds after application.

VHH binding at Different pH—

In order to test applicability of VHH as binders for greenhouse or field applications where binding supposedly may occur at pH-values, deviating strongly from physiological conditions in which antibodies naturally bind their targets, a leaf dip VHH binding experiment was carried out in a series of solutions with different pH. The following solutions were prepared: 50 mM glycine pH 2.0, 50 mM sodium acetate pH 4.0, 50 mm sodium carbonate pH 9.6, and 10 mM sodium hydroxide pH 11.0. ra 8 mm potato leaf discs (variety Desiree) were cut using a puncher tool. The leaf discs were first equilibrated to the different pH by washing three times with solutions at different pH. Hexahistidine-tagged VHH were diluted to 5 μg/ml in solutions with different pH, added to the corresponding equilibrated leaf discs, and binding of VHH was allowed for 1 hour. After incubation with VHH, leaf discs were washed three times with solutions at the corresponding different pH. After that, all were washed two times with PBS to equilibrate leaf discs to PBS. Bound VHH were detected by incubation with monoclonal mouse anti-histidine antibodies directly conjugated with Alexa-488 fluorescent dye (Abd Serotec) in PBS for 1 hour. Unbound anti-histidine antibodies were removed by washing five times with PBS. Leaf discs were analyzed for bound VHH with microscopy. Some of the VHH hereof (e.g., VHH 3E6) showed detectable binding to leaf discs over the whole range tested from pH 2 to pH 11.

VHH Binding at Different Temperatures—

In order to test applicability of VHH as binders for greenhouse or field applications where binding supposedly may occur at different and sometimes even extreme temperatures, a leaf dip VHH binding experiment at different temperatures was used. Temperatures used were 4° C., room temperature, 37° C., 55° C., or 70° C. ø 8 mm potato leaf discs (variety Desiree) were cut using a puncher tool. The leaf discs were equilibrated to different temperatures by washing three times with PBS at different temperatures. Hexahistidine-tagged VHH were diluted to 5 µg/ml in PBS at different temperatures, added to the corresponding equilibrated leaf discs, and binding of VHH was allowed for 1 hour at different temperatures. After incubation with VHH, leaf discs were washed five times with PBS at room temperature. Bound VHH were detected by incubation with monoclonal mouse anti-histidine antibodies directly conjugated with Alexa-488 fluorescent dye (Abd Serotec) in PBS for 1 hour at room temperature. Unbound anti-histidine antibodies were removed by washing five times with PBS at room temperature. Leaf discs were analyzed for bound VHH with microscopy. Some of the VHH hereof (e.g., VHH 3E6) showed detectable binding to leaf discs over a temperature range from 4° C. to 55° C. Please note that leaf discs severely suffer when submerged in PBS at 70° C. for 1 hour but that binding of VHH was still detected.

Example 4

Coupling of Targeting Agents to Microparticles

Construction, Production and Purification of Bivalent VHH—

Bivalent VHH constructs were produced in bacteria by cloning two VHH sequences in tandem into the pASF22 vector, creating a fusion of two VHH with a 9 glycine-serine linker (GGGGSGGGS (SEQ ID NO:50)) in between the two VHH. pASF22 is an in-house produced pMES derivative. The tags that were used were C-terminal c-Myc (EQKLISEEDLN (SEQ ID NO:51)) and hexahistidine (HHHHHH (SEQ ID NO:52)). A triple alanine linker (AAA) was placed in between the C-terminal end of the VHH and the c-Myc tag and a glycine-alanine-alanine (GAA) linker was used in between the C-terminal end of the c-Myc tag and the hexahistidine tag. The complete sequence C-terminal of the bivalent VHH that was used: AAA-EQKLISEEDLN-GAA-HHHHHH (SEQ ID NO:53). Fresh overnight cultures were produced by starting from colony streaks and inoculation of 2×TY media supplemented with 2% glucose and 100 μg/ml ampicillin. The overnight cultures were used to inoculate fresh cultures 1:100 in 2×TY media with 0.1% glucose and 100 μg/ml ampicillin. After growing at 37° C. in a shaking incubator for 3 hours, IPTG was added to a 1 mM final concentration and recombinant bivalent VHH were produced during an additional incubation for 4 hours. Cells were spun down and resuspended in 1/50th of the original culture volume of PBS and incubated with head-over-head rotation at 4° C. for 30 minutes. Spheroplasts were spun down by centrifugation at 3,000 g and 4° C. for 20 minutes. Supernatants were transferred to fresh tubes and centrifuged again at 3,000 g and 4° C. for 20 minutes. The supernatant was collected and sodium chloride concentration was adjusted to 500 mM and imidazole concentration to 20 mM. Hexahistidine-tagged bivalent VHH were purified from the extracts using HisTrap FF Crude 5 ml IMAC columns (GE Lifesciences) and HiLoad 16/60 Superdex 75 prep grade gel filtration column (GE Lifesciences) on an AKTAxpress system (GE Lifesciences) following standard procedures.

Coupling of VHH to Microparticles—

It was first examined whether VHH that are covalently bound to microparticles can bind their target and provide sufficient adhesion strength to a surface containing antigen for targeting of the microparticle. Microparticles were coupled with gum arabic-specific VHH antibody fragments and binding to ELISA plates coated with gum arabic was investigated.

Different types of microparticles were prepared. Purified VHH antibody fragments were (i) coupled to Ø 2.8 μm paramagnetic Dynabeads M-270 carboxylic acid (Dynal, Invitrogen), using a two-step coupling chemistry of EDC activation of the beads and subsequent coupling of VHH antibody fragments, and (ii) coupled using a one-step coupling chemistry to Ø 2 μm FluoSpheres fluorescent microspheres (Molecular Probes, Invitrogen), both according to the manufacturers' instructions.

Briefly, for coupling to Dynabeads M-270 carboxylic acid: VHH were dialyzed to 50 mM MES buffer pH 5.0 using Vivaspin 5 kDa spin filter devices (Sartorius Stedim). Beads were prepared by two sequential washes with 10 mM NaOH, and three washes with water, and activated with 0.1 M EDC (Pierce) at room temperature for 30 minutes. EDC-activated beads were washed by quick sequential washes with ice-cold water and ice-cold 50 mM MES buffer pH 5.0. Beads were dispensed with the last wash. 60 μg of VHH antibody fragment in 100 μl 50 mM MES pH 5.0 were added to 3 mg beads and incubated at room temperature for 30 minutes. The supernatant after coupling was collected. By measuring protein A280 of the non-bound fraction the amounts of coupled and non-coupled VHH were calculated. Greater than 95% of VHH antibody fragment were coupled to the beads. Beads were blocked with 50 mM Tris pH 7.4 and washed three times with PBS/0.1%-TWEEN®-20 and stored at 4° C.

Briefly, for coupling to FluoSpheres fluorescent microspheres: VHH were dialyzed to 50 mM MES buffer pH 6.0 using Vivaspin 5 kDa spin filter devices (Sartorius Stedim). 0.8 μM PES filter devices (Sartorius Stedim) were used throughout the procedure to isolate beads from solution. Beads were prepared by washing with ultrapure water and re-suspension in ultrapure water. 100 μl of VHH antibody fragments containing 200 μg VHH were added to 100 μl beads. 0.8 mg EDC (Pierce) was added to each mix of beads with VHH and the pH was adjusted to 6.5 with 0.1 M NaOH. Coupling was performed at room temperature for 2 hours. Glycine was added to a final concentration of 100 mM and incubated at room temperature for 30 minutes to quench the reaction. By measuring protein A280 of the non-bound fraction the amounts of coupled and non-coupled VHH were calculated. Between 14% and 33% of different VHH antibody fragments were coupled to the beads. Beads were washed twice with 50 mM phosphate pH 7.4; 0.9% NaCl (50 mM PBS) and stored in 1% BSA, 2 mM sodium azide in 50 mM PBS.

Coupling of Targeting Agents to Microcapsules Containing Fluorescent Tracer or Active Ingredient—

Polyurea microcapsules were produced by interfacial polymerization. With the objective to generate functionalized polyurea microcapsules, VHH were coupled to microcapsules containing either the insecticide lambda cyhalothrin or the fluorescent tracer molecule Uvitex OB and a shell with incorporated lysine to surface-expose carboxylic acid residues. Lambda cyhalothrin was dissolved in benzyl benzoate in concentrations between 30% and 66% before encapsulation. Alternatively, a core of 1.5% Uvitex in benzyl benzoate was used for easy fluorescent visualization of microcapsules. Toluene diisocyanate (TDI) and polymethylenepolyphenylene isocyanate (PMPPI) were dissolved in the oil phase in different ratios and concentrations in the oil phase to produce desired shell characteristics. Stirring speed for the emulsion was varied to control droplet size and consequently microcapsule diameter. Microcapsules with approximate diameters of 5 μm, 10 μm, or 50 μm were successfully produced. Bifunctional lysine and trifunctional diethylene triamine (DETA) were used in different ratios and/or added sequentially during encapsulation to on the one hand maximize amounts of carboxylic acids on the microcapsules' surface and on the other hand obtain sufficient strength of capsule shells. Microcapsules were washed with water after production and stored as microcapsule suspensions in water. The microcapsules were washed with 100 mM MES, 500 mM NaCl, pH 6.0 immediately before coupling of VHH using a vacuum-tight filter flask and P 1.6 filter funnel (Duran). Alternatively, glass filter holders with 0.45 μm disposable membrane filters (Millipore) or 0.45 μm 96-well deep-well filtration plates (Millipore) were used. Couplings of VHH to microcapsules were performed using carbodiimide-mediated couplings using a one-step procedure, a two-step procedure without N-hydroxysuccinimide (NHS), or a two-step procedure with NHS. The major difference between one-step coupling and two-step coupling procedures is the occurrence of cross-linking of VHH in one-step coupling procedures. The protocols for the three procedures are largely similar and differ as follows. For one-step couplings VHH were added to washed microcapsules and 1-Ethyl-3-[3-dimethylaminopropyl]carbodiimide Hydrochloride (EDC) (Pierce) was added and coupling reaction was allowed for 2 hours at room temperature. For two-step couplings washed microcapsules were first activated with EDC in the presence or absence of NHS. Excess unreacted EDC (and NHS) were removed by quick sequential washes with ice-cold buffers and VHH were added and allowed to react with activated carboxylic acids on microcapsule shells. For ø 10 μm microcapsules 2-20 μg VHH were coupled per mg microcapsules. For microcapsules with other diameters amounts were scaled accordingly. After coupling of VHH the microcapsules were washed with PBS and stored in PBS. Success of coupling of VHH was investigated using a combination of analyzing coupling efficiency by SDS-PAGE and analyzing bound hexahistidine-tagged VHH by microscopy or a SP5 confocal microscope system (Leica) using anti-histidine antibodies directly conjugated with Alexa-488 fluorescent dye. With SDS-PAGE analysis formation of multimers was observed for one-step coupling reactions as expected. VHH-coupled microcapsules were labeled with anti-histidine antibodies for 1 hour at room temperature. Unbound anti-histidine antibodies were removed by washing five times with PBS using 0.45 μm 96-well deep-well filtration plates (Millipore). Microcapsules with coupled VHH, microcapsules incubated with VHH to which no EDC was added, and blank microcapsules were compared. Anti-histidine labeling of microcapsules was most intense for microcapsules to which VHH had been coupled using either one-step or two-step coupling procedures as shown in FIG. 3. It was also observed that some VHH were passively adsorbed to the microcapsules. VHH were successfully coupled to microcapsules of different size using either one-step or two-step coupling procedures.

Example 5

Binding of Targeting Agent-Coupled Micro Particles to Antigen-Containing Surface Binding Assays with VHH-Coupled Beads or Microcapsules Functionality of VHH-coupled microparticles was investigated in ELISA plates that were coated with 100 μg/ml gum arabic in 50 mM carbonate pH 9.6 or PBS. Coating was performed overnight and plates were washed three times with PBS/0.05%-TWEEN®-20 and blocked with 5% skimmed milk in PBS for 1.5 hours. VHH-coupled paramagnetic beads were diluted 50-fold and incubated with monoclonal mouse anti-histidine antibodies directly conjugated with Alexa-488 fluorescent dye (Abd Serotec) in 1% MPBST for 1 hour. Two-fold serial dilutions (50- to 800-fold) of VHH-conjugated paramagnetic Dynabeads and FluoSpheres fluorescent beads were prepared in 2% MPBS, transferred to the gum arabic-coated ELISA plates, and incubated at room temperature for 1 hour. Unbound beads were removed by washing five times with PBS/0.05%-TWEEN®-20. The bottoms of ELISA plate wells were analyzed for bound beads by microscopy. Counting beads and using the microscope's camera mask for calculation of the analyzed surface area were used for calculating number of bound beads per well as shown in Table 3. Alternatively, microparticles were visualized using a macrozoom microscope system (Nikon) and counted using Volocity image analysis software (PerkinElmer); the number of bound Fluospheres per well is shown in Table 4.

TABLE 3

Counted bound magnetic carboxylic acid dynabeads to wells coated with gum arabic

| Dilution | Gum arabic | Magnetic Carboxylic Acid Dynabeads 2.8 μm (approximate numbers) | |
|---|---|---|---|
| | | Coupled with VHH 3E6 | Coupled with VHH 5D4 |
| 50 | + | ≈1000 | ≈500 |
| 100 | + | ≈500 | ≈500 |
| 200 | + | ≈200 | ≈200 |
| 400 | + | ≈100 | ≈200 |
| 800 | + | ≈100 | ≈100 |
| 50 | − | ≈10 | ≈50 |

TABLE 4

Counted bound Fluospheres to wells coated with gum arabic

| Coating | Number of Fluospheres added | Fluospheres coupled with VHH 3E6 | Fluospheres coupled with unrelated VHH |
|---|---|---|---|
| No coating | $4.5 \cdot 10^6$ | 115 | 198 |
| Gum arabic | $4.5 \cdot 10^6$ | 1874 | 224 |
| Gum arabic | $2.3 \cdot 10^6$ | 1273 | 89 |
| Gum arabic | $1.1 \cdot 10^6$ | 981 | 83 |

An ELISA-like assay setup was used to evaluate the interaction of VHH-coupled microcapsules to antigen-containing surfaces. ELISA plates (Maxisorp (Thermo Scientific Nunc) or high bind half area microplates (Greiner Bio-One)) were coated with gum arabic or potato lectin. Coatings were performed overnight with 100 μg/ml gum arabic or potato lectin in PBS. Control wells included blank wells or wells coated with unrelated antigens. Plates were washed three times with PBS with 0.05%-TWEEN®-20 and blocked with 5% skimmed milk in PBS for 1 to 2 hours. VHH-coupled lambda cyhalothrin-containing or Uvitex-containing microcapsules were diluted to appropriate densities in 1% skimmed milk in PBS with 0.05%-TWEEN®-20. Microcapsules were added to the antigen-coated or control wells and allowed to bind for 1 hour. Unbound microcapsules were removed by washing five times with PBS with 0.05%-TWEEN®-20. The bottoms of ELISA plate wells were analyzed for bound microcapsules on a macrozoom microscope system (Nikon). Microcapsules were counted using Volocity image analysis software (Perkin Elmer). A DAPI filter was used to visualize Uvitex microcapsules. White LED illumination and bright field pictures were used for lambda cyhalothrin microcapsules. Controls for lambda cyhalothrin-containing or Uvitex-containing microcapsules included blank microcapsules and microcapsules to which unrelated VHH were coupled.

TABLE 5

Bound microcapsules to wells coated with potato lectin or unrelated antigen

|  | Surface coverage | Counts Blank microcapsules | Counts Microcapsules containing lambda-cyhalothrin unrelated control | Counts VHH 3E6 | Area Microcapsules containing uvitex OB VHH 3E6 | Area unrelated control |
|---|---|---|---|---|---|---|
| no coating | 100% | 583 | 689 | 701 | 86.574 | 82.757 |
| potato lectin | 100% | 755 | 828 | 7.910 | 504.839 | 16.676 |
| potato lectin | 20% | 616 | 709 | 4.550 | 510.242 | 35.433 |
| potato lectin | 4% | 408 | 348 | 798 | 144.955 | 7.529 |
| no coating | 100% | n.d. | n.d. | 209 | 68.181 | 60.841 |
| unrelated antigen | 100% | n.d. | n.d. | 861 | 84.508 | 94.153 |
| unrelated antigen | 20% | n.d. | n.d. | 601 | 47.906 | 39.218 |
| unrelated antigen | 4% | n.d. | n.d. | 386 | 23.525 | 18.517 |

In another experiment, lambda cyhalothrin amounts were also determined analytically. 100 μl/well acetone was added to washed wells with bound microcapsules and transferred to glass vials with 10 ml of hexane containing 0.05% triphenylphosphate as internal standard. The amount of lambda cyhalothrin was determined by GC/MS-MS analysis in comparison with calibration solutions. Controls for lambda cyhalothrin microcapsules included blank microcapsules to which no VHH were coupled and microcapsules to which unrelated VHH were coupled. Controls also included wells to which no gum arabic or potato lectin was coated. Based on the results of the ELISA-like assay with lambda cyhalothrin microcapsules it was found that some of the VHH hereof (e.g., VHH3E6) are capable of binding and retaining microcapsules to antigen-coated surfaces resulting in a 23-fold increase of amounts of lambda cyhalothrin in wells coated with antigen compared to blank microcapsules and a 27-fold increase was measured over blank wells not coated with antigen.

Based on the results of the microcapsule binding assays, VHH could be classified as capable or not capable of binding and retaining microcapsules to a surface. Some of the VHH hereof (e.g., VHH3E6) proved capable of binding specifically to antigen-coated surfaces when coupled to a microcapsule. No significant binding to surfaces with unrelated antigens was observed. Moreover, the specific binding was strong enough to retain the microcapsule at the antigen-coated surface, as the binding force clearly resists the shear forces that occur during the washing procedure. What is more is that VHH are capable of binding and retaining microcapsules containing relevant active ingredients to surfaces, as shown, for example, with microcapsules containing the insecticide lambda cyhalothrin.

Next, it was investigated if binding of microcapsules to surfaces could be improved by using targeting agents comprising multivalent VHH. A series of parallel couplings was performed with equal amounts of monovalent VHH, bivalent VHH, and unrelated VHH. Success of coupling of VHH and multivalent VHH were analyzed as described in Example 4. An ELISA-like assay was performed using high bind half area microplates (Greiner Bio-One) coated with 5 μg/well potato lectin. Control wells included blank wells or wells coated with unrelated antigens. Plates were washed three times with PBS with 0.05%-TWEEN®-20 and blocked with 5% skimmed milk in PBS for 1 to 2 hours. VHH-coupled Uvitex-containing microcapsules were diluted to appropriate densities in 1% skimmed milk in PBS with 0.05%-TWEEN®-20. Five-fold serial dilution series were prepared and allowed to bind to the surface to compare binding of microcapsules coupled with monovalent or bivalent VHH. Microcapsules were added to the antigen-coated or control wells and allowed to bind for 1 hour. Unbound microcapsules were removed by washing five times with PBS with 0.05%-TWEEN®-20. The bottoms of ELISA plate wells were analyzed for bound microcapsules on a macrozoom microscope system (Nikon). Microcapsules were counted using Volocity image analysis software (Perkin Elmer). A DAPI filter was used to visualize Uvitex microcapsules. Bivalent VHH proved capable of binding specifically to an antigen-coated surface when coupled to a microcapsule and more microcapsules were retained using bivalent VHH compared to microcapsules with monovalent VHH. With the highest density of microcapsules applied (calculated to fully cover the surface of the bottom of the well) it was found that 17% more microcapsules with coupled bivalent VHH were retained in the well compared to the same amount of microcapsules with monovalent VHH. With an application of 25-fold less microcapsules it was found that 160% more microcapsules were retained in the well for microcapsules coupled with bivalent VHH compared to microcapsules with monovalent VHH. The surface area of microcapsules with coupled bivalent VHH was 15-fold above the surface area of blank microcapsules applied at this microcapsule density while the surface area of microcapsules with monovalent VHH was only six-fold above the surface area of blank microcapsules applied at this microcapsule density. This difference could be explained by an increase in binding strength due to additional avidity of the bivalent VHH compared to monovalent VHH, it could also be that the use of bivalent VHH increases flexibility and spacer length of the coupled targeting agents on microcapsules, or a combination of both.

TABLE 6

Surface areas of bound microcapsules to wells coated with potato lectin or unrelated antigen

|  | Surface coverage | Monovalent VHH 3E6 | Bivalent VHH 3E6 | unrelated VHH | Blank microcapsules |
|---|---|---|---|---|---|
| no coating | 100% | 74.536 | 66.176 | 77.014 | 84.982 |
| potato lectin | 100% | 415.773 | 490.546 | 141.636 | 90.030 |
| potato lectin | 20% | 307.478 | 511.303 | 43.452 | 44.024 |

TABLE 6-continued

Surface areas of bound microcapsules to wells coated with potato lectin or unrelated antigen

| | Surface coverage | Monovalent VHH 3E6 | Bivalent VHH 3E6 | unrelated VHH | Blank microcapsules |
|---|---|---|---|---|---|
| potato lectin | 4% | 59.377 | 155.759 | 19.170 | 10.599 |
| no coating | 100% | 72.036 | 55.841 | 68.109 | 66.509 |
| unrelated antigen | 100% | 69.503 | 45.677 | 78.205 | 50.965 |
| unrelated antigen | 20% | 27.742 | 22.114 | 30.459 | 17.831 |
| unrelated antigen | 4% | 5.011 | 15.038 | 19.755 | 6.279 |

A leaf disc binding assay was used to evaluate the interaction of VHH-coupled microcapsules with potato, grass and azalea leaves. ø 8 mm leaf discs were sampled from the leaves of potato pot plants (variety Desiree), from the leaves of greenhouse-grown *Lollium perenne* and from the leaves of azalea pot plants. Leaf discs were washed three times with PBS. Microcapsules containing lambda cyhalothrin or Uvitex were diluted to appropriate densities in 1% skimmed milk in PBS with 0.05%-TWEEN®-20. Microcapsules were added to the leaf discs and settling of microcapsules and binding of targeting agents allowed for 1 hour. Unbound microcapsules were removed by washing three to five times with PBS with 0.05%-TWEEN®-20.

For lambda cyhalothrin microcapsules, a residue analysis was performed to measure lambda cyhalothrin amounts on potato leaf discs. Washed leaf discs with bound microcapsules were transferred to glass vials and microcapsules were dissolved in acetone. Samples were diluted by addition of hexane containing 0.05% triphenylphosphate as internal standard. The amount of lambda cyhalothrin was determined by GC/MS-MS analysis in comparison with calibration solutions. Controls for lambda cyhalothrin microcapsules included blank microcapsules to which no VHH were coupled and microcapsules to which unrelated VHH were coupled. Based on the results of leaf disc binding assays with lambda cyhalothrin microcapsules, it was found that some of the VHH hereof are capable of binding and retaining microcapsules to leaf surfaces resulting in a 3.3-fold and 2.2-fold increase of amounts of lambda cyhalothrin on leaf discs compared to blank microcapsules to which no VHH were coupled or microcapsules with coupled unrelated VHH, respectively.

Leaf discs with Uvitex microcapsules were analyzed for bound microcapsules on a macrozoom microscope system (Nikon). Microcapsules were counted using Volocity image analysis software (Perkin Elmer). A DAPI filter was used to visualize Uvitex microcapsules. Controls for Uvitex microcapsules included blank microcapsules to which no VHH were coupled and microcapsules to which unrelated VHH were coupled. Based on the results of the leaf disc binding assay with Uvitex microcapsules it was found that some of the VHH (e.g., VHH 3E6) hereof proved capable of binding and retaining microcapsules specifically to leaf surfaces.

Figure 4:
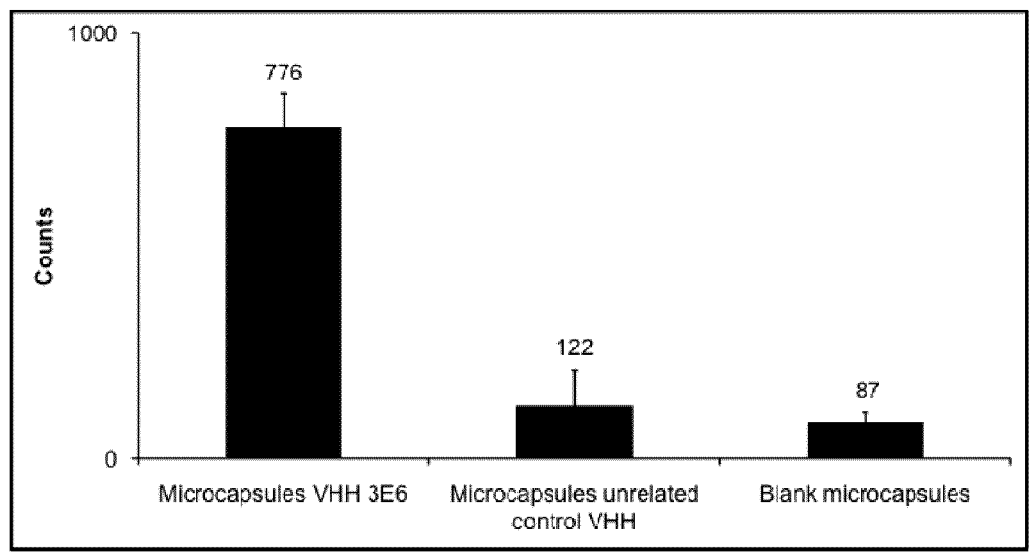

On potato leaf discs, specific binding of the microcapsules coupled with VHH 3E6, resulted in nine-fold more microcapsules bound to leaf surfaces compared to blank microcapsules and in six-fold more microcapsules bound to leaf surfaces compared to microcapsules coupled with unrelated VHH, as shown in FIG. 4. On grass leaf discs, specific binding of microcapsules coupled with VHH 3E6 resulted in three-fold more microcapsules bound to leaf surfaces compared to blank microcapsules and in two-fold more microcapsules bound to leaf surfaces compared to microcapsules coupled with unrelated VHH. On azalea leaf discs, no specific binding of microcapsules coupled with VHH 3E6 could be observed, which entirely resembles the plant-species related binding specificity of the VHH as demonstrated in Example 3.

Figure 5:
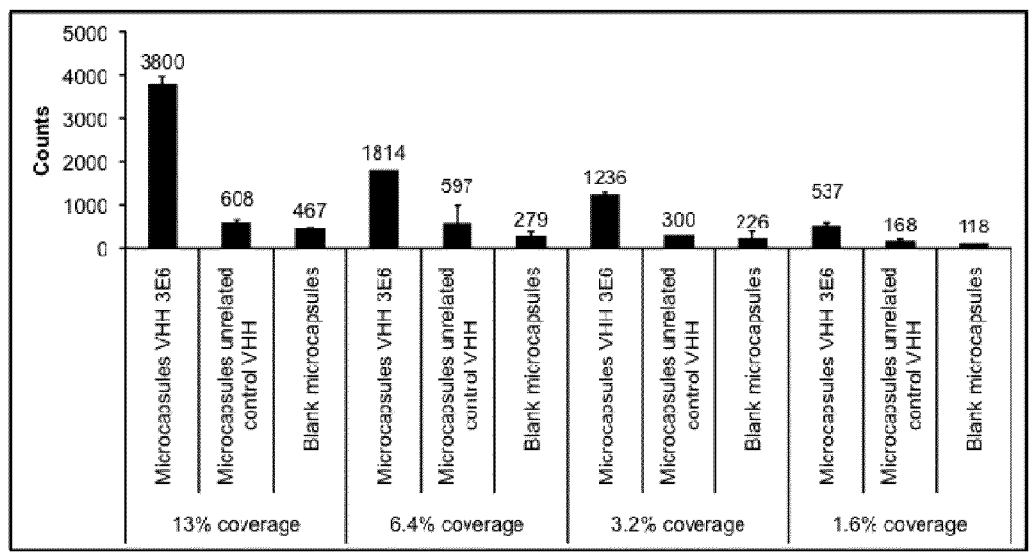

A titration experiment was performed to investigate what dilution factor of microcapsules with specific VHH corresponds to an application of microcapsules to which no VHH were coupled to obtain similar amounts of microcapsules after an identical treatment. Two-fold serial dilutions of microcapsules were prepared and leaf disc binding was analyzed on potato leaf discs for these dilution series. From the dosing experiment it was calculated that an eight-fold lower concentration of microcapsules with specific VHH resulted in similar amounts of microcapsules specifically bound to the leaf discs compared to non-functionalized microcapsules as shown in FIG. 5. From this experiment, it will be clear that a meaningful reduction of a suitable dose of an agrochemical can be achieved, by coupling one of the VHH hereof, to a microcarrier containing the agrochemical.

Example 6

Deposition and Retention of Targeting Agent-Coupled Microcapsules on Intact Living Plant Surface Effects on deposition and retention of carriers with coupled targeting agents were investigated in experiments with whole potato pot plants (variety Desiree) grown in greenhouses. Microcapsules coupled with specific VHH, coupled with unrelated control VHH, or blank microcapsules were applied to multiple whole compound leaves from different plants. In total 15 plants were used for different treatments. Microcapsule suspensions were calculated to apply 6.4% coverage of microcapsules on leaf surfaces. Compound leaves were submerged in microcapsule suspensions in the same way as for microcapsule leaf disc binding assays (see above) with the modification that settling of microcapsules and binding of VHH was allowed for only 15 minutes. Plants were allowed to dry up for 1 hour after application of microcapsules. One of each pair of opposite leaves from within each compound leaf was sampled and analyzed without any further treatment.

The effects of specific VHH coupled to microcapsules on microcapsule deposition could be analyzed with these leaves from different applications. The whole plants missing only the sampled leaves were treated further to investigate the effect of specific VHH coupled to microcapsules on retention after a rainfall event and the combined effects of deposition and retention. A rain simulation with fine droplets (SSCOT-FVS2 nozzle type) of 1 L/m2 in 45 seconds was used to investigate retention effects. The opposite leaves of already sampled leaves were sampled after the rain simulation. Whole leaves with Uvitex microcapsules were analyzed for bound microcapsules on a macrozoom microscope system (Nikon). Microcapsules were counted using Volocity image analysis software (Perkin Elmer). A DAPI filter was used to visualize Uvitex microcapsules. From the leaves that were sampled before the rainfall event it was calculated that already 2.7-fold more microcapsules were deposited for microcapsules with specific targeting agent compared to blank microcapsules. Leaves with microcapsules with unrelated control targeting agent contained only a 0.8 fraction of microcapsules compared to blank microcapsules. This shows that specific VHH already have a beneficial effect on the deposition of microcapsules on plants. On average 69 (±8) % of microcapsules with specific VHH was retained after the rainfall event while only 35 (±17) % and 39 (±4) % of microcapsules was retained for microcapsules coupled with unrelated control VHH and blank microcapsules, respectively. The combination of effects of deposition and retention resulted in five-fold and 0.9-fold in the amount of microcapsules on leaves on whole plants for microcapsules with specific VHH or unrelated control VHH, compared to blank microcapsules, respectively.

From this experiment, it will be clear that specific VHH are superior targeting agents that enable delivery and specific binding of carriers to whole intact living plants. As a consequence of improved deposition and improved retention targeting agents hereof coupled to carriers containing an agrochemical or a combination of agrochemicals hold great promise to deliver the agrochemicals specifically to plant surfaces and hereby either increase amounts of the agrochemicals deposited on the plant surface, or enable reduced application rates while maintaining similar efficacy, or enable reduced application frequencies while maintaining similar efficacy or enable improved rainfastness of the agrochemicals or induce a certain specificity for the agrochemicals or any combination of the foregoing.

REFERENCES

Altschul S. F., T. L. Madden, A. A. Schäffer, J. Zhang, Z. Zhang, W. Miller, and D. J. Lipman (1997). Gapped BLAST and PSI-BLAST: a new generation of protein database search programs, *Nucleic Acids Res.* 25:3389-3402.

Blake A. W., L. McCartney, J. Flint, D. N. Bolam, A. B. Boraston, H. J. Gilbert, and J. P. Knox (2006). Understanding the biological rationale for the diversity of cellulose-directed carbohydrate-binding molecules in prokaryotic enzymes. *J. Biol. Chem.* 281:29321-29329.

Calo L., I. Garcia, C. Gotor, and L. C. Romero (2006). Leaf hairs influence phytopathogenic fungus infection and confer an increased resistance when expressing a *Trichoderma* α-1,3-glucanase. *J. Exp. Botany* 57:3911-3920.

Cozens-Roberts C., J. A. Quinn, and D. A. Lauffenburger (1990). Receptor-mediated cell attachment and detachment kinetics. *Biophys. J.* 58:857-872.

Dimitrov D. S. (2009). Engineered CH2 domains (nanoantibodies). mAbs 1:26-28.

Gage D. J. (2004). Infection and invasion of roots by symbiotic, nitrogen fixing *Rhizobia* during nodulation of temperate legumes. *Microbiol. Mol. Biol. Rev.* 68:280-300.

Jones L., G. B. Seymour, and J. P. Knox (1997). Localization of pectic galactan in tomato cell walls using a monoclonal antibody specific to (1-4)-β-D-galactan. *Plant Physiol.* 113:1405-1412.

Kolmar H. (2008). Alternative binding proteins: biological activity and therapeutic potential of cysteine-knot miniproteins. *FEBS J.* 275:2684-2690.

Lai A., V. Cianciolo, S. Chiavarini, and A. Sonnino (2000). Effect of glandular trichomes on the development of *Phytophtora* infestans infection in potato (*S. tuberosum*). *Euphytica* 114:165-174.

Laus M. C., A. A. N. van Brussel, and J. W. Kijne (2005). Role of cellulose fibrils and exopolysaccharides of *Rhizobium leguminosarum* in attachment and infection of *vicia* sativa root hairs. *Mol. Plant-Microbe interactions* 18:533-538.

Melotto M., W. Underwood, J. Koczan, K. Nomura, and S. Y. He (2006). Plant stomata function in innate immunity against bacterial invasion. *Cell* 126:969-980.

Moller I., I. Sorensen, A. J. Bernal, C. Blaukopf, K. Lee, J. Obro, F. Pettolino, A. Roberts, J. D. Mikkelsen, J. P. Knox, A. Bacic, and W. G. Willats (2007). High throughput mapping of cell-wall polymers within and between plants using novel microarrays. *Plant J.* 50:1118-1128.

Nygren P-A. (2008). Alternative binding proteins: affibody binding proteins developed from a small three-helix bundle scaffold. *FEBS J.* 275:2668-2676.

Pennell R. I., J. P. Knox, G. N. Scofield, R. R. Selvendran, and K. Roberts (1989). A family of abundant plasma membrane associated glycoproteins related to the arabinogalactan proteins is unique to flowering plants. *J. Cell. Biol.* 108:1967-1977.

Scher H. B., M. Rodson, and K-S Lee (1998). Microencapsulation of pesticides by interfacial polymerization utilizing isocyanate or aminoplast chemistry. *Pestic. Sci.* 54:394-400.

Schreiber L. (2005). Polar paths of diffusion across plant cuticles: new evidence for an old hypothesis. *Ann. Bot.* 95:1069-1073.

Skerra A. (2008). Alternative binding proteins: anticalins—harnessing the structural plasticity of the lipocalin ligand pocket to engineer novel binding activities. *FEBS J.* 275:2677-2683.

Stump M. T., H. K. Binz, and P. Amstutz (2008). DARPins: a new generation of protein therapeutics. *Drug Discov. Today* 13:695-701.

Tramontano A., E. Bianchi, S. Venturini, F. Martin, A. Pessi and M. Sollazzo (1994). The making of the minibody: an engineered beta-protein for the display of conformationally constrained peptides. *J. Mol. Recognition.* 7:9-24.

Underwood W., M. Melotto, and S. Y. He (2007). Role of plant stomata in bacterial invasion. *Cellular Microbiol.* 9:1621-1629.

Wesolowski J., V. Alzogaray, J. Reyelt, M. Unger, K. Juarez, M. Urrutia, A. Cauerhiff, W. Danquah, B. Rissiek, F. Scheuplin, N. Schwarz, S. Adriouch, O. Boyer, M. Seman, A. Licea, D. V. Serreze, F. A. Goldbaum, F. Haag, and F. Koch-Nolte (2009). Single domain antibodies: promising experimental and therapeutic tools in infection and immunity. *Med. Microbiol. Immunol.* 198:157-174.

Willats W. G. and J. P. Knox (1999). Immunoprofiling of pectic polysaccharides. *Anal. Biochem.* 268:143-146.

Willats W. G., S. E. Marcus, and J. P. Knox (1998). Generation of monoclonal antibody specific to (A-5)-alpha-L-arabinan. *Carbohydr. Res.* 308:149-152.

Willats W. G., C. Orfila, G. Limberg, H. C. Buchholt, G-J. W. M. van Alebeek, A. G. J. Voragen, S. E. Marcus, T. M. I. E. Christensen, J. D. Mikkelsen, B. S. Murray, and J. P. Knox (2001). Modulation of the degree and pattern of methyl-esterification of pectic homogalacruronan in plant cell walls. *J. Biol. Chem.* 276:19404-19413.

What is claimed is:

1. A binding domain able to bind at least one binding site on an active, living plant, wherein the binding domain is derived from a camelid antibody and comprises a VHH sequence comprising a peptide selected from the group consisting of SEQ ID NOs:1-42.

2. A targeting agent, comprising:
   at least one binding domain of claim 1,
   wherein the binding domain is able to retain an agrochemical on a plant and/or on a plant part.

3. The targeting agent of claim 2, wherein said agrochemical is bound on or comprised in a carrier.

4. The targeting agent of claim 2, wherein said binding domain binds to a specific structure on the plant.

5. The targeting agent of claim 4, wherein said specific structure is selected from the group consisting of trichomes, stomata, lenticels, thorns, spines, root hairs, cuticle and wax layer.

6. The targeting agent of claim 2, wherein said binding domain binds to gum Arabic.

7. The targeting agent of claim 2, wherein said binding domain binds to a lectin, lectin-like domain, extensin, or extensin-like domain.

8. A method of delivering an agrochemical or a combination of agrochemicals to a plant and/or a plant part, the method comprising:
   delivering a targeting agent comprising:
      a VHH sequence comprising a binding domain that binds at least one binding site on an active, living plant, wherein the binding domain is derived from a camelid antibody and comprises a peptide selected from the group consisting of SEQ ID NOs: 1-42, wherein the binding domain is able to retain an agrochemical on a plant and/or on a plant part, together with
      the agrochemical or combination of agrochemicals
   to the plant and/or plant part.

9. The method according to claim 8, wherein said agrochemical or combination of agrochemicals is selected from the group consisting of herbicides, insecticides, fungicides, nematicides, biocides, fertilizers, safeners, micro-nutrients and plant growth regulators.

10. The method according to claim 9, wherein said agrochemical or combination of agrochemicals is bound on or comprised in a carrier.

11. The method according to claim 10, wherein said carrier is a microcarrier.

12. The method according to claim 11, wherein said microcarrier is selected from the group consisting of microcapsules, microspheres, nanocapsules, nanospheres, polymer particles, particles made from artificially lignified cellulose, composite gel particles, weak ionic resin particles, microbial cells and fragments thereof.

13. The method according claim 10, wherein said targeting agent is coupled to said carrier by a functional group on the outer surface of the carrier.

14. The method according to claim 13, wherein said targeting agent is coupled to said functional group by a covalent bond.

15. A composition, comprising:
   (a) at least one targeting agent comprising a VHH sequence comprising a binding domain that binds at least one binding site on an active, living plant, the binding domain being derived from a camelid antibody, comprising a peptide selected from the group consisting of SEQ ID NOs: 1-42, and able to retain an agrochemical on a plant part, and
   (b) an agrochemical or combination of agrochemicals.

16. A composition, comprising:
   (a) at least one targeting agent of claim 4, and
   (b) an agrochemical or a combination of agrochemicals.

17. The composition of claim 15, wherein said agrochemical or combination of agrochemicals is bound on or comprised in a carrier.

18. A composition, comprising (a) at least one targeting agent comprising a VHH sequence comprising a binding domain that binds at least one binding site on an active, living plant, wherein the binding domain is derived from a camelid antibody and comprises a peptide selected from the group consisting of SEQ ID NOs: 1-42, wherein the binding domain is able to retain an agrochemical on a plant and/or on a plant part and (b) a carrier.

19. A composition, comprising:
   (a) at least one targeting agent comprising: a VHH sequence comprising a binding domain that binds at least one binding site on an active, living plant, wherein the binding domain is derived from a camelid antibody and comprises a peptide selected from the group consisting of SEQ ID NOs: 1-42, wherein the binding domain is able to retain an agrochemical on a plant and/or on a plant part, wherein said targeting agent comprises at least one binding domain that comprises four framework regions and three complementarity-determining regions, or any suitable fragment thereof, and
   (b) a carrier.

20. The composition of claim 18, wherein said targeting agent is coupled to said carrier.

21. The composition of claim 20, wherein said targeting agent is covalently coupled to said carrier.

22. The composition of claim 18, wherein said carrier is coupled to and/or comprises at least one agrochemical.

23. The composition of claim 17, wherein said agrochemical is selected from the group consisting of herbicides, insecticides, fungicides, nematicides, biocides, fertilizers, safeners, micro-nutrients and plant growth regulating compounds.

24. The composition of claim 17, wherein said carrier is selected from the group consisting of microcapsules, microspheres, polymer particles, particles made from artificially lignified cellulose, composite gel particles, weak ionic resin particles, microbial cells and fragments thereof.

25. A method for delivering an agrochemical or a combination of agrochemicals to a plant, said method comprising at least one application of the composition of claim 15 on said plant.

26. The method for delivering an agrochemical or combination of agrochemicals according to claim 25, wherein the dose of the agrochemical or combination of agrochemicals is reduced compared to the efficacious dose of the same agrochemical or combination of agrochemicals comprised in a comparable composition without a targeting agent.

27. A method for protecting a plant and/or to modulate the viability, growth or yield of a plant or plant parts and/or to modulate gene expression in a plant or plant parts, said method comprising at least one application of the composition of claim 15 on said plant.

28. The method for protecting a plant and/or to modulate the viability, growth or yield of a plant or plant parts and/or to modulate gene expression in a plant or plant parts according to claim 27, wherein the dose of the agrochemical or combination of agrochemicals is reduced compared with the efficacious dose of the same agrochemical or combination of agrochemicals comprised in a comparable composition, without any targeting agent.

29. A method for producing a specifically targeting agrochemical carrier, said method comprising:
   (a) packing an agrochemical or a combination of agrochemicals in or on a carrier, and
   (b) attaching a targeting agent comprising: a VHH sequence comprising a binding domain that binds at least one binding site on an active, living plant, wherein the binding domain is derived from a camelid antibody and comprises a peptide selected from the group consisting of SEQ ID NOs: 1-42, wherein the binding domain is able to retain an agrochemical on a plant and/or on a plant part to said carrier.

30. A process for attaching a targeting agent comprising a VHH sequence comprising a binding domain that binds at least one binding site on an active, living plant, wherein the binding domain is derived from a camelid antibody and comprises a peptide selected from the group consisting of SEQ ID NOs: 1-42, wherein the binding domain is able to retain an agrochemical on a plant and/or on a plant part to a carrier, the process comprising:
   (a) reacting a linking agent with a carrier, and
   (b) reacting said targeting agent with said linking agent.

31. A specifically targeting agrochemical carrier obtained by the method according to claim 29.

32. The composition of claim 15, wherein the peptide comprises SEQ ID NO:1.

33. The composition of claim 15, wherein the peptide comprises SEQ ID NO:2.

34. The composition of claim 15, wherein the peptide comprises SEQ ID NO:3.

35. The composition of claim 15, wherein the peptide comprises SEQ ID NO:4.

36. The composition of claim 15, wherein the peptide comprises SEQ ID NO:5.

37. The composition of claim 15, wherein the peptide comprises SEQ ID NO:6.

38. The composition of claim 15, wherein the peptide comprises SEQ ID NO:7.

39. The composition of claim 15, wherein the peptide comprises SEQ ID NO:8.

40. The composition of claim 15, wherein the peptide comprises SEQ ID NO:9.

41. The composition of claim 15, wherein the peptide comprises SEQ ID NO:10.

42. The composition of claim 15, wherein the peptide comprises SEQ ID NO:11.

43. The composition of claim 15, wherein the peptide comprises SEQ ID NO:12.

44. The composition of claim 15, wherein the peptide comprises SEQ ID NO:13.

45. The composition of claim 15, wherein the peptide comprises SEQ ID NO:14.

46. The composition of claim 15, wherein the peptide comprises SEQ ID NO:15.

47. The composition of claim 15, wherein the peptide comprises SEQ ID NO:16.

48. The composition of claim 15, wherein the peptide comprises SEQ ID NO:17.

49. The composition of claim 15, wherein the peptide comprises SEQ ID NO:18.

50. The composition of claim 15, wherein the peptide comprises SEQ ID NO:19.

51. The composition of claim 15, wherein the peptide comprises SEQ ID NO:20.

52. The composition of claim 15, wherein the peptide comprises SEQ ID NO:21.

53. The composition of claim 15, wherein the peptide comprises SEQ ID NO:22.

54. The composition of claim 15, wherein the peptide comprises SEQ ID NO:23.

55. The composition of claim 15, wherein the peptide comprises SEQ ID NO:24.

56. The composition of claim 15, wherein the peptide comprises SEQ ID NO:25.

57. The composition of claim 15, wherein the peptide comprises SEQ ID NO:26.

58. The composition of claim 15, wherein the peptide comprises SEQ ID NO:27.

59. The composition of claim 15, wherein the peptide comprises SEQ ID NO:28.

60. The composition of claim 15, wherein the peptide comprises SEQ ID NO:29.

61. The composition of claim 15, wherein the peptide comprises SEQ ID NO:30.

62. The composition of claim 15, wherein the peptide comprises SEQ ID NO:31.

63. The composition of claim 15, wherein the peptide comprises SEQ ID NO:32.

64. The composition of claim 15, wherein the peptide comprises SEQ ID NO:33.

65. The composition of claim 15, wherein the peptide comprises SEQ ID NO:34.

66. The composition of claim 15, wherein the peptide comprises SEQ ID NO:35.

67. The composition of claim 15, wherein the peptide comprises SEQ ID NO:36.

68. The composition of claim 15, wherein the peptide comprises SEQ ID NO:37.

69. The composition of claim 15, wherein the peptide comprises SEQ ID NO:38.

70. The composition of claim 15, wherein the peptide comprises SEQ ID NO:39.

71. The composition of claim 15, wherein the peptide comprises SEQ ID NO:40.

72. The composition of claim 15, wherein the peptide comprises SEQ ID NO:41.

73. The composition of claim 15, wherein the peptide comprises SEQ ID NO:42.

* * * * *

SEQUENCE LISTING

<160> NUMBER OF SEQ ID NOS: 53

<210> SEQ ID NO 1
<211> LENGTH: 123
<212> TYPE: PRT
<213> ORGANISM: Lama glama

```
<220> FEATURE:
<221> NAME/KEY: MISC_FEATURE
<223> OTHER INFORMATION: 3A2
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 1

Gln Val Gln Leu Gln Glu Ser Gly Gly Gly Leu Val Gln Pro Gly Arg
1               5                   10                  15

Ser Leu Lys Val Ala Cys Ala Ala Gly Phe Ser Leu Arg Tyr Tyr
            20                  25                  30

Gly Ile Gly Trp Phe Arg Gln Ala Pro Gly Lys Glu Arg Glu Ala Val
        35                  40                  45

Ser Cys Thr Ser Ala Lys Asp Gly Ser Thr Tyr Tyr Arg Asp Ser Val
50                  55                  60

Arg Gly Arg Phe Thr Ile Ser Arg Asp Asp Gly Lys Asn Thr Val Tyr
65                  70                  75                  80

Leu Gln Met Asn Arg Leu Lys Pro Glu Asp Thr Ala Val Tyr Tyr Cys
                85                  90                  95

Ala Thr Thr Asp Cys Asp Ala Thr Ser Trp Gly Thr Trp Ile Asn Tyr
            100                 105                 110

Tyr Gly Gln Gly Thr Gln Val Thr Val Ser Ser
        115                 120

<210> SEQ ID NO 2
<211> LENGTH: 123
<212> TYPE: PRT
<213> ORGANISM: Lama glama
<220> FEATURE:
<221> NAME/KEY: MISC_FEATURE
<223> OTHER INFORMATION: 3B4
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
```

```
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 2

Gln Val Gln Leu Gln Glu Ser Gly Gly Gly Ser Ala Gln Pro Gly Gly
1               5                   10                  15

Ser Leu Arg Leu Ser Cys Ala Ala Ser Gly Phe Ser Leu Arg Asn Phe
            20                  25                  30

Gly Ile Gly Trp Phe Arg Gln Ala Pro Gly Lys Glu Arg Glu Gly Val
        35                  40                  45

Ser Cys Ser Asn Val Arg Asp Gly Ser Thr Tyr Tyr Gln Ser Ser Val
50                  55                  60

Lys Gly Arg Phe Thr Ile Tyr Arg Asp Asn Phe Lys Asn Met Leu Tyr
65                  70                  75                  80

Leu Gln Met Asn Asn Leu Glu Leu Glu Asp Thr Ala Val Tyr Tyr Cys
                85                  90                  95

Ala Thr Thr Asp Cys Glu Ala Thr Ser Trp Gly Thr Tyr Val Gly Tyr
            100                 105                 110

Trp Gly Gln Gly Thr Gln Val Thr Val Ser Ser
        115                 120

<210> SEQ ID NO 3
<211> LENGTH: 123
<212> TYPE: PRT
<213> ORGANISM: Lama glama
<220> FEATURE:
<221> NAME/KEY: MISC_FEATURE
<223> OTHER INFORMATION: 3B7
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 3
```

-continued

Gln Val Gln Leu Gln Glu Ser Gly Gly Gly Leu Val Arg Thr Gly Gly
1               5                   10                  15

Ser Leu Arg Leu Ser Cys Val Ala Ser Gly Phe Ala Leu Ala Asn Tyr
            20                  25                  30

Gly Ile Gly Trp Phe Arg Gln Ala Pro Gly Lys Glu Arg Glu Gly Val
        35                  40                  45

Ser Cys Ser Asn Val Arg Asp Gly Ser Thr Tyr Tyr Arg Asp Ser Val
    50                  55                  60

Lys Gly Arg Phe Thr Ile Ser Arg Asn Asn Ile Glu Asn Thr Val Tyr
65                  70                  75                  80

Leu Gln Met Ser Thr Leu Lys Pro Glu Asp Thr Ala Leu Tyr Tyr Cys
                85                  90                  95

Ala Thr Thr Asp Cys Glu Ala Ser Ser Trp Gly Thr Trp Ile Asn Tyr
                100                 105                 110

Arg Gly Gln Gly Thr Gln Val Thr Val Ser Ser
            115                 120

<210> SEQ ID NO 4
<211> LENGTH: 123
<212> TYPE: PRT
<213> ORGANISM: Lama glama
<220> FEATURE:
<221> NAME/KEY: MISC_FEATURE
<223> OTHER INFORMATION: 3D10
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 4

Gln Val Gln Leu Gln Glu Ser Gly Gly Gly Leu Val Gln Pro Gly Gly
1               5                   10                  15

Ser Leu Thr Leu Ser Cys Glu Ala Ser Gly Phe Arg Leu Arg Asn Phe
            20                  25                  30

Gly Ile Gly Trp Phe Arg Gln Ala Ala Gly Lys Glu Arg Glu Gly Val
        35                  40                  45

Ser Cys Ser Asn Val Arg Asp Gly Thr Thr Tyr Tyr Ala Asp Ala Val
    50                  55                  60

Lys Gly Arg Phe Ile Ile Ser Arg Asp Asn Thr Arg Asn Thr Leu Ser
65                  70                  75                  80

Leu Gln Met Asn Ser Leu Lys Pro Glu Asp Thr Ala Val Tyr Ser Cys
                85                  90                  95

Gly Thr Thr Asp Cys Glu Ala Ser His Trp Gly Thr Tyr Val Gly Tyr
            100                 105                 110

Phe Gly His Gly Thr Gln Val Thr Val Ser Ser
            115                 120

<210> SEQ ID NO 5
<211> LENGTH: 123
<212> TYPE: PRT
<213> ORGANISM: Lama glama
<220> FEATURE:
<221> NAME/KEY: MISC_FEATURE
<223> OTHER INFORMATION: 3D2
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 5

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Pro Leu Val Leu Tyr
            20                  25                  30

Gly Met Gly Trp Phe Arg Gln Ala Pro Gly Lys Lys Arg Glu Ala Val
            35                  40                  45

Ser Cys Ser Ser Val Asn Asp Gly Gly Thr Tyr Tyr Ala Glu Ser Val
        50                  55                  60

Glu Gly Arg Phe Thr Leu Phe Arg Asp Asn Gly Ala Asn Ala Leu Tyr
65                  70                  75                  80

Leu Gln Met Asn Ser Leu Glu Pro Glu Asp Thr Ala Val Tyr Tyr Cys
                85                  90                  95

Ala Thr Thr Asp Cys Glu Ala Thr Gly Trp Gly Thr Trp Thr Asn Tyr
            100                 105                 110

Arg Gly Gln Gly Thr Gln Val Thr Val Ser Ser
            115                 120

<210> SEQ ID NO 6
<211> LENGTH: 123
<212> TYPE: PRT
<213> ORGANISM: Lama glama
<220> FEATURE:
<221> NAME/KEY: MISC_FEATURE
<223> OTHER INFORMATION: 3D8
<220> FEATURE:
<221> NAME/KEY: MISC_FEATURE

```
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: FR3
<220> FEATURE:
<221> NAME/KEY: MISC_FEATURE
<222> LOCATION: (113)..(123)
<223> OTHER INFORMATION: FR4

<400> SEQUENCE: 6

Gln Val Gln Leu Gln Glu Ser Gly Gly Gly Leu Val Gln Pro Gly Gly
1               5                   10                  15

Pro Leu Arg Leu Ser Cys Ala Ala Ser Gly Phe Ser Val Ala Tyr Tyr
            20                  25                  30

Gly Met Gly Trp Phe Arg Gln Ala Pro Gly Lys Glu Arg Glu Gly Val
        35                  40                  45

Ala Cys Ile Ser Ala Leu Arg Asp Thr Thr Tyr Tyr Thr Asp Ser Val
    50                  55                  60

Lys Gly Arg Phe Thr Leu Ser Arg Asp Asn Val Lys Asn Thr Leu Ser
65                  70                  75                  80

Leu Gln Met Asn Ser Leu Lys Pro Glu Asp Thr Gly Val Tyr Tyr Cys
                85                  90                  95

Ala Thr Thr Asp Cys Asp Ala Thr Ser Arg Met Thr Tyr Leu Ser Tyr
            100                 105                 110

Leu Gly Gln Gly Thr Gln Val Thr Val Ser Ser
        115                 120

<210> SEQ ID NO 7
<211> LENGTH: 123
<212> TYPE: PRT
<213> ORGANISM: Lama glama
<220> FEATURE:
<221> NAME/KEY: MISC_FEATURE
<223> OTHER INFORMATION: 3E6
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
```

-continued

```
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 7

Gln Val Gln Leu Gln Glu Ser Gly Gly Gly Leu Val Gln Pro Gly Gly
1               5                   10                  15

Thr Leu Ser Leu Ser Cys Ala Ala Ser Gly Phe Asn Val Arg Trp Tyr
            20                  25                  30

Gly Met Gly Trp Phe Arg Gln Ala Pro Gly Lys Glu Arg Glu Gly Val
        35                  40                  45

Ala Cys Ile Ser Ala Leu Gln Glu Thr Thr Ala Tyr Ala Asp Ser Val
    50                  55                  60

Lys Gly Arg Phe Thr Leu Ser Arg Asp Asn Pro Lys Asn Thr Leu Ser
65                  70                  75                  80

Leu Gln Met Asn Asn Leu Gln Pro Glu Asp Thr Gly Val Tyr Tyr Cys
                85                  90                  95

Ala Thr Thr Asp Cys Asp Asp Ser Ser Arg Met Thr Tyr Thr Ser Tyr
            100                 105                 110

Leu Gly Gln Gly Thr Gln Val Thr Val Ser Ser
        115                 120

<210> SEQ ID NO 8
<211> LENGTH: 123
<212> TYPE: PRT
<213> ORGANISM: Lama glama
<220> FEATURE:
<221> NAME/KEY: MISC_FEATURE
<223> OTHER INFORMATION: 3F5
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 8

Gln Val Gln Leu Gln Glu Ser Gly Gly Gly Leu Val Gln Pro Gly Arg
1               5                   10                  15

Ser Leu Lys Val Ala Cys Ala Ala Val Gly Phe Ser Leu Arg Asn Tyr
            20                  25                  30
```

```
Gly Ile Gly Trp Phe Arg Gln Val Pro Gly Lys Ala Arg Glu Ala Val
            35                  40                  45

Ser Cys Thr Ser Val Asn Asp Gly Ser Thr His Tyr Gly Asp Ser Val
 50                      55                  60

Arg Gly Arg Phe Ser Ile Ala Arg Asp Asn Ser Lys Asn Thr Val Phe
 65                  70                  75                  80

Leu Gln Met Asn Asp Leu Lys Pro Glu Asp Thr Ala Val Tyr Phe Cys
                85                  90                  95

Ala Thr Thr Asp Cys Asp Val Thr Ser Trp Gly Thr Trp Ile Asn Tyr
            100                 105                 110

Tyr Gly Gln Gly Thr Gln Val Thr Val Ser Ser
            115                 120
```

<210> SEQ ID NO 9
<211> LENGTH: 123
<212> TYPE: PRT
<213> ORGANISM: Lama glama
<220> FEATURE:
<221> NAME/KEY: MISC_FEATURE
<223> OTHER INFORMATION: 3F7
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 9

```
Gln Val Gln Leu Gln Glu Ser Gly Gly Gly Leu Val Arg Thr Gly Gly
 1               5                  10                  15

Ser Leu Arg Leu Ser Cys Val Ala Ser Gly Phe Ala Leu Ala Asn Tyr
                20                  25                  30

Gly Ile Gly Trp Phe Arg Gln Ala Pro Gly Lys Gly Arg Glu Gly Val
            35                  40                  45

Ser Cys Ser Asn Val Arg Asp Gly Ser Thr Tyr Tyr Arg Asp Ser Val
 50                      55                  60

Lys Gly Arg Phe Thr Ile Ser Arg Asn Asn Ile Glu Asn Thr Val Tyr
 65                  70                  75                  80

Leu Gln Met Ser Thr Leu Lys Pro Glu Asp Thr Ala Leu Tyr Tyr Cys
                85                  90                  95

Ala Thr Thr Asp Cys Glu Ala Ser Ser Trp Gly Thr Trp Ile Asn Tyr
            100                 105                 110

Arg Gly Gln Gly Thr Gln Val Thr Val Ser Ser
```

-continued

```
            115                 120

<210> SEQ ID NO 10
<211> LENGTH: 123
<212> TYPE: PRT
<213> ORGANISM: Lama glama
<220> FEATURE:
<221> NAME/KEY: MISC_FEATURE
<223> OTHER INFORMATION: 3F9
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 10

Gln Val Gln Leu Gln Glu Ser Gly Gly Gly Leu Val Gln Pro Gly Gly
1               5                   10                  15

Pro Leu Lys Leu Ser Cys Ala Ala Ser Gly Phe Ser Val Ala Tyr Tyr
            20                  25                  30

Gly Met Gly Trp Phe Arg Gln Ala Pro Gly Lys Glu Arg Glu Gly Val
        35                  40                  45

Ala Cys Ile Ser Ala Leu Arg Asn Thr Thr Tyr Tyr Thr Asp Ser Val
    50                  55                  60

Gln Gly Arg Phe Thr Leu Ser Arg Asp Asn Val Lys Asn Thr Leu Ser
65                  70                  75                  80

Leu Gln Met Asn Ser Leu Lys Pro Glu Asp Thr Gly Val Tyr Tyr Cys
                85                  90                  95

Ala Thr Thr Asp Cys Asp Thr Thr Ser Arg Met Thr Tyr Leu Ser Tyr
            100                 105                 110

Leu Gly Gln Gly Thr Gln Val Thr Val Ser Ser
        115                 120

<210> SEQ ID NO 11
<211> LENGTH: 123
<212> TYPE: PRT
<213> ORGANISM: Lama glama
<220> FEATURE:
<221> NAME/KEY: MISC_FEATURE
<223> OTHER INFORMATION: 3G2
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
```

<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 11

Gln Val Gln Leu Gln Glu Ser Gly Gly Gly Ser Val Gln Pro Gly Gly
1               5                   10                  15

Ser Leu Thr Leu Ser Cys Leu Ala Ser Gly Phe Ser Leu Ser Asn Tyr
            20                  25                  30

Gly Met Gly Trp Phe Arg Gln Ala Pro Gly Lys Glu Arg Glu Gly Val
        35                  40                  45

Ser Cys Thr Ser Ser Pro Ser Gly His Thr Tyr Tyr Ala Asp Ser Val
    50                  55                  60

Lys Gly Arg Phe Thr Ile Val Arg Asp Asn Ala Gly Asn Ser Val Tyr
65                  70                  75                  80

Leu Gln Met Asn Ser Leu Lys Pro Glu Asp Ala Ala Val Tyr Phe Cys
                85                  90                  95

Ala Thr Thr Asp Cys Glu Ala Ala His Trp Gly Thr Trp Val Asn Tyr
            100                 105                 110

Tyr Gly Gln Gly Thr Gln Val Thr Val Ser Ser
        115                 120

<210> SEQ ID NO 12
<211> LENGTH: 123
<212> TYPE: PRT
<213> ORGANISM: Lama glama
<220> FEATURE:
<221> NAME/KEY: MISC_FEATURE
<223> OTHER INFORMATION: 3G4
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3

```
<220> FEATURE:
<221> NAME/KEY: MISC_FEATURE
<222> LOCATION: (113)..(123)
<223> OTHER INFORMATION: FR4

<400> SEQUENCE: 12

Gln Val Gln Leu Gln Glu Ser Gly Gly Gly Leu Val Gln Pro Gly Gly
1               5                   10                  15

Ser Leu Arg Leu Ser Cys Ala Thr Ser Gly Phe Pro Leu Arg Val Tyr
            20                  25                  30

Gly Val Gly Trp Phe Arg Gln Ala Pro Gly Lys Glu Arg Glu Gly Val
        35                  40                  45

Ser Cys Ser Ser Val His Gly Ala Arg Ile His Tyr Ala Asp Ser Val
    50                  55                  60

Lys Gly Arg Phe Thr Ile Ser Arg Asp Asn Ala Lys Asn Thr Val Phe
65                  70                  75                  80

Leu Glu Met Asn Asp Leu Lys Pro Glu Asp Thr Ala Val Tyr Tyr Cys
                85                  90                  95

Ala Thr Thr Asp Cys Glu Ala Thr Ser Trp Gly Thr Tyr Ile Ser Trp
            100                 105                 110

His Gly Gln Gly Thr Gln Val Thr Val Ser Ser
        115                 120

<210> SEQ ID NO 13
<211> LENGTH: 123
<212> TYPE: PRT
<213> ORGANISM: Lama glama
<220> FEATURE:
<221> NAME/KEY: MISC_FEATURE
<223> OTHER INFORMATION: 3H10
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 13

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Leu Arg Asn Tyr
            20                  25                  30

Gly Ile Gly Trp Phe Arg Gln Ala Pro Gly Lys Glu Arg Glu Gly Val
        35                  40                  45

Ser Cys Ser Asn Val Arg Asp Gly Ser Ile Tyr Tyr Ala Asp Ser Val
```

```
                       50                  55                  60
Gln Gly Arg Phe Thr Ile Ser Arg Val Asn Val Lys Asn Thr Leu Tyr
 65                  70                  75                  80

Leu Gln Met Asn Asp Leu Arg Pro Glu Asp Thr Ala Val Tyr Tyr Cys
                 85                  90                  95

Ala Thr Thr Asp Cys Glu Ala Thr Gly Trp Gly Thr Trp Ile Gly Tyr
            100                 105                 110

Phe Gly Gln Gly Thr Gln Val Thr Val Ser Ser
            115                 120

<210> SEQ ID NO 14
<211> LENGTH: 123
<212> TYPE: PRT
<213> ORGANISM: Lama glama
<220> FEATURE:
<221> NAME/KEY: MISC_FEATURE
<223> OTHER INFORMATION: 3H8
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 14

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Pro Leu Val Leu Tyr
             20                  25                  30

Gly Met Gly Trp Phe Arg Gln Ala Pro Gly Lys Lys Arg Glu Ala Val
             35                  40                  45

Ser Cys Ser Ser Val Asn Asp Gly Thr Tyr Tyr Ala Glu Ser Val
 50                  55                  60

Lys Gly Arg Phe Thr Leu Phe Arg Asp Asn Gly Ala Asn Ala Leu Tyr
 65                  70                  75                  80

Leu Gln Met Asn Ser Leu Glu Pro Glu Asp Thr Ala Val Tyr Tyr Cys
                 85                  90                  95

Ala Thr Thr Asp Cys Glu Ala Thr Gly Trp Gly Thr Trp Thr Asn Tyr
            100                 105                 110

Arg Gly Gln Gly Thr Gln Val Thr Val Ser Ser
            115                 120

<210> SEQ ID NO 15
<211> LENGTH: 123
```

```
<212> TYPE: PRT
<213> ORGANISM: Lama glama
<220> FEATURE:
<221> NAME/KEY: MISC_FEATURE
<223> OTHER INFORMATION: 4A1
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 15

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Ser Leu Arg Tyr Phe
            20                  25                  30

Gly Ile Gly Trp Phe Arg Gln Ala Ala Gly Lys Glu Arg Glu Gly Val
        35                  40                  45

Ser Cys Ser Asn Val Arg Asp Gly Ser Thr Tyr Tyr Ala Asp Ser Val
    50                  55                  60

Lys Gly Arg Phe Thr Ile Ser Arg Asp Asn Val Arg Asn Met Leu Tyr
65                  70                  75                  80

Leu Gln Met Asn Ser Leu Lys Pro Glu Asp Thr Ala Val Tyr Ser Cys
                85                  90                  95

Ala Thr Thr Asp Cys Glu Ala Ala Asn Trp Gly Thr Tyr Val Ser Tyr
            100                 105                 110

Tyr Gly Arg Gly Thr Gln Val Thr Val Ser Ser
            115                 120

<210> SEQ ID NO 16
<211> LENGTH: 123
<212> TYPE: PRT
<213> ORGANISM: Lama glama
<220> FEATURE:
<221> NAME/KEY: MISC_FEATURE
<223> OTHER INFORMATION: 5B5
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: FR2
```

```
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 16

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Leu Val Tyr Tyr
            20                  25                  30

Gly Ile Gly Trp Phe Arg Gln Ala Pro Gly Lys Glu Arg Glu Gly Val
        35                  40                  45

Ser Cys Ser Ser Val His Asp Gly Ser Thr Tyr Tyr Ala Glu Ser Val
50                  55                  60

Lys Gly Arg Phe Thr Ile Ser Arg Asp Asn Ala Lys Asn Thr Leu Tyr
65                  70                  75                  80

Leu Gln Met Asn Asn Leu Lys Pro Glu Asp Thr Ala Val Tyr Tyr Cys
                85                  90                  95

Ala Thr Thr Asp Cys Glu Ala Thr Gly Trp Gly Thr Trp Thr Asn Tyr
            100                 105                 110

Arg Gly Gln Gly Thr Gln Val Thr Val Ser Ser
        115                 120

<210> SEQ ID NO 17
<211> LENGTH: 123
<212> TYPE: PRT
<213> ORGANISM: Lama glama
<220> FEATURE:
<221> NAME/KEY: MISC_FEATURE
<223> OTHER INFORMATION: 5B6
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4
```

-continued

<400> SEQUENCE: 17

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Leu Val Ser Phe
            20                  25                  30

Gly Ile Gly Trp Phe Arg Gln Ala Ala Gly Lys Glu Arg Glu Gly Val
        35                  40                  45

Ser Cys Ser Asn Val Arg Asp Gly Ser Thr Tyr Tyr Ala Asp Ser Val
    50                  55                  60

Lys Gly Arg Phe Thr Ile Ser Arg Asp Asn Val Arg Asn Gln Leu Tyr
65                  70                  75                  80

Leu Gln Met Asn Ser Leu Lys Pro Glu Asp Thr Ala Val Tyr Ser Cys
                85                  90                  95

Ala Thr Thr Asp Cys Glu Ala Thr Ser Trp Gly Thr Tyr Arg Gly Tyr
            100                 105                 110

Phe Gly Gln Gly Thr Gln Val Thr Val Ser Ser
        115                 120

<210> SEQ ID NO 18
<211> LENGTH: 123
<212> TYPE: PRT
<213> ORGANISM: Lama glama
<220> FEATURE:
<221> NAME/KEY: MISC_FEATURE
<223> OTHER INFORMATION: 5C4
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 18

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Leu Arg Tyr Phe
            20                  25                  30

Gly Ile Gly Trp Phe Arg Gln Val Ala Gly Lys Glu Arg Glu Pro Val
        35                  40                  45

Ser Cys Ser Asn Val Arg Asp Gly Asn Thr Tyr Tyr Ala Asp Ser Val
    50                  55                  60

Lys Gly Arg Phe Thr Ile Ser Arg Asp Asn Val Arg Asn Thr Leu Tyr
65                  70                  75                  80

Leu Gln Met Asn Ser Leu Lys Pro Glu Asp Thr Ala Val Tyr Ser Cys
            85                  90                  95

Ala Thr Thr Asp Cys Glu Ala Thr Thr Trp Gly Thr Tyr Arg Gly Tyr
            100                 105                 110

Phe Gly Gln Gly Thr Gln Val Thr Val Ser Ser
            115                 120

<210> SEQ ID NO 19
<211> LENGTH: 123
<212> TYPE: PRT
<213> ORGANISM: Lama glama
<220> FEATURE:
<221> NAME/KEY: MISC_FEATURE
<223> OTHER INFORMATION: 5C5
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 19

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Leu Arg Asn Tyr
            20                  25                  30

Gly Ile Gly Trp Phe Arg Gln Ala Pro Gly Lys Glu Arg Glu Gly Val
            35                  40                  45

Ser Cys Ser Asn Val Arg Asp Gly Ser Ile Tyr Tyr Ala Asp Ser Val
        50                  55                  60

Gln Gly Arg Leu Thr Ile Ser Arg Val Asn Val Lys Asn Thr Leu Tyr
65                  70                  75                  80

Leu Gln Met Asn Asp Leu Arg Pro Glu Asp Thr Ala Val Tyr Tyr Cys
            85                  90                  95

Ala Thr Thr Asp Cys Glu Ala Thr Gly Trp Gly Thr Trp Ile Gly Tyr
            100                 105                 110

Phe Gly Gln Gly Thr Gln Val Thr Val Ser Ser
            115                 120

<210> SEQ ID NO 20
<211> LENGTH: 123
<212> TYPE: PRT
<213> ORGANISM: Lama glama
<220> FEATURE:
<221> NAME/KEY: MISC_FEATURE
<223> OTHER INFORMATION: 5D4

```
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 20

Gln Val Gln Leu Gln Glu Ser Gly Gly Leu Val Gln Pro Gly Gly
 1               5                  10                  15

Ser Leu Arg Leu Ser Cys Ala Ala Ser Gly Phe Asp Met Arg Arg Phe
            20                  25                  30

Gly Ile Gly Trp Phe Arg Gln Val Ala Gly Lys Glu Arg Glu Gly Val
        35                  40                  45

Ser Cys Ser Asn Val His Asp Gly Thr Thr Tyr Tyr Thr Asn Asp Val
    50                  55                  60

Lys Gly Arg Phe Thr Ile Val Arg Asp Asn Thr Lys Asn Met Leu Tyr
65                  70                  75                  80

Leu Gln Met Asn Lys Leu Arg Pro Glu Asp Thr Ala Val Tyr Ser Cys
                85                  90                  95

Ala Thr Thr Asp Cys Glu Ala Thr Ala Trp Gly Thr Tyr Arg Gly Tyr
            100                 105                 110

Phe Gly Gln Gly Thr Gln Val Thr Val Ser Ser
        115                 120

<210> SEQ ID NO 21
<211> LENGTH: 123
<212> TYPE: PRT
<213> ORGANISM: Lama glama
<220> FEATURE:
<221> NAME/KEY: MISC_FEATURE
<223> OTHER INFORMATION: 5E5
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
```

```
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 21
```

Gln Val Gln Leu Gln Glu Ser Gly Gly Gly Leu Val Gln Pro Gly Gly
1               5                   10                  15

Ser Leu Thr Leu Ser Cys Thr Ala Ser Gly Phe Ala Met Arg Arg Phe
            20                  25                  30

Gly Ile Gly Trp Phe Arg Gln Val Gly Lys Glu Arg Glu Gly Val
        35                  40                  45

Ser Cys Ser Asn Val His Asp Gly Ser Thr Tyr Tyr Ala Asn Tyr Val
    50                  55                  60

Lys Gly Arg Phe Thr Ile Val Arg Asp Asp Thr Lys Asn Met Leu Tyr
65                  70                  75                  80

Leu His Met Asn Ser Leu Arg Ala Glu Asp Thr Gly Val Tyr Ser Cys
                85                  90                  95

Ala Thr Thr Asp Cys Glu Ala Thr Ala Trp Gly Thr Tyr Arg Gly Tyr
            100                 105                 110

Phe Gly Gln Gly Thr Gln Val Thr Val Ser Ser
        115                 120

```
<210> SEQ ID NO 22
<211> LENGTH: 123
<212> TYPE: PRT
<213> ORGANISM: Lama glama
<220> FEATURE:
<221> NAME/KEY: MISC_FEATURE
<223> OTHER INFORMATION: 5F5
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 22
```

Gln Val Gln Leu Gln Glu Ser Gly Gly Gly Leu Val Gln Pro Gly Gly
1               5                   10                  15

```
Ser Leu Arg Leu Ser Cys Ala Ala Ser Gly Phe Pro Leu Gly Leu Tyr
            20                  25                  30

Gly Ile Gly Trp Phe Arg Gln Ala Pro Gly Lys Glu Arg Glu Ala Val
            35                  40                  45

Ser Cys Asp Ser Val Asp Asp Gly Ser Thr Asn Tyr Leu Asp Ser Val
        50                  55                  60

Lys Gly Arg Phe Thr Ile Ser Arg Asp Asn Ala Lys Asn Met Val Tyr
 65                  70                  75                  80

Leu Gln Met Asn Ser Leu Lys Pro Glu Asp Thr Ala Val Tyr Tyr Cys
                85                  90                  95

Ala Thr Thr Asp Cys Asp Ala Lys Ala Trp Gly Thr Trp Thr Asn Tyr
            100                 105                 110

Arg Gly Gln Gly Thr Gln Val Thr Val Ser Ser
            115                 120
```

<210> SEQ ID NO 23
<211> LENGTH: 123
<212> TYPE: PRT
<213> ORGANISM: Lama glama
<220> FEATURE:
<221> NAME/KEY: MISC_FEATURE
<223> OTHER INFORMATION: 5G2
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 23

```
Gln Val Gln Leu Gln Glu Ser Gly Gly Gly Leu Val Arg Thr Gly Gly
 1               5                  10                  15

Ser Leu Arg Leu Ser Cys Val Ala Ser Gly Phe Ala Leu Ala Asn Tyr
            20                  25                  30

Gly Ile Gly Trp Phe Arg Gln Ala Pro Gly Lys Glu Arg Glu Gly Val
            35                  40                  45

Ser Cys Ser Asn Val Arg Asp Gly Ser Thr Tyr Tyr Arg Asp Ser Val
        50                  55                  60

Lys Gly Arg Phe Thr Ile Ser Arg Asn Asn Ile Glu Asn Thr Val Tyr
 65                  70                  75                  80

Leu Gln Met Ser Thr Leu Arg Pro Glu Asp Thr Ala Leu Tyr Tyr Cys
                85                  90                  95

Ala Thr Thr Asp Cys Glu Ala Ser Ser Trp Gly Thr Trp Ile Asn Tyr
            100                 105                 110
```

```
Arg Gly Gln Gly Thr Gln Val Thr Val Ser Ser
        115                 120

<210> SEQ ID NO 24
<211> LENGTH: 123
<212> TYPE: PRT
<213> ORGANISM: Lama glama
<220> FEATURE:
<221> NAME/KEY: MISC_FEATURE
<223> OTHER INFORMATION: 5G5
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 24

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Leu Arg Tyr Phe
            20                  25                  30

Gly Ile Gly Trp Phe Arg Gln Ala Ala Gly Lys Glu Arg Glu Gly Ile
        35                  40                  45

Ser Cys Ser Asn Val Arg Asp Gly Asn Thr Tyr Tyr Ala Asp Ser Val
    50                  55                  60

Lys Gly Arg Phe Thr Ile Ser Arg Asp Asn Val Arg Asn Met Leu Tyr
65                  70                  75                  80

Leu Gln Met Asn Asn Leu Lys Pro Asp Asp Thr Ala Val Tyr Ser Cys
                85                  90                  95

Ala Thr Thr Asp Cys Glu Ala Thr Thr Trp Gly Thr Tyr Arg Gly Tyr
            100                 105                 110

Phe Gly Gln Gly Thr Gln Val Thr Val Ser Ser
        115                 120

<210> SEQ ID NO 25
<211> LENGTH: 123
<212> TYPE: PRT
<213> ORGANISM: Lama glama
<220> FEATURE:
<221> NAME/KEY: MISC_FEATURE
<223> OTHER INFORMATION: 5H5
<220> FEATURE:
<221> NAME/KEY: MISC_FEATURE
<222> LOCATION: (1)..(30)
<223> OTHER INFORMATION: FR1
<220> FEATURE:
```

-continued

```
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 25

Gln Val Gln Leu Gln Glu Ser Gly Gly Gly Leu Val Gln Pro Gly Gly
 1               5                   10                  15

Ser Leu Arg Leu Ser Cys Ala Ala Glu Gly Phe Ala Leu Ala Asn Tyr
            20                  25                  30

Gly Val Gly Trp Phe Arg Gln Ala Pro Gly Lys Gly Arg Glu Arg Ile
        35                  40                  45

Ser Cys Ser Ser Val Arg Asp Asn Gly Pro Tyr Tyr Ala Glu Ser Val
    50                  55                  60

Lys Gly Arg Ser Thr Ile Ser Arg Arg Asn Ala Glu Asn Thr Leu Tyr
65                  70                  75                  80

Leu His Met Ser Asn Leu Lys Ala Glu Asp Thr Ala Leu Tyr Tyr Cys
                85                  90                  95

Ala Thr Thr Asp Cys Asp Ala Thr Gly Trp Gly Thr Trp Thr Asn Tyr
            100                 105                 110

Arg Gly Gln Gly Thr Gln Val Thr Val Ser Ser
        115                 120

<210> SEQ ID NO 26
<211> LENGTH: 123
<212> TYPE: PRT
<213> ORGANISM: Lama glama
<220> FEATURE:
<221> NAME/KEY: MISC_FEATURE
<223> OTHER INFORMATION: 7A2
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
```

```
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 26
```

Gln Val Gln Leu Gln Glu Ser Gly Gly Gly Ser Val His Pro Gly Gly
1               5                   10                  15

Ser Leu Thr Leu Ser Cys Leu Ala Ser Gly Phe Ser Leu Ser Asn Tyr
            20                  25                  30

Gly Met Gly Trp Phe Arg Gln Ala Pro Gly Lys Glu Arg Glu Ala Val
        35                  40                  45

Ser Cys Thr Ser Val Pro Asn Gly His Ile Tyr Tyr Ala Glu Ser Val
    50                  55                  60

Lys Gly Arg Phe Thr Ile Val Arg Asp Asn Ala Gly Asn Ser Val Tyr
65                  70                  75                  80

Leu Gln Met Asn Ser Leu Lys Pro Glu Asp Ala Ala Asn Tyr Phe Cys
                85                  90                  95

Ala Thr Thr Asp Cys Glu Ala Ala His Trp Gly Thr Trp Val Asn Tyr
            100                 105                 110

Tyr Gly Gln Gly Thr Gln Val Thr Val Ser Ser
        115                 120

```
<210> SEQ ID NO 27
<211> LENGTH: 123
<212> TYPE: PRT
<213> ORGANISM: Lama glama
<220> FEATURE:
<221> NAME/KEY: MISC_FEATURE
<223> OTHER INFORMATION: 7C2
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 27
```

Gln Val Gln Leu Gln Glu Ser Gly Gly Gly Leu Val Gln Pro Gly Gly
1               5                   10                  15

Ser Leu Arg Leu Ser Cys Ala Ala Phe Gly Phe Ala Leu Ala Asn Tyr
            20                  25                  30

Gly Ile Gly Trp Phe Arg Gln Ala Pro Gly Lys Asp Arg Glu Arg Val
        35                  40                  45

```
Ser Cys Asp Ser Val Asp Asp Gly Ser Thr His Tyr Ser Asn Ser Val
    50                  55                  60

Gln Gly Arg Phe Thr Ile Ile Arg Asp Asn Ala Lys Asn Thr Val Phe
65                  70                  75                  80

Leu Gln Met Asn Ser Leu Lys Ala Glu Asp Thr Ala Val Tyr Tyr Cys
                85                  90                  95

Ala Thr Thr Asp Cys Asp Ala Thr Thr Trp Gly Thr Trp Ile Asn Tyr
                100                 105                 110

Arg Gly Gln Gly Thr Gln Val Thr Val Ser Ser
            115                 120
```

```
<210> SEQ ID NO 28
<211> LENGTH: 123
<212> TYPE: PRT
<213> ORGANISM: Lama glama
<220> FEATURE:
<221> NAME/KEY: MISC_FEATURE
<223> OTHER INFORMATION: 7D2
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 28

Gln Val Gln Leu Gln Glu Ser Gly Gly Leu Val Gln Pro Gly Arg
1               5                   10                  15

Ser Leu Lys Val Ala Cys Ala Ala Gly Phe Ser Leu Arg Tyr Tyr
                20                  25                  30

Gly Ile Gly Trp Phe Arg Gln Ala Pro Gly Lys Glu Arg Glu Ala Val
            35                  40                  45

Ser Cys Thr Ser Ala Asn Asp Gly Ser Thr Tyr Tyr Arg Asp Ser Val
    50                  55                  60

Arg Gly Arg Phe Thr Ile Ser Arg Asp Asp Gly Lys Asn Thr Val Tyr
65                  70                  75                  80

Leu Gln Met Asn Arg Leu Lys Pro Glu Asp Thr Ala Val Tyr Tyr Cys
                85                  90                  95

Ala Thr Thr Asp Cys Asp Ala Thr Ser Trp Gly Thr Trp Ile Asn Tyr
                100                 105                 110

Tyr Gly Gln Gly Thr Gln Val Thr Val Ser Ser
            115                 120
```

```
<210> SEQ ID NO 29
<211> LENGTH: 123
<212> TYPE: PRT
<213> ORGANISM: Lama glama
<220> FEATURE:
<221> NAME/KEY: MISC_FEATURE
<223> OTHER INFORMATION: 7E1_1
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 29

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Gly Met Gly Trp Phe Arg Gln Ala Pro Gly Lys Gly Arg Glu Arg Ile
        35                  40                  45

Ser Cys Ser Ser Val Arg Asp Asn Gly Pro Tyr Tyr Ala Glu Ser Val
    50                  55                  60

Lys Gly Arg Ser Thr Ile Ser Arg Arg Asn Thr Glu Asn Thr Leu Tyr
65                  70                  75                  80

Leu His Met Ser Asn Leu Lys Ala Glu Asp Thr Ala Leu Tyr Tyr Cys
                85                  90                  95

Ala Thr Thr Asp Cys Asp Ala Thr Gly Trp Gly Thr Trp Thr Asn Tyr
            100                 105                 110

Arg Gly Gln Gly Thr Gln Val Thr Val Ser Ser
        115                 120

<210> SEQ ID NO 30
<211> LENGTH: 123
<212> TYPE: PRT
<213> ORGANISM: Lama glama
<220> FEATURE:
<221> NAME/KEY: MISC_FEATURE
<223> OTHER INFORMATION: 7F1
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
```

<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 30

Gln Val Gln Leu Gln Glu Ser Gly Gly Gly Leu Val Gln Ala Gly Arg
1               5                   10                  15

Ser Leu Glu Val Ala Cys Ala Ala His Gly Phe Ser Leu Arg Asn Tyr
            20                  25                  30

Gly Ile Gly Trp Phe Arg Gln Val Pro Gly Lys Ala Arg Glu Ala Val
        35                  40                  45

Ser Cys Thr Ser Val Asn Asp Gly Thr Thr His Tyr Gly Asp Ser Val
    50                  55                  60

Arg Gly Arg Phe Ser Ile Ala Arg Asp Asn Ala Lys Asn Thr Val Phe
65                  70                  75                  80

Leu Gln Met Asn Asp Leu Lys Pro Glu Asp Thr Ala Val Tyr Phe Cys
                85                  90                  95

Ala Thr Thr Asp Cys Asp Ala Thr Ser Trp Gly Thr Trp Ile Asn Tyr
            100                 105                 110

Tyr Gly Gln Gly Thr Gln Val Thr Val Ser Ser
        115                 120

<210> SEQ ID NO 31
<211> LENGTH: 123
<212> TYPE: PRT
<213> ORGANISM: Lama glama
<220> FEATURE:
<221> NAME/KEY: MISC_FEATURE
<223> OTHER INFORMATION: 8B10
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)

-continued

<223> OTHER INFORMATION: FR4

<400> SEQUENCE: 31

Gln Val Gln Leu Gln Glu Ser Gly Gly Gly Leu Val Gln Pro Gly Gly
1               5                   10                  15

Ser Leu Arg Leu Ser Cys Val Ala Ser Gly Phe Pro Leu Gly Leu Tyr
            20                  25                  30

Gly Met Gly Trp Phe Arg Gln Ala Pro Gly Lys Glu Arg Glu Ala Val
        35                  40                  45

Ser Cys Ser Ser Val His Asp Gly Ser Thr Tyr Tyr Ala Glu Phe Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Arg Pro Glu Asp Ala Ala Val Tyr Tyr Cys
                85                  90                  95

Ala Thr Thr Asp Cys Glu Ala Ser Ser Trp Gly Thr Trp Ile Asn Tyr
            100                 105                 110

Arg Gly Gln Gly Thr Gln Val Thr Val Ser Ser
        115                 120

<210> SEQ ID NO 32
<211> LENGTH: 123
<212> TYPE: PRT
<213> ORGANISM: Lama glama
<220> FEATURE:
<221> NAME/KEY: MISC_FEATURE
<223> OTHER INFORMATION: 8B12
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 32

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Leu Val Tyr Tyr
            20                  25                  30

Gly Ile Gly Trp Phe Arg Gln Ala Pro Gly Lys Glu Arg Glu Gly Val
        35                  40                  45

Ala Cys Ile Ser Ala Leu Arg Asp Thr Thr Tyr Tyr Thr Asp Ser Val
    50                  55                  60

Lys Gly Arg Phe Thr Leu Ser Arg Asp Asn Val Lys Asn Thr Leu Ser

-continued

```
            65                  70                  75                  80
Leu Gln Met Asn Ser Leu Lys Pro Glu Asp Thr Gly Val Tyr Tyr Cys
                    85                  90                  95

Ala Thr Thr Asp Cys Asp Ala Thr Ser Arg Met Thr Tyr Leu Ser Tyr
                100                 105                 110

Leu Gly Gln Gly Thr Gln Val Thr Val Ser Ser
            115                 120
```

<210> SEQ ID NO 33
<211> LENGTH: 123
<212> TYPE: PRT
<213> ORGANISM: Lama glama
<220> FEATURE:
<221> NAME/KEY: MISC_FEATURE
<223> OTHER INFORMATION: 9A1
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 33

```
Gln Val Gln Leu Gln Glu Ser Gly Gly Gly Leu Val Gln Pro Gly Gly
1               5                   10                  15

Pro Leu Arg Leu Ser Cys Thr Ala Ser Gly Phe Asn Ile Phe Tyr Tyr
                20                  25                  30

Gly Met Gly Trp Phe Arg Gln Ala Pro Gly Lys Glu Arg Glu Gly Val
            35                  40                  45

Ala Cys Ile Ser Ala Leu Arg Gln Ser Thr Tyr Tyr Ser Asp Ser Val
        50                  55                  60

Glu Gly Arg Phe Thr Leu Ser Arg Asp Asn Ala Lys Asn Thr Leu Ser
65                  70                  75                  80

Leu Gln Met Asn Ser Leu Lys Pro Glu Asp Thr Gly Val Tyr Phe Cys
                85                  90                  95

Ala Thr Thr Asp Cys Asp Ala Ala Ser Arg Met Thr Tyr Thr Ser Tyr
                100                 105                 110

Arg Gly Gln Gly Thr Gln Val Thr Val Ser Ser
            115                 120
```

<210> SEQ ID NO 34
<211> LENGTH: 123
<212> TYPE: PRT
<213> ORGANISM: Lama glama
<220> FEATURE:

```
<221> NAME/KEY: MISC_FEATURE
<223> OTHER INFORMATION: 9B5
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 34

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Leu Arg Tyr Phe
            20                  25                  30

Gly Ile Gly Trp Phe Arg Gln Ala Ala Gly Lys Glu His Glu Gly Ile
        35                  40                  45

Ser Cys Ser Asn Val Arg Asp Gly Asn Thr Tyr Tyr Ala Asp Ser Val
    50                  55                  60

Lys Gly Arg Phe Thr Ile Ser Arg Asp Asn Val Arg Asn Met Leu Tyr
65                  70                  75                  80

Leu Gln Met Asn Asn Leu Lys Pro Asp Asp Thr Ala Val Tyr Ser Cys
                85                  90                  95

Ala Thr Thr Asp Cys Glu Ala Thr Thr Trp Gly Thr Tyr Arg Gly Tyr
            100                 105                 110

Phe Gly Gln Gly Thr Gln Val Thr Val Ser Ser
        115                 120

<210> SEQ ID NO 35
<211> LENGTH: 123
<212> TYPE: PRT
<213> ORGANISM: Lama glama
<220> FEATURE:
<221> NAME/KEY: MISC_FEATURE
<223> OTHER INFORMATION: 9C4
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
```

```
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 35
```

Gln Val Gln Leu Gln Glu Ser Gly Gly Gly Leu Val His Pro Gly Gly
 1               5                  10                  15

Pro Leu Thr Leu Ser Cys Ala Ala Ser Gly Phe Arg Val Glu Tyr Tyr
             20                  25                  30

Gly Ile Gly Trp Phe Arg Gln Ala Pro Gly Lys Glu Arg Glu Lys Val
         35                  40                  45

Ser Cys Ile Ser Ala Leu His Glu Ser Thr Tyr Tyr Ala Asp Ser Val
 50                  55                  60

Lys Gly Arg Phe Thr Ile Ser Arg Asp Asn Gly Lys Asn Ala Val Tyr
65                  70                  75                  80

Leu Gln Met Asn Ser Leu Lys Pro Glu Asp Thr Gly Val Tyr Tyr Cys
                 85                  90                  95

Ala Thr Thr Asp Cys Asp Ala Thr Ser Trp Gly Thr Trp Asn Tyr
            100                 105                 110

Arg Gly Gln Gly Thr Gln Val Thr Val Ser Ser
        115                 120

```
<210> SEQ ID NO 36
<211> LENGTH: 123
<212> TYPE: PRT
<213> ORGANISM: Lama glama
<220> FEATURE:
<221> NAME/KEY: MISC_FEATURE
<223> OTHER INFORMATION: 9D5
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 36
```

Gln Val Gln Leu Gln Glu Ser Gly Gly Gly Ser Val Gln Pro Gly Gly

```
                   1               5                  10                 15
Ser Leu Thr Leu Ser Cys Val Gly His Gly Phe Gly Val Ala Asn Phe
                    20                 25                 30

Gly Ile Gly Trp Phe Arg Gln Ala Pro Gly Lys Glu Arg Glu Ala Val
                    35                 40                 45

Ser Cys Asp Ser Val Asp Asp Gly Thr Ile Ala Tyr Ala Asp Ser Val
                    50                 55                 60

Lys Gly Arg Phe Thr Leu Phe Arg Asp Asn Tyr Lys Asn Thr Leu Tyr
 65                 70                 75                 80

Leu Gln Met Asn Arg Leu Arg Pro Glu Asp Thr Ala Val Tyr Phe Cys
                    85                 90                 95

Ala Thr Thr Asp Cys Asp Ala Arg Ser Trp Gly Thr Trp Ile Asn Tyr
                   100                105                110

Arg Gly Gln Gly Thr Gln Val Thr Val Ser Ser
                   115                120
```

<210> SEQ ID NO 37
<211> LENGTH: 123
<212> TYPE: PRT
<213> ORGANISM: Lama glama
<220> FEATURE:
<221> NAME/KEY: MISC_FEATURE
<223> OTHER INFORMATION: 9E1
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 37

```
Gln Val Gln Leu Gln Glu Ser Gly Gly Gly Leu Val Gln Pro Gly Gly
 1               5                  10                 15

Ser Leu Arg Leu Ser Cys Glu Ala Ser Gly Phe Arg Leu Arg Asn Phe
                    20                 25                 30

Gly Ile Gly Trp Phe Arg Gln Ala Ala Gly Lys Glu Arg Glu Gly Val
                    35                 40                 45

Ser Cys Ser Asn Val Arg Asp Gly Ser Thr Tyr Tyr Ala Asp Ser Val
                    50                 55                 60

Lys Gly Arg Phe Ile Ile Ser Arg Asp Asn Thr Arg Asn Thr Leu Ser
 65                 70                 75                 80

Leu Gln Met Asn Ser Leu Lys Pro Glu Asp Thr Ala Val Tyr Ser Cys
                    85                 90                 95
```

Gly Thr Thr Asp Cys Glu Ala Thr Gly Trp Gly Thr Tyr Val Gly Tyr
            100                 105                 110

Phe Gly Gln Gly Thr Gln Val Thr Val Ser Ser
        115                 120

<210> SEQ ID NO 38
<211> LENGTH: 123
<212> TYPE: PRT
<213> ORGANISM: Lama glama
<220> FEATURE:
<221> NAME/KEY: MISC_FEATURE
<223> OTHER INFORMATION: 9E4
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 38

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Leu Val Tyr Tyr
            20                  25                  30

Gly Ile Gly Trp Phe Arg Gln Ala Pro Gly Lys Glu Arg Glu Gly Val
        35                  40                  45

Ser Cys Ser Ser Val His Asp Gly Ser Thr Tyr Tyr Ala Glu Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Thr Thr Asp Cys Glu Ala Thr Gly Trp Gly Thr Trp Asn Tyr
            100                 105                 110

Arg Gly Gln Gly Thr Gln Val Thr Val Ser Ser
        115                 120

<210> SEQ ID NO 39
<211> LENGTH: 123
<212> TYPE: PRT
<213> ORGANISM: Lama glama
<220> FEATURE:
<221> NAME/KEY: MISC_FEATURE
<223> OTHER INFORMATION: 9F4
<220> FEATURE:
<221> NAME/KEY: MISC_FEATURE
<222> LOCATION: (1)..(30)

<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 39

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Pro Leu Ser Val Tyr
            20                  25                  30

Gly Ile Gly Trp Phe Arg Leu Ala Pro Gly Lys Glu Arg Glu Gly Val
        35                  40                  45

Ser Cys Ser Ser Val His Asp Gly Ser Thr Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Asn Ser Glu Asp Thr Ala Val Tyr Tyr Cys
                85                  90                  95

Ala Thr Thr Asp Cys Asp Ala Ser Ser Trp Gly Thr Trp Thr Asn Tyr
            100                 105                 110

Arg Gly Gln Gly Thr Gln Val Thr Val Ser Ser
        115                 120

<210> SEQ ID NO 40
<211> LENGTH: 123
<212> TYPE: PRT
<213> ORGANISM: Lama glama
<220> FEATURE:
<221> NAME/KEY: MISC_FEATURE
<223> OTHER INFORMATION: 9H1
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3

-continued

```
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 40

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Asp Met Arg Arg Phe
            20                  25                  30

Gly Ile Gly Trp Phe Arg Gln Val Ala Gly Lys Glu Arg Glu Gly Val
        35                  40                  45

Ser Cys Ser Asn Val His Asp Gly Thr Thr Tyr Tyr Thr Asn Asp Val
    50                  55                  60

Lys Gly Arg Phe Thr Ile Val Arg Asp Asn Thr Lys Asn Met Leu Tyr
65                  70                  75                  80

Leu Gln Met Asn Glu Leu Arg Pro Glu Asp Thr Ala Val Tyr Ser Cys
            85                  90                  95

Ala Thr Thr Asp Cys Glu Ala Thr Ala Trp Gly Thr Tyr Arg Gly Tyr
            100                 105                 110

Phe Gly Gln Gly Thr Gln Val Thr Val Ser Ser
            115                 120

<210> SEQ ID NO 41
<211> LENGTH: 123
<212> TYPE: PRT
<213> ORGANISM: Lama glama
<220> FEATURE:
<221> NAME/KEY: MISC_FEATURE
<223> OTHER INFORMATION: 9H2
<220> FEATURE:
<221> NAME/KEY: MISC_FEATURE
<222> LOCATION: (1)..(30)
<223> OTHER INFORMATION: FR1
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(112)
<223> OTHER INFORMATION: CDR3
<220> FEATURE:
<221> NAME/KEY: MISC_FEATURE
<222> LOCATION: (113)..(123)
<223> OTHER INFORMATION: FR4

<400> SEQUENCE: 41

Gln Val Gln Leu Gln Glu Ser Gly Gly Gly Leu Val Gln Pro Gly Gly
1               5                   10                  15

Leu Leu Arg Leu Ser Cys Ala Ala Ser Gly Phe Ser Val Ala Tyr Tyr
            20                  25                  30
```

```
Gly Met Gly Trp Phe Arg Gln Ala Pro Gly Lys Glu Arg Glu Gly Val
            35                  40                  45

Ala Cys Ile Ser Ala Leu Arg Asp Thr Thr Tyr Tyr Thr Asp Ser Val
 50                  55                  60

Lys Gly Arg Phe Thr Leu Ser Arg Asp Asn Val Lys Asn Thr Leu Ser
 65                  70                  75                  80

Leu Gln Met Asn Ser Leu Lys Pro Glu Asp Thr Gly Val Tyr Tyr Cys
                 85                  90                  95

Ala Thr Thr Asp Cys Asp Ala Thr Ser Arg Met Thr Tyr Leu Ser Tyr
            100                 105                 110

Leu Gly Gln Gly Thr Gln Val Thr Val Ser Ser
        115                 120

<210> SEQ ID NO 42
<211> LENGTH: 124
<212> TYPE: PRT
<213> ORGANISM: Lama glama

<400> SEQUENCE: 42

Gln Val Gln Leu Gln Glu Ser Gly Gly Leu Val Gln Ala Gly Asp
 1               5                   10                  15

Ser Leu Arg Leu Ser Cys Ala Ala Ser Gly Arg Ile Phe Ser Ala Tyr
                 20                  25                  30

Val Val Gly Trp Phe Arg Gln Ala Pro Gly Lys Glu Arg Glu Phe Val
            35                  40                  45

Ala Ala Ile Arg Trp Ser Gly Gly Thr Thr Tyr Ala Asp Ser Val
 50                  55                  60

Lys Gly Arg Phe Thr Ile Ser Arg Asp Asn Ala Gln Asn Thr Val Tyr
 65                  70                  75                  80

Leu Gln Met Asn Ser Leu Lys Pro Glu Asp Thr Ala Ile Tyr Tyr Cys
                 85                  90                  95

Ala Ala Lys Tyr Ser Gly Ser Tyr Tyr Leu Ser Ser Tyr Ala Tyr Asn
            100                 105                 110

Tyr Trp Gly Gln Gly Thr Gln Val Thr Val Ser Ser
        115                 120

<210> SEQ ID NO 43
<211> LENGTH: 23
<212> TYPE: DNA
<213> ORGANISM: Artificial Sequence
<220> FEATURE:
<223> OTHER INFORMATION: Primer

<400> SEQUENCE: 43
gtcctggctg ctcttctaca agg                                          23

<210> SEQ ID NO 44
<211> LENGTH: 23
<212> TYPE: DNA
<213> ORGANISM: Artificial Sequence
<220> FEATURE:
<223> OTHER INFORMATION: Primer

<400> SEQUENCE: 44
cctggctgct cttctacaag gtg                                          23

<210> SEQ ID NO 45
<211> LENGTH: 23
<212> TYPE: DNA
<213> ORGANISM: Artificial Sequence
<220> FEATURE:
```

```
<223> OTHER INFORMATION: Primer

<400> SEQUENCE: 45
ggtacgtgct gttgaactgt tcc                                            23

<210> SEQ ID NO 46
<211> LENGTH: 29
<212> TYPE: DNA
<213> ORGANISM: Artificial Sequence
<220> FEATURE:
<223> OTHER INFORMATION: Primer

<400> SEQUENCE: 46
gatgtgcagc tgcaggagtc tggrggagg                                      29

<210> SEQ ID NO 47
<211> LENGTH: 35
<212> TYPE: DNA
<213> ORGANISM: Artificial Sequence
<220> FEATURE:
<223> OTHER INFORMATION: Primer

<400> SEQUENCE: 47
ggactagtgc ggccgctgga gacggtgacc tgggt                               35

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
ttatgcttcc ggctcgtatg                                                20

<210> SEQ ID NO 49
<211> LENGTH: 19
<212> TYPE: DNA
<213> ORGANISM: Artificial Sequence
<220> FEATURE:
<223> OTHER INFORMATION: Primer

<400> SEQUENCE: 49
ccacagacag ccctcatag                                                 19

<210> SEQ ID NO 50
<211> LENGTH: 9
<212> TYPE: PRT
<213> ORGANISM: Artificial Sequence
<220> FEATURE:
<223> OTHER INFORMATION: Linker

<400> SEQUENCE: 50

Gly Gly Gly Gly Ser Gly Gly Gly Ser
1               5

<210> SEQ ID NO 51
<211> LENGTH: 11
<212> TYPE: PRT
<213> ORGANISM: Artificial Sequence
<220> FEATURE:
<223> OTHER INFORMATION: Tag

<400> SEQUENCE: 51

Glu Gln Lys Leu Ile Ser Glu Glu Asp Leu Asn
1               5                   10
```

```
<210> SEQ ID NO 52
<211> LENGTH: 6
<212> TYPE: PRT
<213> ORGANISM: Artificial Sequence
<220> FEATURE:
<223> OTHER INFORMATION: Tag

<400> SEQUENCE: 52

His His His His His His
1               5

<210> SEQ ID NO 53
<211> LENGTH: 23
<212> TYPE: PRT
<213> ORGANISM: Artificial Sequence
<220> FEATURE:
<223> OTHER INFORMATION: Sequence C-terminal of bivalent VHH construct

<400> SEQUENCE: 53

Ala Ala Ala Glu Gln Lys Leu Ile Ser Glu Glu Asp Leu Asn Gly Ala
1               5                   10                  15

Ala His His His His His His
            20
```